(12) United States Patent
Hefti

(10) Patent No.: US 6,368,795 B1
(45) Date of Patent: Apr. 9, 2002

(54) BIO-ASSAY DEVICE AND TEST SYSTEM FOR DETECTING MOLECULAR BINDING EVENTS

(75) Inventor: John Hefti, San Francisco, CA (US)

(73) Assignee: Signature BioScience, Inc., Hayward, CA (US)

( * ) Notice: Subject to any disclaimer, the term of this patent is extended or adjusted under 35 U.S.C. 154(b) by 0 days.

(21) Appl. No.: 09/243,194

(22) Filed: Feb. 1, 1999

Related U.S. Application Data

(60) Provisional application No. 60/073,445, filed on Feb. 2, 1998.

(51) Int. Cl.[7] .............................................. G01N 33/543
(52) U.S. Cl. ........................ 435/6; 204/400; 204/403; 422/82.01; 422/82.02; 435/4; 435/7.1; 435/7.92; 435/287.1; 435/287.2; 436/149; 436/150; 436/151; 436/517; 436/518; 436/524; 436/525; 436/806
(58) Field of Search .................... 435/4, 6, 7.1, 7.92, 435/287.1, 287.2; 436/517, 518, 149, 150, 151, 805, 806, 524, 525; 422/82.01, 82.02; 204/400, 403

(56) References Cited

U.S. PATENT DOCUMENTS

| | | | |
|---|---|---|---|
| 4,288,229 A | 9/1981 | Mar | 23/230 |
| 4,407,290 A | 10/1983 | Wilber | 128/633 |
| 4,679,426 A | 7/1987 | Fuller et al. | 73/53 |

(List continued on next page.)

FOREIGN PATENT DOCUMENTS

| | | | |
|---|---|---|---|
| EP | 0519256 A2 * | 12/1992 | G01N/33/543 |
| EP | 0690306 | 1/1996 | |
| WO | WO 93 08464 | 4/1993 | |
| WO | WO 95-03542 | 2/1995 | |
| WO | WO 97/41425 | 4/1996 | |
| WO | WO 96/36871 | 11/1996 | |
| WO | WO 98 09168 | 3/1998 | |
| WO | WO 98 31839 | 7/1998 | |
| WO | WO 99 39190 | 8/1999 | |
| WO | WO 00 45170 | 8/2000 | |

OTHER PUBLICATIONS

Esselle et al. (1988). Capacitive sensors for in–vivo measurements of the dielectric properties of biological materials. IEEE Trans. Instrum. Meas. 37(1):101–105.*

Struchly et al. (1980). Coaxial line reflection methods for measuring dielectric properties of biological substances at radio and microwave frequencies—a review. IEEE Trans. Instrum. Meas. IM–29(3):176–183.*

Ferguson et al. (1996). A fiber–optic DNA biosensor microarray for the analysis of gene expression. Nature Biotech. 14:1681–1684.*

Eggers et al. (1994). A microchip for quantitative detection of molecules utilizing luminescent and radioisotype reporter groups. BioTechniques. 17(3):516–523.*

Stimpson et al. (1995). Real–time detection of DNA hybridization and melting on oligonucleotide arrays by using optical wave guides. PNAS USA. 92:6379–6383.*

Frutos et al. (1998). SPR of ultrathin organic films. Analytical Chemistry news & Features. Jul. 1, 1998, p. 449A–455A.*

(List continued on next page.)

Primary Examiner—Christopher L. Chin
(74) Attorney, Agent, or Firm—Richard L. Neeley; Clifford B. Perry

(57) ABSTRACT

Systems and methods for detecting molecular binding events and other environmental effects using the unique dielectric properties of the bound molecular structure or structures are presented. A molecular binding layer is coupled along the surface of a signal path. A test signal is propagated along the signal path, whereby the test signal couples to the molecular binding layer, and in response, exhibits a signal response.

13 Claims, 28 Drawing Sheets

U.S. PATENT DOCUMENTS

| | | | |
|---|---|---|---|
| 4,765,179 A | | 8/1988 | Fuller et al. ................... 73/53 |
| 4,767,717 A | | 8/1988 | Baisden ....................... 436/64 |
| 4,767,719 A | | 8/1988 | Finlan ........................ 436/501 |
| 4,822,566 A | * | 4/1989 | Newman ..................... 422/68 |
| 5,023,053 A | | 6/1991 | Finlan ..................... 422/82.05 |
| 5,025,222 A | | 6/1991 | Scott .......................... 324/639 |
| 5,047,213 A | | 9/1991 | Finlan et al. ............ 422/82.11 |
| 5,055,265 A | | 10/1991 | Finlan ..................... 422/82.05 |
| 5,064,619 A | | 11/1991 | Finlan ..................... 422/82.05 |
| 5,082,629 A | | 1/1992 | Burgess, Jr. et al. ..... 422/82.11 |
| 5,082,630 A | * | 1/1992 | Partin et al. ................... 422/83 |
| 5,120,648 A | | 6/1992 | Lim et al. .................... 435/173 |
| 5,156,810 A | * | 10/1992 | Ribi ........................ 422/82.01 |
| 5,164,319 A | | 11/1992 | Hafeman et al. ........... 435/291 |
| 5,212,099 A | | 5/1993 | Marcus ....................... 436/172 |
| 5,233,306 A | | 8/1993 | Misra .......................... 324/601 |
| 5,268,573 A | | 12/1993 | Weiss .......................... 250/306 |
| 5,281,814 A | | 1/1994 | Weiss .......................... 250/306 |
| 5,327,225 A | * | 7/1994 | Bender et al. ............... 456/445 |
| 5,328,852 A | | 7/1994 | Blackwood et al. ........ 436/518 |
| 5,340,715 A | * | 8/1994 | Slovavek et al. ............... 435/6 |
| 5,341,215 A | * | 8/1994 | Seher .......................... 356/445 |
| 5,348,003 A | | 9/1994 | Caro ........................... 128/633 |
| 5,363,052 A | | 11/1994 | McKee ....................... 324/663 |
| 5,374,563 A | | 12/1994 | Maule ......................... 436/165 |
| 5,397,896 A | | 3/1995 | Weiss .......................... 250/306 |
| 5,403,747 A | | 4/1995 | Akins, Jr. et al. ............. 436/86 |
| 5,432,096 A | | 7/1995 | Zhu ............................. 436/171 |
| 5,434,084 A | | 7/1995 | Burgess, Jr. ................. 436/52 |
| 5,447,845 A | | 9/1995 | Chu et al. ....................... 435/6 |
| 5,478,748 A | | 12/1995 | Akins, Jr. et al. ............. 436/86 |
| 5,478,755 A | * | 12/1995 | Attridge et al. ............. 436/518 |
| 5,485,277 A | * | 1/1996 | Foster ......................... 356/445 |
| 5,496,701 A | | 3/1996 | Pollard-Knight ............ 435/7.4 |
| 5,508,203 A | | 4/1996 | Fuller et al. ................ 436/149 |
| 5,512,492 A | * | 4/1996 | Herron et al. ............... 436/518 |
| 5,525,466 A | * | 6/1996 | Slovacek et al. ............... 435/6 |
| 5,532,128 A | | 7/1996 | Eggers et al. ................. 435/16 |
| 5,532,493 A | * | 7/1996 | Hale et al. ................ 250/458.1 |
| 5,543,329 A | | 8/1996 | Bedell ........................ 435/7.32 |
| 5,559,328 A | | 9/1996 | Weiss .......................... 250/306 |
| 5,581,193 A | | 12/1996 | Weiss .......................... 324/750 |
| 5,599,668 A | * | 2/1997 | Stimpson et al. ............... 435/6 |
| 5,619,035 A | | 4/1997 | Weiss .......................... 250/306 |
| 5,620,850 A | * | 4/1997 | Bamdad et al. ............. 530/300 |
| 5,629,213 A | * | 5/1997 | Kornguth et al. ........... 436/518 |
| 5,647,030 A | * | 7/1997 | Jorgenson et al. ............ 385/12 |
| 5,653,939 A | | 8/1997 | Hollis et al. .................. 422/50 |
| 5,656,428 A | | 8/1997 | McAllister et al. | |
| 5,661,301 A | | 8/1997 | Weiss .......................... 250/307 |
| 5,738,992 A | * | 4/1998 | Cook et al. ..................... 435/6 |
| 5,792,668 A | | 8/1998 | Fuller et al. ................ 436/149 |
| 5,822,073 A | * | 10/1998 | Yee et al. .................... 356/445 |
| 5,827,482 A | | 10/1998 | Shieh et al. ............. 422/82.02 |
| 5,832,165 A | * | 11/1998 | Reichert et al. ............. 385/130 |
| 5,835,645 A | * | 11/1998 | Jorgenson et al ............. 385/12 |
| 5,841,914 A | | 11/1998 | Shieh et al. .................... 385/12 |
| 5,843,651 A | * | 12/1998 | Stipmson et al. ............... 435/6 |
| 5,846,708 A | | 12/1998 | Hollis et al. .................... 435/6 |
| 5,846,842 A | * | 12/1998 | Herron et al. ............... 436/518 |
| 5,846,843 A | | 12/1998 | Simon ........................ 436/527 |
| 5,858,666 A | * | 1/1999 | Weiss ............................ 435/6 |
| 5,858,799 A | * | 1/1999 | Yee et al. .................... 436/164 |
| 5,869,261 A | * | 2/1999 | Tosa ........................... 435/7.1 |
| 5,892,577 A | | 4/1999 | Gordon ....................... 356/73 |
| 5,919,712 A | * | 7/1999 | Herron et al. ............... 136/518 |
| 5,926,773 A | | 7/1999 | Wagner ....................... 702/22 |
| 5,955,729 A | * | 9/1999 | Nelson et al. ............... 250/282 |
| 5,961,924 A | * | 10/1999 | Reichert et al. ......... 422/82.11 |
| 5,965,456 A | * | 10/1999 | Malmqvist et al. ......... 436/514 |
| 5,991,048 A | * | 11/1999 | Karlson et al. ............. 356/445 |
| 6,035,246 A | | 3/2000 | Wagner ...................... 700/266 |
| 6,048,692 A | | 4/2000 | Maracas et al. ............... 435/6 |

OTHER PUBLICATIONS

Hanken et al. (1997). Synthesis, spectroscopic characterization, and electro–optical properties of noncentrosymetric azobenzene/zirconium phosphate multilayer films. Anal. Chem. 69(2):240–248.*

Amo et al., "Dielectric Measurement of Lysozyme and Tri–N–Acetyl–D–Glucosamine Association at Radio and Microwave Frequencies", Biosensors & Bioelectronics, 12(9–10):953–958 (1997).

Hollis et al., A Swept Frequency Magnitude Method for the Dielectric Characterization of Chemical and Biological Systems, IEEE Transaction on Microwave Theory and Techniques, vol. MTTT–28 No. 7, Jul. 1980, pp. 791–801.

Hianik, "Biosensors Based on Solid Supported Lipid Bilayers and their Physical Properties", Nato Asi Ser., Ser. 2 (1997), 38 (Biosensors for Direct Monitoring of Enviromental Pollutanta in Field), 317–333.

Yuko et al., "Dielectric Measurements of Lysozyme and Tri–N–Acetyl–D–Glucosamine Association at Radio and Microwave Frequencies", Biosensors & Bioelectrincs, 12(9–10):953–958 (1997).

Smith et al., "Dielectric Relaxation Spectroscopy and Some Applications in the Pharmaceutical Sciences", Journal of Pharmaceutical Science, 84(9):1029–1044 (1995).

* cited by examiner

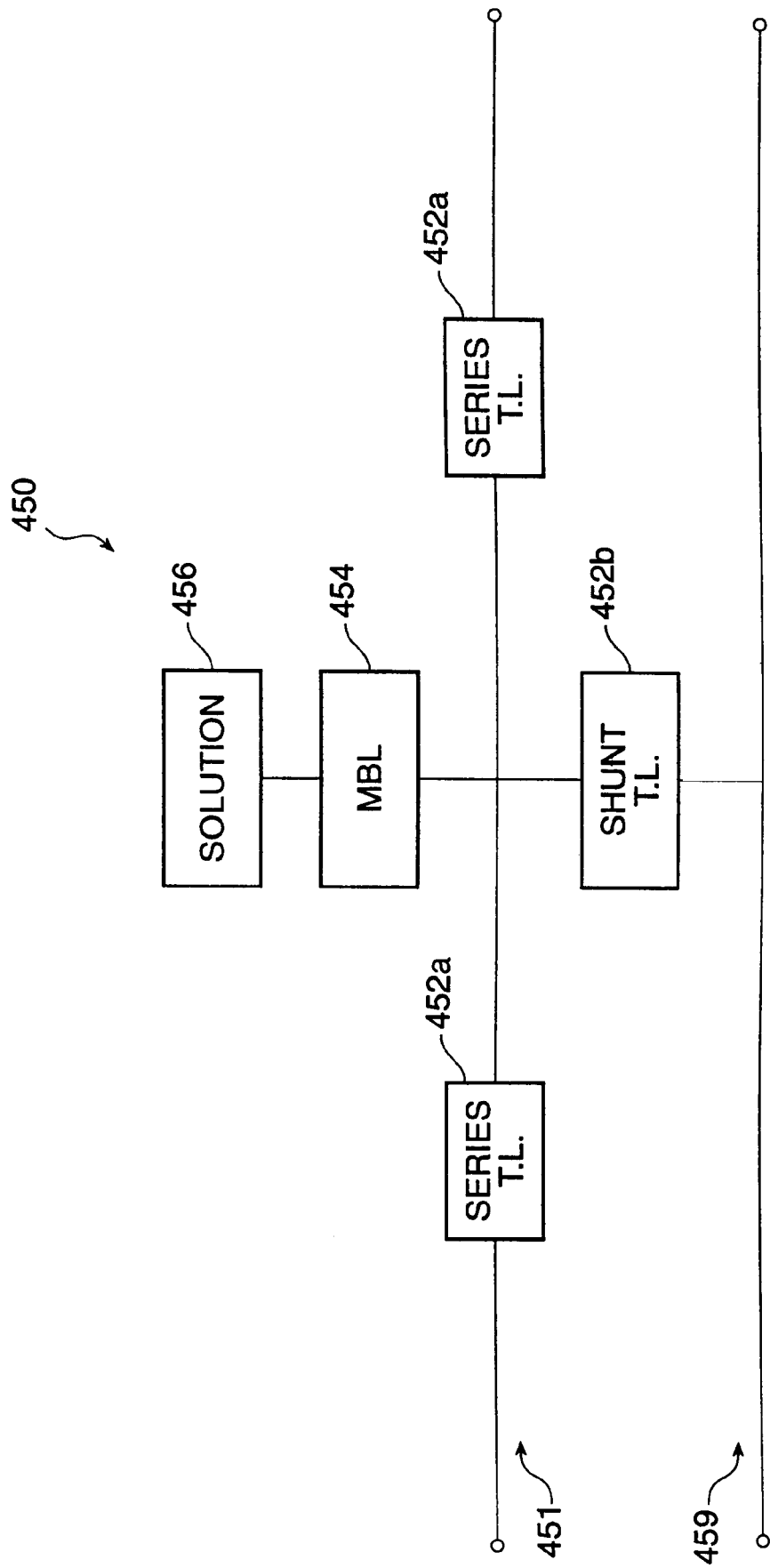

BIO-ASSAY DEVICE AND TEST SYSTEM FOR DETECTING MOLECULAR BINDING EVENTS

CROSS-REFERENCES TO RELATED APPLICATIONS

This application claims priority from a previously filed provisional application entitled: "The Detection of Molecular Binding Events on a Conductive Surface," Ser. No. 60/073,445, filed on Feb. 2, 1998, the contents of which are incorporated herein by reference.

BACKGROUND OF THE INVENTION

Virtually every area of biomedical sciences is in need of a system to assay chemical and biochemical reactions and determine the presence and quantity of particular analytes. This need ranges from the basic science research lab, where biochemical pathways are being mapped out and their functions correlated to disease processes, to clinical diagnostics, where patients are routinely monitored for levels of clinically relevant analytes. Other areas include pharmaceutical research, military applications, veterinary, food, and environmental applications. In all of these cases, the presence and quantity of a specific analyte or group of analytes, needs to be determined.

For analysis in the fields of chemistry, biochemistry, biotechnology, molecular biology and numerous others, it is often useful to detect the presence of one or more molecular structures and measure binding between structures. The molecular structures of interest typically include, but are not limited to, cells, antibodies, antigens, metabolites, proteins, drugs, small molecules, proteins, enzymes, nucleic acids, and other ligands and analytes. In medicine, for example, it is very useful to determine the existence of a cellular constituents such as receptors or cytokines, or antibodies and antigens which serve as markers for various disease processes, which exists naturally in physiological fluids or which has been introduced into the system. Additionally, DNA and RNA analysis is very useful in diagnostics, genetic testing and research, agriculture, and pharmaceutical development. Because of the rapidly advancing state of molecular cell biology and understanding of normal and diseased systems, there exists an increasing need for methods of detection, which do not require labels such as fluorophores or radioisotopes, are quantitative and qualitative, specific to the molecule of interest, highly sensitive and relatively simple to implement.

Numerous methodologies have been developed over the years to meet the demands of these fields, such as Enzyme-Linked Immunosorbent Assays (ELISA), Radio-Immunoassays (RIA), numerous fluorescence assays, mass spectroscopy, colorimetric assays, gel electrophoresis, as well as a host of more specialized assays. Most of these assay techniques require specialized preparations, especially attaching a label or greatly purifying and amplifying the sample to be tested. To detect a binding event between a ligand and an antiligand, a detectable signal is required which relates to the existence or extension of binding. Usually the signal is provided by a label that is conjugated to either the ligand or antiligand of interest. Physical or chemical effects which produce detectable signals, and for which suitable labels exist, include radioactivity, fluorescence, chemiluminescence, phosphorescence and enzymatic activity to name a few. The label can then be detected by spectrophotometric, radiometric, or optical tracking methods. Unfortunately, in many cases it is difficult or even impossible to label one or all of the molecules needed for a particular assay. Also, the presence of a label may make the molecular recognition between two molecules not function for many reasons including steric effects. In addition, none of these labeling approaches determines the exact nature of the binding event, so for example active site binding to a receptor is indistinguishable from non-active-site binding such as allosteric binding, and thus no functional information is obtained via the present detection methodologies. Therefore, a method to detect binding events that both eliminates the need for the label as well as yields functional information would greatly improve upon the above mentioned approaches.

Other approaches for studying biochemical systems have used various types of dielectric measurements to characterize certain classes of biological systems such as tissue samples and cellular systems. In the 1950's, experiments were conducted to measure the dielectric properties of biological tissues using standard techniques for the measurement of dielectric properties of materials known at the time. Since then various approaches to carrying out these measurements have included frequency domain measurements, and time domain techniques such as Time Domain Dielectric Spectroscopy. In these approaches, the experiments were commonly carried out using various types of coaxial transmission lines, or other transmission lines and structures of typical use in dielectric characterization of materials. This included studies to look at the use and relevance of the dielectric properties of a broad range of biological systems: The interest has ranged from whole tissue samples taken from various organs of mammalian species, to cellular and sub-cellular systems including cell membrane and organelle effects. Most recently, there have been attempts to miniaturize the above-mentioned techniques (see e.g., U.S. Pat. Nos. 5,653,939; 5,627,322 and 5,846,708) for improved detection of changes in the dielectric properties of molecular systems. Typically these use the biological sample—be it tissues, cellular systems, or molecular systems—as a shunt or series element in the electrical circuit topology. This configuration has several drawbacks, including some substantial limitations on the frequencies useable in the detection strategy, and a profound limitation on the sensitivity of detecting molecular systems.

In general, limitations exist in the areas of specificity and sensitivity of most assay systems. Cellular debris and non-specific binding often cause the assay to be noisy, and make it difficult or impossible to extract useful information. As mentioned above, some systems are too complicated to allow the attachment of labels to all analytes of interest, or to allow an accurate optical measurement to be performed. Further, a mentioned above, most of these detection technologies yield no information on the functional nature of the binding event. Therefore, a practical and economical universal enabling which can directly monitor without a label, in real time, the presence of analytes or the extent, function and type of binding events that are actually taking place in a given system would represent a significant breakthrough.

More specifically, the biomedical industry needs an improved general platform technology which has very broad applicability to a variety of water-based or other fluid-based physiological systems, such as nucleic acid binding, protein-protein interactions, small molecule binding, as well as other compounds of interest. Ideally, the assay should not require highly specific probes, such as specific antibodies and exactly complementary nucleic acid probes; it should be able to work in native environments such as whole blood, cytosolic mixtures, as well as other naturally occurring systems; it should operate by measuring the native properties of the molecules, and not require additional labels or tracers to actually monitor the binding event; for some uses it should be able to provide certain desired information on the nature of the binding event, such as whether or not a given compound acts as an agonist or an antagonist on a particular drug receptor, and not function simply as a marker to indicate whether or not the binding event has taken place. For many applications, it should be highly miniaturizable and highly parallel, so that complex biochemical pathways can be mapped out, or extremely small and numerous quantities of combinatorial compounds can be used in drug screening protocols. In many applications, it should further be able to monitor in real time a complex series of reactions, so that accurate kinetics and affinity information can be obtained almost immediately. Perhaps most importantly, for most commercial applications it should be inexpensive and easy to use, with few sample preparation steps, affordable electronics and disposable components, such as surface chips for bioassays that can be used for an assay and then thrown away, and be highly adaptable to a wide range of assay applications.

It is important to note that other industries have similar requirements for detection, identification or additional analysis. While most applications involve the use of biological molecules, virtually any molecule can be detected if a specific binding partner is available or if the molecule itself can attach to the surface as described below.

The present invention fulfills many of the needs discussed above and other needs as well.

SUMMARY OF THE INVENTION

The present invention provides systems and methods for detecting molecular binding events and other environmental effects using the unique dielectric properties of the bound molecular structure or structures, and the local environment, and also identifying the presence and concentrations of molecular species, as well as physical properties of the local environment, in a particular biological system.

In a first embodiment of the invention, a method for detecting a molecular binding event includes the steps of providing a signal path and a molecular binding layer, which is formed along the signal path. A test signal is propagated along the signal path and couples to the molecular binding layer. In response to the coupling, the signal exhibits a response which is indicative of both the molecular binding event and the molecular binding layer itself.

In a second embodiment of the invention, a method for determining the classification of an unknown ligand is presented. The method comprises the steps of providing a signal path coupled to a first molecular binding layer having N respective antiligands for binding to N respective ligand sub-structures. Next a solution containing a number of unknown ligands is applied to the said molecular binding layer. In response, a second molecular binding layer is formed along the signal path, the second molecular binding layer having N ligands. N respective test signals are propagated to the N respective ligands. N known signal responses defining a known ligand classification are provided. Finally, each of the test signals couples to the N ligand/antiligand complexes, and in response exhibits N respective measured responses indicative of the presence of each of said N sub-structures, so that if a predetermined number of said N known signal responses correlates within a predefined range with the N measured responses, the ligand is determined to be within the known classification.

In a third embodiment of the invention, a method for identifying an unknown molecular binding event is presented. The method includes the steps of providing a signal path, applying a first solution containing a first ligand over the signal path, and forming, in response, a first molecular binding layer along the signal path, whereby the first molecular layer includes the first ligand and is positioned along the signal path and the first solution. A first test signal is propagated along the signal path, the portion of which includes the molecular binding layer comprises a continuous transmission line, whereby the signal couples to the molecular binding layer and in response exhibits a first signal response. A known signal response corresponding to a known molecular binding event is provided and the first signal response is then compared to the known signal response, wherein if the first signal response correlates to the known signal response within a predefined range, the unknown molecular binding event comprises the known molecular binding event.

In a fourth embodiment of the invention, a method for quantitating an unknown concentration of ligands in solution is presented. The method includes the steps of providing a signal path which is coupled to a first molecular binding layer having at least one antiligand, applying a solution having a known concentration of ligands over the molecular binding layer, and propagating a test signal along the signal path. Next a first signal response is measured and an extrapolation algorithm is generated. A second test signal is subsequently propagated and a second signal response is measured. The second signal response is then correlated to the algorithm.

In a fifth embodiment of the invention, a bio-electrical interface is provided for detecting the presence of a ligand in a solution. The bio-electrical interface includes a signal path, a solution for providing the ligand and a molecular binding layer. The molecular binding layer includes the ligand and is coupled along the signal path and the solution.

In a sixth embodiment of the invention, a bio-assay device is provided for detecting one or more properties associated with a molecular binding layer, such as the presence of a ligand, using a test signal. The apparatus includes a signal path having a first port and a second port for communicating the test signal, and a continuous conductive region therebetween. The bio-assay device further includes a molecular binding layer, which may have a ligand, and which is coupled to the signal path. The bio-assay device may further include a solution coupled to said molecular binding layer, which may transport the ligand to the molecular binding layer.

In a seventh embodiment of the invention, a system for detecting a molecular binding event is presented. The system includes a signal source for launching a test signal, a bio-assay device coupled to said signal source and a second detector coupled to the bio-assay device. The bio-assay device includes a signal path and a first molecular binding layer, which may include a ligand or antiligand, and which may be coupled to a solution and the signal path. The test signal propagates along the signal path, which is continuous throughout the region of the molecular binding layer, and couples to the molecular binding layer, and in response exhibits a signal response which indicates the presence of said molecular binding event.

In one aspect, the present invention is the use of the interaction of electromagnetic radiation, typically between about 1 MHz and 1000 GHz, with molecular structures in a molecular binding layer to determine properties of the structures, such as dielectric properties, structural properties, binding events and the like. Also, the present invention uses a test signal on a bio-electrical interface having a signal path along which the molecular binding layer is coupled to detect analytes therein.

The nature and advantages of the present invention will be better understood with reference to the following drawings and detailed description.

BRIEF DESCRIPTION OF THE DRAWINGS

FIG. 4C illustrates one embodiment of an equivalent circuit model for the bio-electrical interface structure shown in FIG. 2B.

DESCRIPTION OF THE SPECIFIC EMBODIMENTS

Table of Contents

I. Definition of Terms

II. Introduction

Figure 1A:
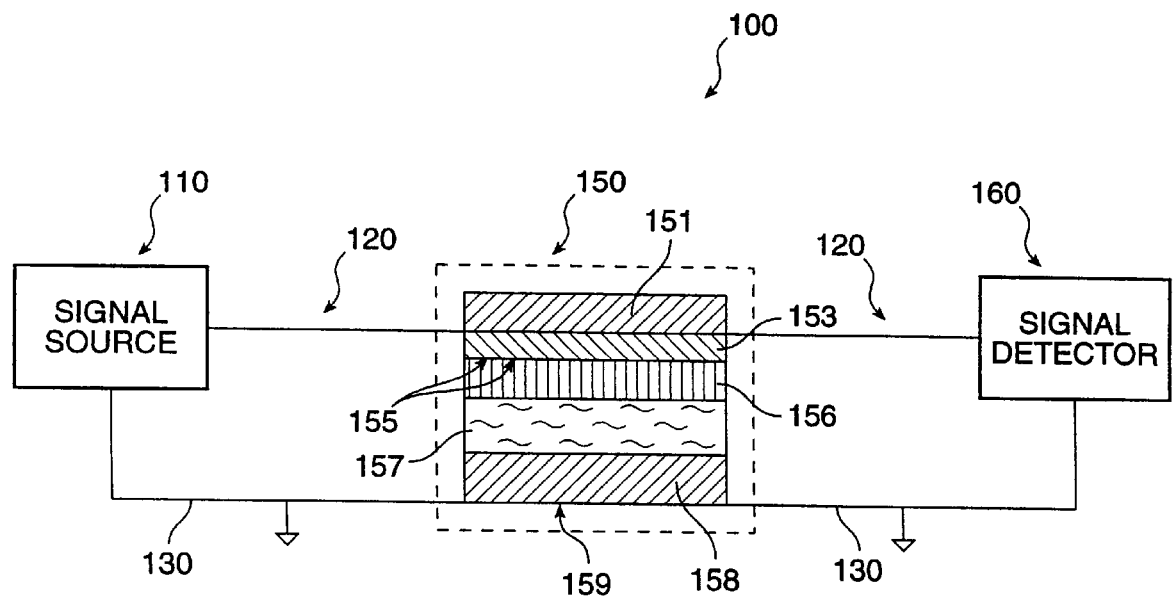
FIG. 1A illustrates one embodiment of the bio-assay system in accordance with the present invention.

A. Bio-Assay System
B. Chemistry of the System
III. The Bio-Assay Device
  A. Device Structure
  B. Binding Surface Chemistry
  C. Bio-Electrical Interface
  D. Specific Embodiments
IV. Measurement Methodology
  A. General Overview
  B. Detecting Molecular Binding Events
  C. Detecting Changes in the Dielectric Properties
  D. Identifying Molecular Binding Events
  E. Identifying Classes of Bound Molecular Structures
  F. Quantitating Concentrations
  G. Bio-Assay Device Self-Calibration
V. Measurement Systems
  A. Frequency Measurement System
  B. Time Domain Measurement System
  C. Dielectric Relaxation Measurement System
VI. Examples
VII. Applications
I. Definition of Terms As used herein, the terms biological "binding partners" or "ligand/antiligand" or "ligand/antiligand complex" refers to molecules that specifically recognize (e.g. bind) other molecules to form a binding complex such as antibody-antigen, lectin-carbohydrate, nucleic acid-nucleic acid, biotin-avidin, etc. Biological binding partners need not be limited to pairs of single molecules. Thus, for example, a single ligand may be bound by the coordinated action of two or more "antiligands".

As used herein, the term "ligand" or "analyte" or "marker" refers to any molecule being detected. It is detected through its interaction with an antiligand, which specifically or non-specifically binds the ligand, or by the ligand's characteristic dielectric properties. The ligand is generally defined as any molecule for which there exists another molecule (i.e. an antiligand) which specifically or non-specifically binds to said ligand, owing to recognition of some portion of said ligand. The antiligand, for example, can be an antibody and the ligand a molecule such as an antigen which binds specifically to the antibody. In the event that the antigen is bound to the surface and the antibody is the molecule being detected, for the purposes of this document the antibody becomes the ligand and the antigen is the antiligand. The ligand may also consist of cells, cell membranes, organelles and synthetic analogues thereof.

Suitable ligands for practice of this invention include, but are not limited to antibodies (forming an antibody/epitope complex), antigens, nucleic acids (e.g. natural or synthetic DNA, RNA, gDNA, cDNA, mRNA, tRNA, etc.), lectins, sugars (e.g. forming a lectin/sugar complex), glycoproteins, receptors and their cognate ligand (e.g. growth factors and their associated receptors, cytokines and their associated receptors, signaling receptors, etc.), small molecules such as drug candidates (either from natural products or synthetic analogues developed and stored in combinatorial libraries), metabolites, drugs of abuse and their metabolic by-products, co-factors such as vitamins and other naturally occurring and synthetic compounds, oxygen and other gases found in physiologic fluids, cells, cellular constituents cell membranes and associated structures, other natural products found in plant and animal sources, other partially or completely synthetic products, and the like.

As used herein, the term "antiligand" refers to a molecule which specifically or nonspecifically binds another molecule (i.e., a ligand). The antiligand is also detected through its interaction with a ligand to which it specifically binds or by its own characteristic dielectric properties. As used herein, the antiligand is usually immobilized on the surface, either alone or as a member of a binding pair that is immobilized on the surface. In some embodiments, the antiligand may consist of the molecules on the signal path or conductive surface. Alternatively, once an antiligand has bound to a ligand, the resulting antiligand/ligand complex can be considered an antiligand for the purposes of subsequent binding.

As used herein, the term "specifically binds" when referring to a protein or polypeptide, nucleic acid, or receptor or other binding partners described herein, refers to a binding reaction which is determinative of the cognate ligand of interest in a heterogenous population of proteins and/or other biologics. Thus, under designated conditions (e.g. immunoassay conditions in the case of an antibody), the specified ligand or antibody binds to its particular "target" (e.g. a hormone specifically binds to its receptor) and does not bind in a significant amount to other proteins present in the sample or to other proteins to which the ligand or antibody may come in contact in an organism or in a sample derived from an organism. Similarly, nucleic acids may hybridize to one another under preselected conditions.

As used herein, the terms "isolated" "purified" or "biologically pure" refer to material which is substantially or essentially free from components that normally accompany it as found in its native state.

As used herein, the term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

As used herein, the terms "polypeptide", "peptide" and "protein" are used interchangeably to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein, the term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to VH-CH1 by a disulfide bond. The $F(ab)'_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH::VL heterodimer which may be expressed from a nucleic acid including VH- and VL-encoding sequences either joined directly or joined by a peptide-encoding linker. Huston, et al. (1988) Proc. Nat. Acad. Sci. USA, 85:5879–5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

As used herein, the terms "immunological binding" and "immunological binding properties" refer to the non-covalent interactions of the type which occur between an immunoglobulin molecule and an antigen for which the immunoglobulin is specific. As used herein, a biological sample is a sample of biological tissue or fluid that, in a healthy and/or pathological state, that is to be assayed for the analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect the analyte(s) of interest in samples from any mammal, such as dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

As used herein, the term "signal path" refers to a transmission medium along the bio-electrical interface which is capable of supporting an electromagnetic signal of any useful frequency including a DC static field. A non-exhaustive list of signal paths include conductive and dielectric waveguide structures, multiple-conductor transmission mediums such as transverse electromagnetic (TEM) transmission lines, transmission lines with three or more conductive elements which support TE, TM or TEM mode propagation such as quadrupolar and octupolar lines, coupled waveguides, resonant cavity structures which may or may not be coupled, other non-modal structures like wires, printed circuits, and other distributed circuit and lumped impedance conductive structures, and the like. The signal path may structurally comprise the signal plane, the ground plane, or a combination of both structures. Typically, the signal path is formed along a direction which is non-orthogonal to the surface of the MBL. In embodiments in which the signal path consists of a conductive layer or region, the conductive region extends continuously over that range. In embodiments in which the signal path is non-metallic, i.e., a dielectric waveguide, the signal path is defined as the path having the least amount of signal loss or as having a conductivity of greater than 3 mhos/m.

As used herein, the terms "molecular binding layer" or "MBL" refers to a layer having of at least one molecular structure (i.e., an analyte, antiligand, or a ligand/antiligand pair, etc.) coupled to the signal path along the bio-electrical interface. The molecular binding layer may consist of one or more ligands, antiligands, ligand/antiligand complexes, linkers, matrices of polymers and other materials, or other molecular structures described herein. Further, the molecular binding layer may be extremely diverse and may include one or more components including matrix layers and/or insulating layers, which may have one or more linking groups. The MBL is coupled to the signal path either via a direct or indirect physical connection or via electromagnetic coupling when the ligand is physically separated from the signal path. The MBL may be of a derivatized surface such as by thiol linkers biotinylated metals and the like, all in accordance with standard practice in the art.

As used herein, the term "binding event" refers to an interaction or association between a minimum of two molecular structures, such as a ligand and an antiligand. The interaction may occur when the two molecular structures as are in direct or indirect physical contact or when the two structures are physically separated but electromagnetically coupled therebetween. Examples of binding events of interest in a medical context include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Alternatively, the term "binding event" may refer to a single molecule or molecular structure described herein, such as a ligand, or an antiligand/ligand complex, which is bound to the signal path. In this case the signal path is the second molecular structure.

As used herein, the term "Ligand/antiligand complex" refers to the ligand bound to the antiligand. The binding may be specific or non-specific, and the bonds are typically covalent bonds, hydrogen bonds, immunological binding, Van der Waals forces, or other types of binding.

As used herein, the term "coupling" refers to the transfer of energy between two structures either through a direct or indirect physical connection or through any form of signal coupling, such as electrostatic or electromagnetic coupling.

As used herein, the term "test signal" refers to a signal propagating at any useful frequency defined within the electromagnetic spectrum. For examples, the test signal frequency is at or above 1 MHz, such as 5 MHZ 10 MHz, 20 MHz, 45 MHz, 100 MHz, 500 MHz, 1 GHz, 5 GHz, 10 GHz, 30 GHz, 50 GHz, 100 GHz, 500 GHz, 1000 GHz and frequencies ranging therebetween.

As used herein, the term "enzyme," refers to a protein which acts as a catalyst to reduce the activation energy of a chemical reaction in other compounds or "substrates", but is not a final product in the reaction.

As used herein, the term "solution" includes a material in which a ligand resides. A non-exhaustive list of solutions includes materials in solid, liquid or gaseous states. Solid solutions may be comprised of naturally-occurring or synthetic molecules including carbohydrates, proteins, oligonucleotides, or alternatively, any organic polymeric material, such as nylon, rayon, dacryon, polypropylene, teflon, neoprene, delrin or the like. Liquid solutions include those containing an aqueous, organic or other primary components, gels, gases, and emulsions. Exemplary solutions include celluloses, dextran derivatives, aqueous solution of d-PBS, Tris buffers, deionized water, blood, physiological buffer, cerebrospinal fluid, urine, saliva, water, organic solvents. The solution is used herein to refer to the material in which the ligand and/or antiligand are applied to the binding surface. The solution contains the sample to be analyzed.

As used herein, the term "linking group" or "linker" refers to chemical structures which are used to attach any two components on the bio-assay device. The linking groups thus have a first binding portion that binds to one component, such as the conductive surface, and have a second binding portion that binds to another component such as the matrix or the antiligand.

As used herein, the term "bio-assay device" refers to a structure in which the molecular binding layer is formed. The bio-assay device may consist of a surface, recessed area, or a hermetically sealed enclosure, all of which may be any particular size or shape.

As used herein, the "bio-assay system" refers to the bio-assay device as described above, in connection with the components necessary to electromagnetically probe and detect the bio-assay device. These components include, but are not limited to, the signal path(s), substrate(s), electronic devices such as signal generators, oscilloscopes, and vector analyzers necessary to probe to and detect signals from the bio-assay device, microchips and microprocessors which can probe and detect electromagnetic signals and analyze data, and the like.

As used herein, the term "resonant" or "resonance" refers generally to a rapidly changing dielectric response as a function of frequency.

As used herein, "bio-electrical interface" refers to an interface structure between a signal path for supporting the propagation of a test signal and a molecular binding layer.

As used herein, the term "matrix" or "binding matrix" refers to a layer of material on the bioassay chip that is used as a spacer or to enhance surface area available for binding or to optimize orientation of molecules for enhanced binding, or to enhance any other property of binding so as to optimize the bio-assay device. The matrix layer may be comprised or carbohydrates such as dextran, poly amino acids, cross-linked and non-cross linked proteins, and the like.

II. Introduction

A. The Bio-Assay System

The present invention makes use of the observation that a vast number of molecules can be distinguished based upon the unique dielectric properties most molecules exhibit. These distinguishing dielectric properties can be observed by coupling a signal to the bound molecular structure. The unique dielectric properties modulate the signal, giving it a unique signal response. The unique signal response can then be used to detect and identify the ligands and other molecules which make up the molecular binding layer.

FIG. 1A illustrates one embodiment of a bio-assay system 100 in accordance with the present invention. The system 100 is illustrated in a two conductor, signal-plane ground-plane, circuit topology which may be realized in a multitude of architectures including lumped or distributed element circuits in microstrip, stripline, coplanar waveguide, slotline or coaxial systems. Moreover, those of skill in the art of electronics will readily appreciate that the system may be easily modified to a single conductor waveguide system, or a three or more conductor system.

As illustrated, the system 100 includes a signal source 110, transmission lines 120, a ground plane 130, a bio-assay device 150, and a signal detector 160. The illustrated embodiment shows two transmission lines 120 coupled to the bio-assay device 150, although in alternative embodiments a single transmission line may be coupled to the bio-assay device or further alternatively, three or more transmission lines may coupled to the bio-assay device 150. Transmission lines 120 are formed from a material which can support the propagation of a signal over the desired frequency of operation. Transmission lines 120 are realized as a conductive layer, such as gold, deposited on a substrate, such as alumina, diamond, sapphire, polyimide, or glass using conventional photolithography or semiconductor processing techniques.

The system 100 further includes a bio-assay device 150 coupled to the transmission lines 120. The bio-assay device 150 contains a supporting substrate 151 onto which a conductive layer 153 is disposed. The conductive layer 153 forms an interface for supporting the propagation of a test signal. The supporting substrate 151 may consists of any insulating material such as glass, alumina, diamond, sapphire, silicon, gallium arsenide or other insulating materials used in semiconductor processing.

A molecular binding layer (MBL) 156 is coupled to one or more areas of the interface transmission line 153. As those of skill in the art of electronics will appreciate, coupling may occur either through a direct connection between the interface transmission line 153 and MBL 156 as illustrated, or alternatively through signal coupling, further described below.

The MBL 156 is primarily composed of one or more ligands, although other molecules and structures may also be included, as described herein. The MBL 156 may consist of only one bound ligand tier, for instance in the case of primary binding, or it may consist of two, three, four, five or more bound ligand tiers, in the instances where there are secondary or higher-order binding events occurring. Multiple ligand tiers may occur at different binding surfaces 155 over the same interface transmission line 153.

In the illustrated embodiment, dielectric substrate 158 is located between solution 157 and ground plane 159. In the illustrated embodiment, dielectric layer 158 and ground plane 159 are located within the bio-assay device 150, although in alternative embodiments, one or both may be located externally. Furthermore, the MBL 156 and solution 157 arrangement may be switched and moved towards the ground plane alternatively, or in addition to these layers' proximity to the interface transmission line 153.

The system 100 includes a signal source 110 which launches the test signal onto the transmission line 120 and towards the bio-assay device 150. A signal detector 160 is positioned along the transmission path to detect the resulting signal (either reflected or transmitted or both). When the signal propagates along the interface transmission line 153 of the bio-assay device 150, the dielectric properties of the MBL 156 modulates the test signal. The modulated signal can then be recovered and used to detect and identify the molecular binding events occurring within the bio-assay device, further described below.

In an alternative embodiment of the invention, detection and identification of a ligand, antiligand/ligand complex or other molecular structure described herein is possible when it is physically separated from the interface transmission line 153. In this embodiment, the ligand is separated from but electrically or electromagnetically coupled to the interface transmission line 153. The coupling between the interface transmission line 153 and the suspended ligand will alter the response of the test signal propagating along the interface transmission line 153, thereby providing a means for detecting and/or identifying it. The maximum separation between the interface transmission line 153 and suspended ligand is determined by such factors as the effective dielectric constant of the medium between the interface transmission line 153 and the ligand, the total coupling area, the sensitivity of the signal detector, concentration of the ligands in solution, and the desired detection time. Separation distances are typically on the order of $10^{-1}$ m, $10^{-2}$ m $10^{-3}$ m, $10^{-4}$ m, $10^{-5}$ m, $10^{-6}$ m, $10^{-7}$ m, $10^{-8}$ m, $10^{-9}$ m, $10^{-10}$ m or range anywhere therebetween.

In some embodiment, such as cell based assays, the MBL may be electromagnetically coupled to the signed path through the solution. Thus, cells, and in particular cell membranes and membrane-based structures may couple to the signal.

Figure 1B:
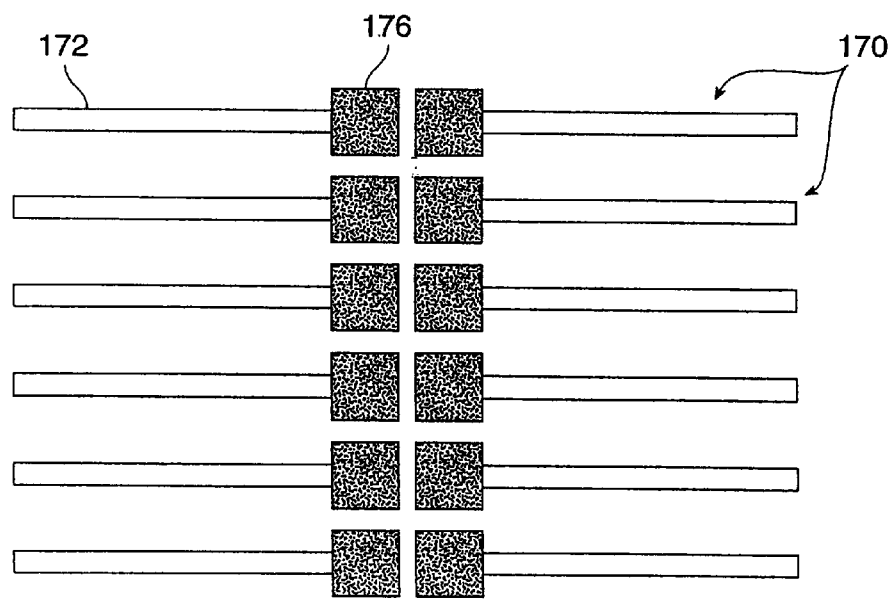
FIG. 1B illustrates a second embodiment of the bio-assay system in accordance with the present invention.

FIG. 1B illustrates a second embodiment of the bio-assay system comprising an array of resonant microstrip circuits 170. Each resonant circuit 170 consists of a transmission line 172 terminating in an open-circuited stub 176. Those skilled in the art of circuit design will appreciate other resonant structures may be employed in lumped element, distributed, or a combination of both circuit topologies.

Figure 1C:
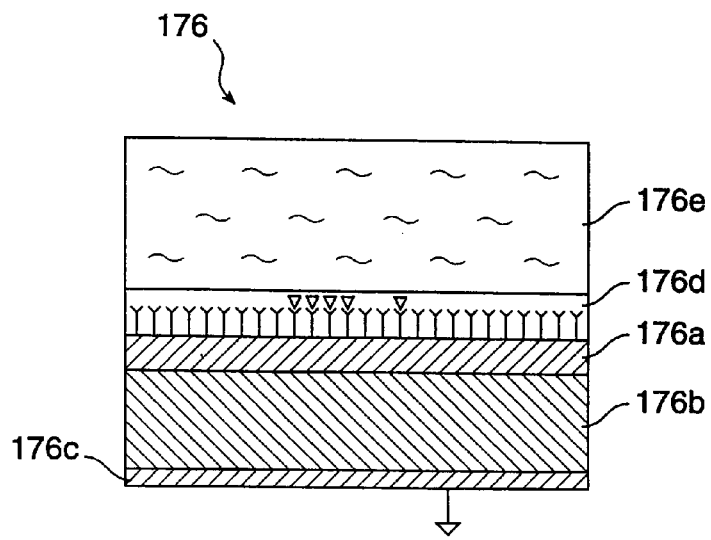
FIG. 1C illustrates a cross-section view of the bio-assay system shown in FIG. 1B.

FIG. 1C illustrates a cross-section view of one resonant circuit 170. The open-circuited stub 176 forms the bio-electrical interface of the resonant circuit 170 and closely parallels the bio-electrical interface shown in FIG. 1A. In particular, the open-circuited stub 176 consists of an interface transmission line 176a deposited on a dielectric layer 176b, and is positioned above ground plane 176c.

In this embodiment, the MBL 176d is coupled via a direct connection to transmission line 176a. The MBL 176d can bind along the interface transmission line in a specific or non-specific manner. As above, the subject molecular structure may be suspended from but electrically coupled or electromagnetically coupled to the interface transmission line 176a to provide binding event detection and identification information.

The dimensions of the interface transmission line 176a are influenced by considerations such as the desired measurement time (a larger area resulting in faster detection time), the desired resonant frequency $f_{res}$, certain impedance matching conditions to achieve higher efficiency or cause discontinuities to highlight binding events, and the process by which the entire array is formed. For instance, if conventional microwave photolithography is used, the binding surface area may range from $10^{-1}$ m$^2$ to $10^{-6}$ m$^2$ using a relatively thick dielectric layer such as alumina, diamond, sapphire, duriod or other conventional substrate materials. Alternatively, if semiconductor processing is used, the binding surface area may range from $10^{-6}$ m$^2$ to $10^{-12}$ m$^2$ using a relatively thin dielectric layer of silicon or gallium arsenide.

Using conventional microwave design techniques or CAD tools such as Microwave Spice™, EBsof Touchstone™ and Libra™, the length and impedance of the transmission line 172, the dimensions of the interface transmission line 176a, and the thickness and dielectric constant of the dielectric layer 176b can be selected such that the resonant structure exhibits a resonant signal response at a desired resonant frequency point $f_{res}$. The desired resonant frequency $f_{res}$ point is typically the frequency range over which the molecules of interest exhibit a dramatic change in their dielectric properties, the measurement of which will enable their detection. Alternatively, the resonant frequency point $f_{res}$ can be defined as the center of the desired test frequency range to allow for the widest range of signal detection. In the illustrated embodiment, the resonant frequency $f_{res}$ includes 10 MHz, 20 MHz, 45 MHz, 100 MHz, 500 MHz, 1 GHz, 5 GHz, 10 GHz, 30 GHz, 50 GHz, 100 GHz, 500 GHz, 1,000 GHz or frequencies ranging therebetween.

During measurement, the solution 176e is applied over one or more of the open-circuited stubs 172. A MBL 176d is formed when one or molecules within the solution bind to the interface transmission line 176a. In this instance, the MBL 176d and the solution electrically behave as a parasitic circuit, further described below, which causes the resonant frequency point $f_{res}$ to shift above or below its original resonant frequency point. This shift in frequency can be detected, and is used to indicate the occurrence of a molecular binding event. The signal response may also be interrogated over a wide spectrum to ascertain the identity of the bound molecular structure, as described below. Each resonant circuit 170 may be fabricated to bind different molecular structures and each resonant circuit 170 be made addressable, thereby permitting simultaneous detection and identification of a large numbers of molecular structures within the same solution. In an alternative embodiment, each resonant circuit 170 may be designed to exhibit a distinct resonant frequency, in which case all of the resonant circuits 170 may be interrogated over a continuous frequency spectrum to determine molecular binding.

B. Chemistry of the System

The chemistry of the system generally occurs within the bio-assay device, and in particular along the conductive layer (interface transmission line in FIGS. 1A–1C). The conductive layer is fabricated from materials and having a morphology which is conducive to support the propagation of the high frequency test signal. The conductive surface is constructed from materials exhibiting appropriate conductivity over the desired test frequency range as well as possessing good molecular binding qualities as described above. Such materials include, but are not limited to gold, indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof The conductive layer may also be formed from semiconducting materials which may be either crystalline or amorphous in structure, including chemically doped or pure carbon, silicon, germanium, gallium-arsenide, idium-gallium arsenide, or the like. The conductive material may also be formed from polymers especially those that are conductive such as polyacetylene, polythiophene and the like. The conductive layer may be thick or only several molecular layers in depth as the application requires. The conductive layer may be comprised of an evaporated thin metal layer or an epitaxial layer of gallium arsenide or other semiconductor materials rendered conductive through known semiconductor processing techniques. In addition, the conductive layer may be derivatized, the process by which is well known, e.g., see Kumar et al., "Patterned Self-Assembled Monolayer and Mesoscale Phenomena," *Accounts of Cemical Research*, 28:219–226 (1995).

The conductive layer is additionally fabricated from materials and having a morphology which is conducive to facilitate molecular binding. Ligands may bind directly, indirectly through other molecular structures, or through both configurations to bind to the conductive layer. The range of molecules that may bind to the conductive layer include but are not limited to proteins, nucleic acids, small molecules, saccharides, lipids, and any other molecule of interest. The chemistry may involve only a single species of molecules attached to the surface, a whole array of different species attached to the surface, or multiple binding events between species directly attached to the surface and ligands of interest in the solution.

The typical chemistry involved in attaching a ligand to the conductive layer will in general depend on the nature of the ligand and any antiligand to which it binds, and their functions in the assay. A list of possible types of interactions that may occur on the surface include but are not limited to: Protein/protein interactions, DNA/protein interactions, RNA/protein interactions, nucleic acid hybridization, including base pair mismatch analysis, RNA/RNA interactions, tRNA interactions, Enzyme/substrate systems, antigen/antibody interactions, small molecule/protein interactions, drug/receptor interactions, membrane/receptor interactions, conformational changes in solid phase ligands, protein/saccharide interactions, and lipid/protein interactions.

The actual surface chemistry may be described in one embodiment as primary binding and secondary binding. Additional layers of molecular binding may also occur. Primary binding refers to the attachment of an antiligand to the conductive surface, which can be done through the assistance of a linker molecule. Secondary binding refers to the binding of a ligand to the antiligand, which may be another molecule in the MBL or directly to the conductive surface itself. Typically, the binding involves a liquid phase ligand binding to an immobilized solid phase antiligand. For example, primary binding could be the attachment of a specific antibody to the conductive layer of the bioassay device and secondary binding would involve the binding of a specific antigen in a sample solution to the antibody. Alternatively, secondary binding may be the direct attachment of a protein to the conductive surface, such as the amine terminus of a protein attaching directly to a gold conductive layer.

Figure 1D:
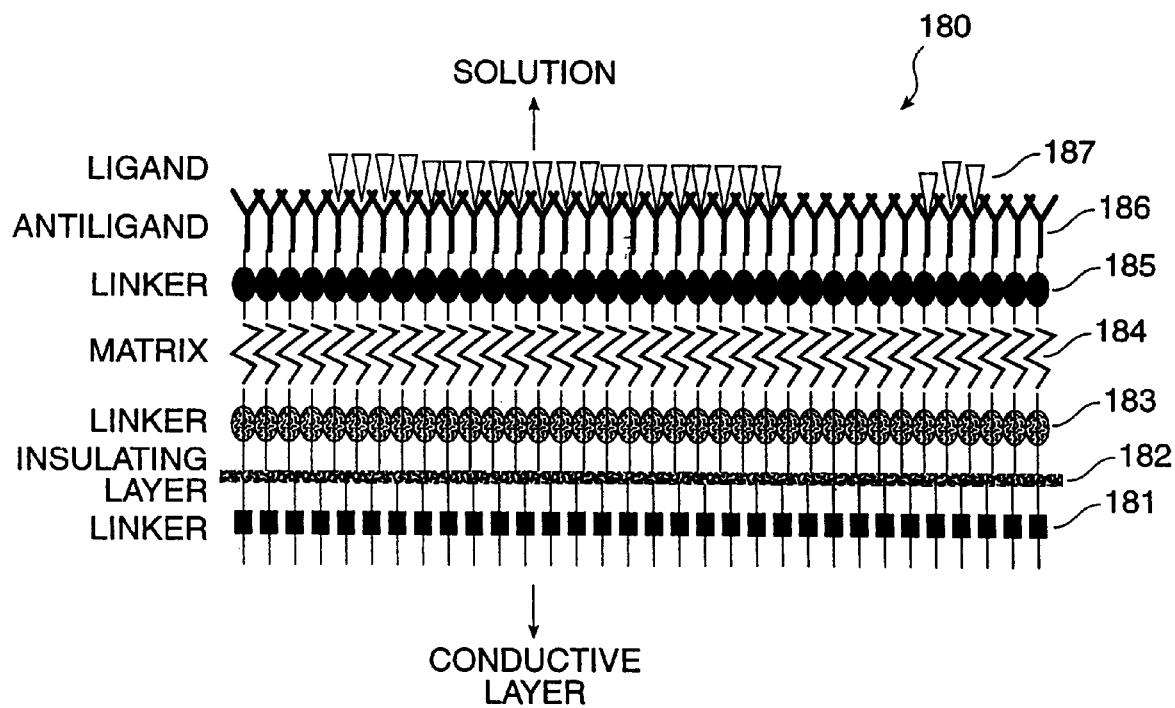
FIG. 1D illustrates one embodiment of a molecular binding layer in accordance with the present invention.

The aforementioned binding results in the formation of a molecular binding layer (MBL) 180 along one or more areas of the conductive layer, one embodiment of which is illustrated in FIG. 1D. In this embodiment, the MBL 180 optionally consists of a first linker 181, an insulator 182, a second linker 183, a matrix 184, a third linker 185, an antiligand layer 186, and a ligand layer 187.

First linker 181 provides attachment between insulating layer 182 and conductive layer (not shown). First linker 181 consists of molecule such as thiols, amines, amides, or metals such as chromium or titanium. Insulating layer 182 provides a barrier between the conductive layer and the MBL 180 and solution (not shown). Insulating layer 182 may provide a hermetic barrier to prevent structural deterioration of conductive layer due to exposure to the MBL and/or solution. Alternatively, or in addition, insulating layer 182 may consist of an electrically non-conductive material to prevent the flow of DC or low frequency energy from the conductive layer to the MBL and/or solution which could interfere with the measurement. The insulating layer may include polyimide, alumina, diamond, sapphire, non-conductive polymers, semiconductor insulating material such as silicon dioxide or gallium arsenide or other materials which provide hermetic and/or electrically insulating characteristics. The insulating layer may also consist of air, or another gaseous substance, in which case linker 181 may be deleted.

Second linker 183 provides attachment between the insulating layer 182 and matrix 184 and consists of the same or similar molecules as first linkers 181. Matrix layer 184 may consist of a polymer layer, but is also optionally a carbohydrate, protein, poly-amino acid layer or the like. Third linker 185 consists of molecules suitable for attaching the matrix layer to the antiligand 186 and may consist of the same or similar molecules as either first and/or second linkers 181 and 183.

Antiligand 186 is used to specifically or non-specifically bind the ligand 187 within solution and/or to measure physical properties of the solution, some examples of which are temperature, pH, ionic strength, and the like. Antiligand consists of a molecule or molecular structure which specifically or nonspecifically binds to ligand 187. For instance, in the case in which the ligand consists of an antigen, antiligand 186 will consist of an antibody. Ligand 187 consists of a molecule or structure which specifically or nonspecifically binds to the antiligand 186.

Generally, the MBL will be sufficient to interact measurably as described herein with an electromagnetic test signal along the associated signal path. Thus, essentially any MBL composition that exhibits varying dielectric properties can be analyzed. In most embodiments, the MBL will range in thickness between about 1–5 Å to 1 cm. For simple molecular binding events, the range will be usually between about 10 Å to 10,000 Å, typically between 100 Å and 5,000 Å, or 500 Å to 1,000 Å. In larger interactions (e.g. cellular) the MBL will range between 1 $\mu$m and 100 $\mu$m, preferably 5 $\mu$m to 50 $\mu$m. With insulators, matrices and the like, the size will range significantly higher.

The embodiment of FIG. 1D is not intended to be exhaustive of all possible MBL configurations. Those of skill in the art will appreciate that a vast multiplicity of combinations making up the MBL can be designed, as dictated by the specific applications. For instance, first, second and third linkers 181, 183, 185, insulating layer 182, and matrix layer 184 are not implemented and the MBL consists of antiligand 186 and ligand 187. Further alternatively, first linker 181 and insulating layer 182 may be deleted. Other alternative embodiments in which one or more of the described layers are deleted, or additional layers added, will be apparent to one skilled in the art.

Figure 1E:
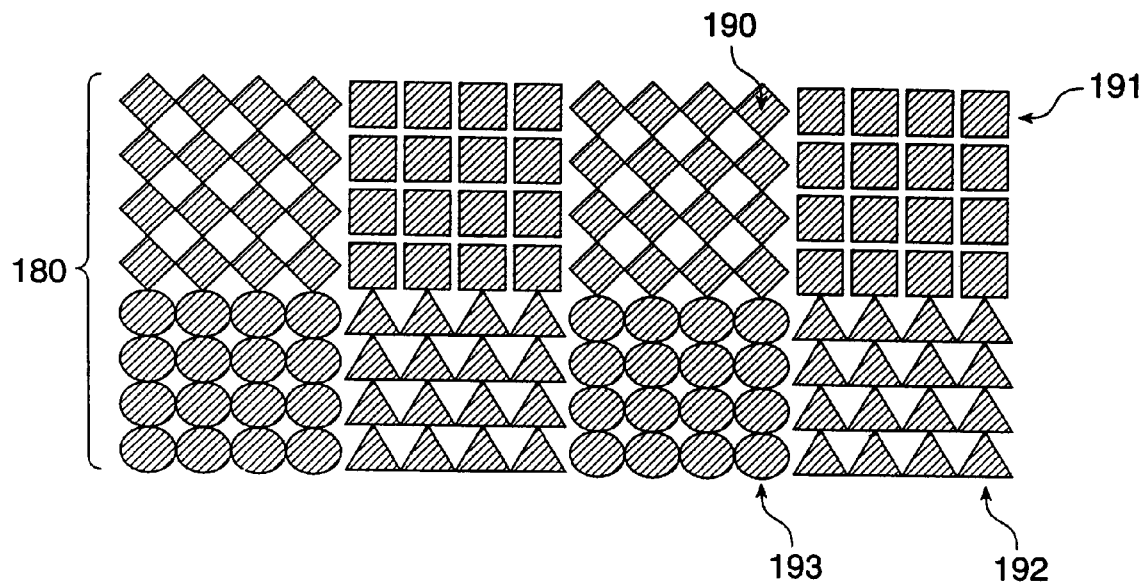
FIG. 1E illustrates one embodiment of a molecular binding layer having multiple antiligands which are spatially separated in accordance with the present invention.
Figure 1F:
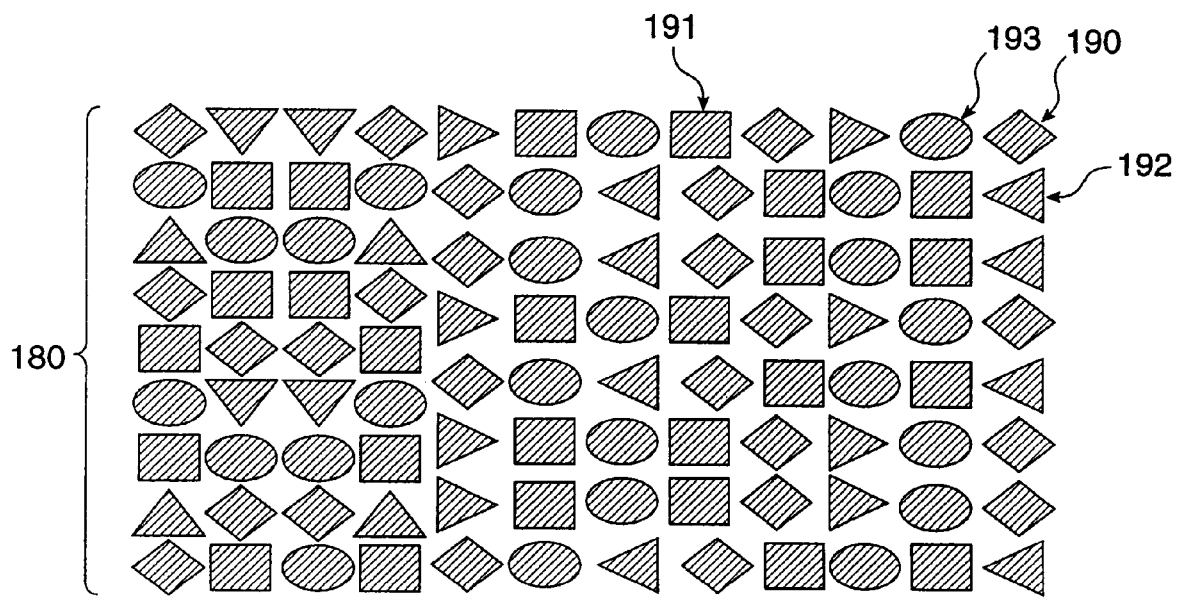
FIG. 1F illustrates one embodiment of a molecular binding layer having multiple classes of anitligands in accordance with the present invention.
Figure 1G:
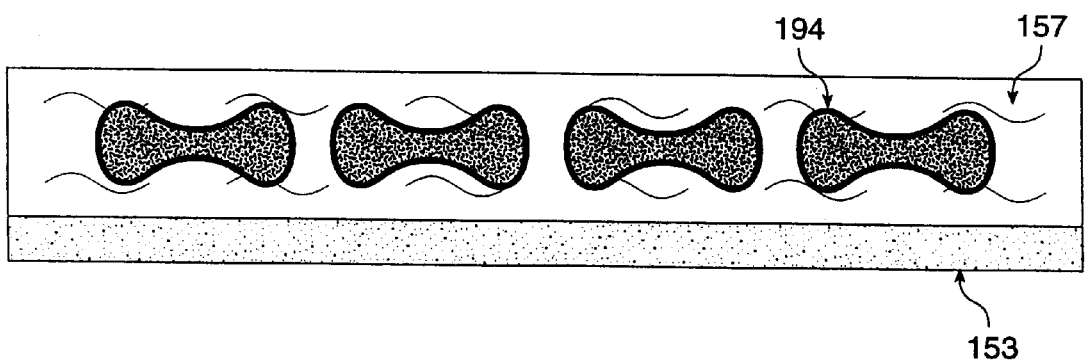
FIG. 1G illustrates a molecular binding layer comprising one or more cells in accordance with the present invention.
Figure 1H:
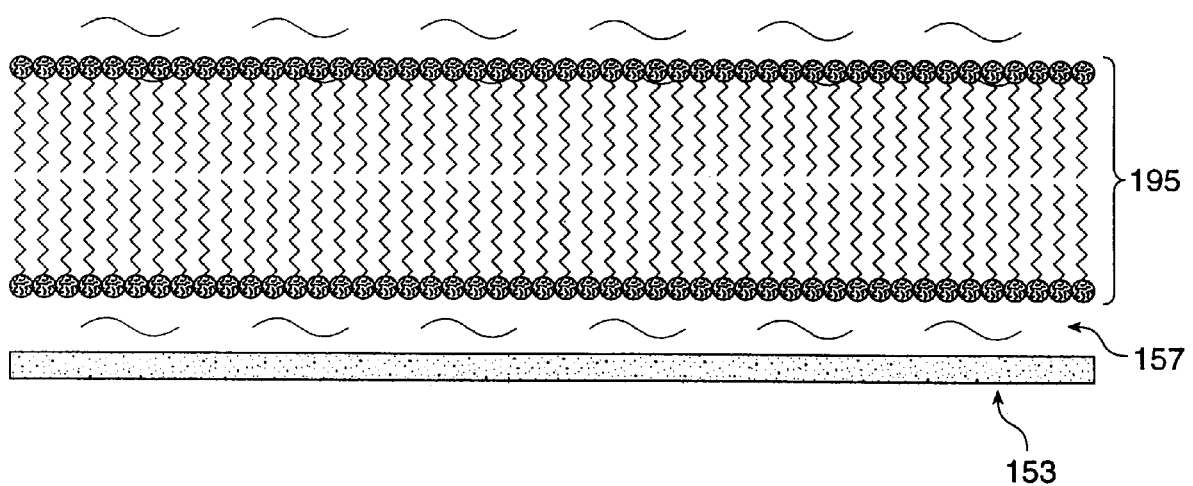
FIG. 1H illustrates a molecular binding layer comprising cell membranes and membrane associated structures in accordance with the present invention.

Further, the MBL may be composed of heterogeneous molecules which may be spatially grouped or randomly layered or distributed depending upon the particular array format. For example, FIG. 1E illustrates a top view of an MBL 180 having four different antiligands 190, 191, 192 and 193, which are spatially separated. FIG. 1F illustrates an MBL 180 in which four different antiligands 190, 191, 192 and 193 are randomly distributed throughout. In another embodiment, FIG. 1G illustrates a cross-sectional view in which the MBL 180 contains cells 194 in solution 157 coupled to signal path 153. In another embodiment, a cell membrane 195, with membrane bound structures (not shown), is in solution 157 coupled to signal path 153. The layers may include for example, linkers, matrices, antiligands, ligands and one or more insulating layers. In some embodiments, one or more membranes may be employed, such as those controlling ion transport, size or charge selection or supporting the attachment of antiligand or other molecular structures.

Electrically, the MBL exhibits unique dielectric properties which are in part attributable to the structural and conformational properties, and changes therein, of bound molecules, both isolated and in the presence of environmental changes such as binding events, pH changes, temperature, ionic strength and the like. The dielectric properties of the bound molecular structures, along with the local structures of the solvating medium (the solution) may also be attributable to changes in the intramolecular and intermolecular bonds caused by primary or other higher-order binding, and the displacement of the solvating medium near the conductive layer.

Once a conductive layer is provided, one of skill in the art will be generally familiar with the biological and chemical literature for purposes of selecting a system with which to work. For a general introduction to biological systems, see, *Current Protocols in Molecular Biology*, F. M. Ausubel et al., eds., Current Protocols, a joint venture between Greene Publishing Associates, Inc, and John Wiley & Sons, Inc. (through 1997 Supplement) (Ausubel); Watson et al. (1987) *Molecular Biology of the Gene, Fourth Edition*, The Benjamin/Cummings Publishing CO., Menlo Park, Calif.; Alberts et al. (1989) Molecular Biology of the Cell, Second Edition Garland Publishing, N.Y.; *The Merck Manual of Diagnosis and Therapy*, Merck & Co., Rathway, N.J. Product information from manufacturers of biological reagents and experimental equipment also provide information useful in assaying biological systems. Such manufacturers include, e.g., the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Aldrich Chemical Company (Milwaukee, Wis.), GIBCO BRL Life Technologies, Inc, (Gaithersberg, Md.), Fluka Chemica-Biochemika Analytika (Fluka Chemie AG, Buchs, Switzerland, Applied Biosytems (Foster City, Calif.), as well as many other commercial sources known to one skilled in the art.

Biological samples can be derived from patients using well known techniques such as venipuncture, lumbar puncture, fluid sample such as saliva or urine, or tissue biopsy and the like. When the biological material is derived from non-humans, such as commercially relevant livestock, blood and tissue samples are conveniently obtained from livestock processing plants. Similarly, plant material used in the invention may be conveniently derived from agriculture or horticultural sources, and other sources of natural products. Alternatively a biological sample may be obtained from a cell or blood bank where tissue and/or blood are stored, or from an in vitro source, such as a culture of cells. Techniques for establishing a culture of cells for use as a source for biological materials are well known to those of skill in the art. Freshney, *Culture of Animal Cells, a Manual of Basic Technique, Third Edition*, Wiley-Liss, N.Y. (1994) provides a general introduction to cell culture.

The present invention can be practiced in a number of embodiments. Some are detailed below, additional embodiments and applications are detailed in the applications section.

In one embodiment, the invention is used to detect binding of a molecular structure to the signal path. In this embodiment, a signal is propagated along the signal path. As it propagates, it couples to the bound structure and is modulated. Analysis of the modulated response indicates binding.

In another embodiment, the invention may be used to identify secondary binding. For example, primary binding may be the attachment of an antibody to the conductive surface. Secondary binding might involve the measurement of binding between the immobilized antibody and its antigen in solution. After primary binding has been detected as described in the previous paragraph, the solution containing the antibody is added to the bio-assay device and the response measured again. The response is compared to the primary binding response. A change would indicate that a binding event has occurred.

In one aspect, the present invention may be used to identify ligands, for example proteins, in the primary binding stage. In the calibration phase the responses of a large number of known proteins can be determined and stored. After attaching an unknown protein to the assay surface, the dielectric properties of the system could be measured and the dielectric properties of the signal used to identify the protein on the surface. Because each protein's fingerprint response is stored, the unknown response can be compared with the stored responses and pattern recognition may be used to identify the unknown protein.

In another embodiment, the invention may be used in an array format. The device will have multiple addressable sites, each of which has bound to it a specific antiligand. After delivering solution to the device, binding responses at each site will be measured and characterized. A device of this type may be used to measure and/or identify the presence of specific nucleic acid sequences in a sample. At each of the addressable sites a unique nucleic sequence is attached as the antiligand. Upon exposure to the sample, complementary sequences will bind to appropriate sites. The response at each site will indicate whether a sequence has bound. Such measurement will also indicate whether the bound sequence is a perfect match with the antiligand sequence or if there are one or multiple mismatches. This embodiment may also be used to identify proteins and classes of proteins.

In another embodiment, this invention may be used to generate a standard curve or titration curve that would be used subsequently to determine the unknown concentration of a particular analyte or ligand. For example, an antibody could be attached to the device. The device could be exposed to several different concentrations of the ligand and the response for each concentration measured. Such a curve is also known to those skilled in the art as a dose-response curve. An unknown sample can be exposed to the device and the response measured. Its response can be compared with the standard curve to determine the concentration of the ligand in the unknown sample.

In another embodiment, this invention may be used to internally self-calibrate for losses due to aging and other stability issues. For example with antibody-antigen systems, this invention allows one to measure the amount of active antibody on the surface by measuring a primary response before exposure the unknown. The value of the primary response is used to adjust the secondary response, antigen binding, by a constant that reflects the amount of active antibody that remains on the device.

III. The Bio-Assay Device

A. Device Structure

Structurally, the bio-assay device includes a signal path and a bio-electrical interface. The signal path may consist of a single input/output signal port; one input signal port path and one output port path, or multiple input and/or output signal port paths. The signal path(s) may be realized in a number of different architectures, such as a conductive wire, a transmission line, a waveguide structure, resonant cavity, or any other transmission medium that will support the propagation of the test signal over the desired frequency range. For possible embodiments, see R. E. Collins *Foundations for Microwave Engineering*, McGraw-Hill Publishing Co., 1966; and S. March, *Microwave Transmission Lines and Their Physical Realizations*, Les Besser and Associates, Inc., 1986. Further, the bio-assay device may also be realized in a variety of different configurations. Non-exhaustive configurations include large to miniaturized structures using conventional manufacturing techniques, conventional etching and photolithography, or semiconductor processing techniques.

Figure 2A:
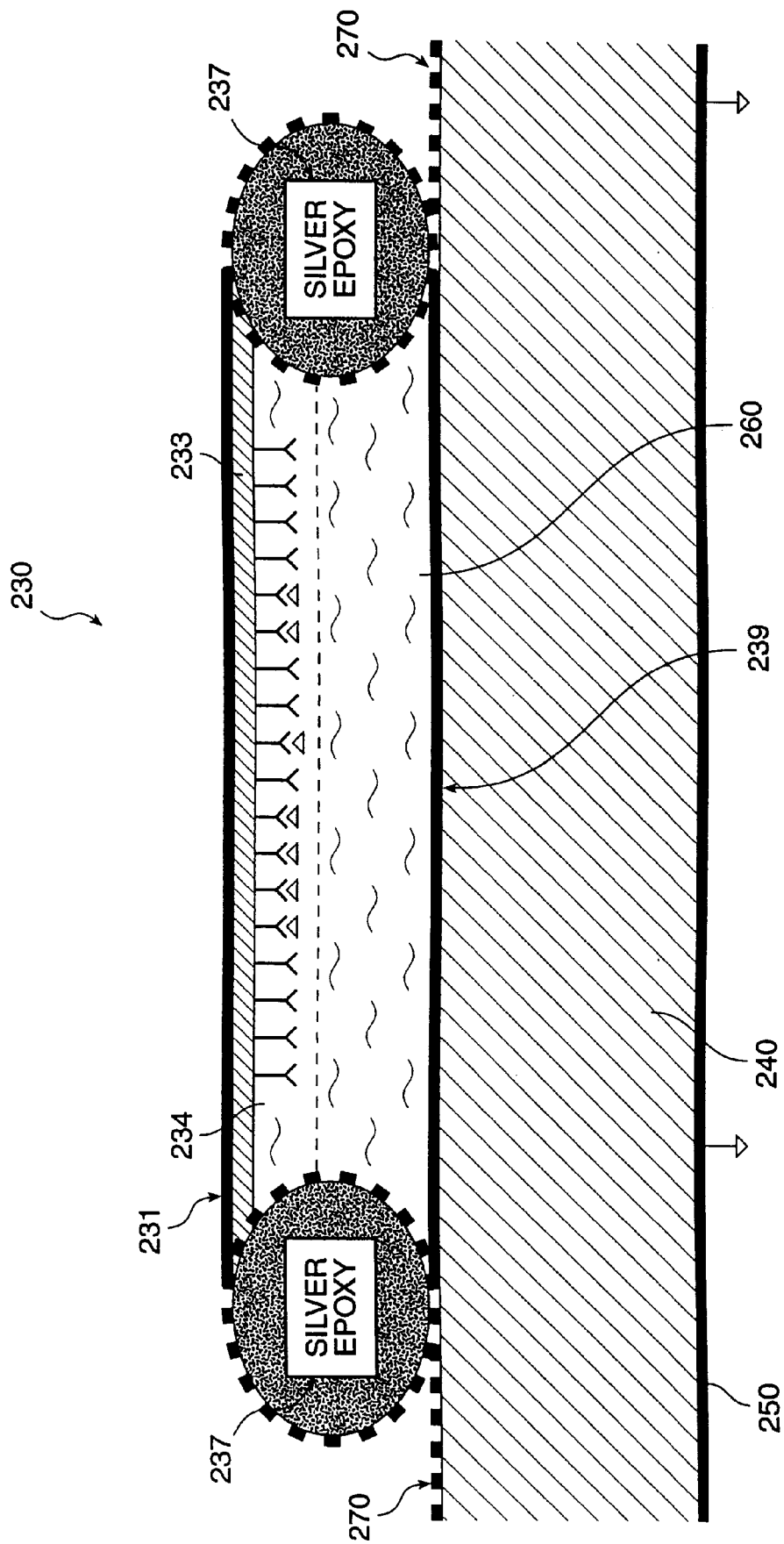
FIG. 2A illustrates one embodiment of the bio-assay device in accordance with the present invention.

FIG. 2A illustrates one embodiment of the bio-assay device as shown in cross-sectional view. The bio-assay device 230 consists of a top plate 231, contact terminals 237, and a bottom plate 239. Top plate 231 includes a bottom surface having an interface transmission line 233 disposed thereon. The dielectric substrate 240 and the ground plane 250 are located external to the bio-assay device. Top plate 231 and/or dielectric substrate 240 are formed from an insulating material, such as glass, which are preferably compatible with conventional photolithography or gold sputtering, etching or chemical vapor deposition (CVD) processing. Other materials such as alumina, silicon, gallium arsenide or other insulating materials, may alternatively be used.

As illustrated in FIG. 2A, the bottom surface of the interface transmission line 233 is in contact with the molecular binding layer (MBL) 234. As illustrated, the MBL may consist of bound molecular structures of different layers or types as well as molecular structures occurring within the solution. In alternative embodiments, the MBL 234 may extend over small or large portions of the interface transmission line 233 and may consist of different bound molecular structures as shown. The MBL may consist solely of antiligand/ligand structures, or a variety intermediate of linker, matrix, and insulating layers, as shown in FIG. 1D. When implemented, the insulating layer 182 (FIG. 1D) may consist of air, polyimide, alumina, diamond, sapphire, or semiconductor insulating material such as silicon dioxide or gallium arsenide or a non-conductive material in addition to other conventional insulating materials. The thickness and dielectric constant of the insulating layer are such that the MBL 234 and the interface transmission line 233 are tightly coupled together during signal transmission. The thickness of the insulating layer 182 may be $10^{-1}$ m, $10^{-2}$ m, $10^{-3}$ m, $10^{-4}$ m, $10^{-5}$ m, $10^{-6}$ m, $10^{-7}$ m, $10^{-8}$ m, $10^{-9}$ m, $10^{-10}$ m or less in thickness, or values ranging therebetween, depending the amount of coupling required, the dielectric constant of the insulating layer, and the total coupling area. Coupling may be accomplished through a number of different configurations, including broadside and offset coupled configurations in multi-layer, coplanar, or waveguide circuit topologies. Implementing an insulating layer may be advantageous for hermetically sealing the interface transmission line from the solution medium and/or for preventing DC or low frequency current from flowing into the solution which could possibly disrupt molecular binding events occurring therein.

The interface transmission line 233 consists of a material which is capable of supporting signal propagation and which is capable of binding the MBL 234. The material will vary depending upon the makeup of the MBL, but some will include gold, indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof. Alternatively, the interface transmission line 233 may include one or more molecular structures (antiligands) (which forms a part of the MBL 234) for forming bonds with one or more targeted molecules (ligands). The material comprising the interface transmission line may also be chosen to promote the attachment of linkers as well as to support signal propagation. Other materials that can be used to form the interface transmission line 233 will be readily apparent to those of skill in the art.

The ligands may be transported to the MBL 234 using a solution 260, such as Dulbecco's phosphate-buffered saline (d-PBS) for example. The protein, nucleic acid, or other ligand of interest can be applied to the binding surface using a variety of techniques such as wicking, pipeting, dipping, dropping, direct contact, or through capillary action.

In a specific embodiment, the interface transmission line 233 is designed to provide low signal loss and close impedance matching to the external transmission lines 270. Low signal loss is achieved by fabricating the interface transmission line 233 from a conductive material, some examples being gold, copper, aluminum, indium tin oxide (ITO) or other conductive materials described above. Close impedance matching is achieved by defining the width of the interface transmission line 233 at approximately the width of external transmission lines 270, depending on the relative dielectric properties of the substrate, the solution, and the MBL. Signal continuity between the interface transmission line 232 and the external transmission lines 270 is provided via contact terminals 237. As explained above, the MBL 234 and solution medium 260 may be located proximate to the ground plane 250 alternatively, or in addition to these layer's location proximate to the interface transmission line 232.

Additional analog and/or digital circuitry in lumped element form, distributed form, or a combination of both may be included at the input and/or output ports of the bio-assay device. For instance, impedance matching circuits and/or buffer amplifier circuits may be employed at the input port. Alternatively, or in addition, impedance matching circuitry and one or more output amplifiers may be implemented to further enhance the output signal. Those of skill in the art of electronics will appreciate that other types of conditioning circuitry may be used in alternative embodiments as well.

Figure 2B:
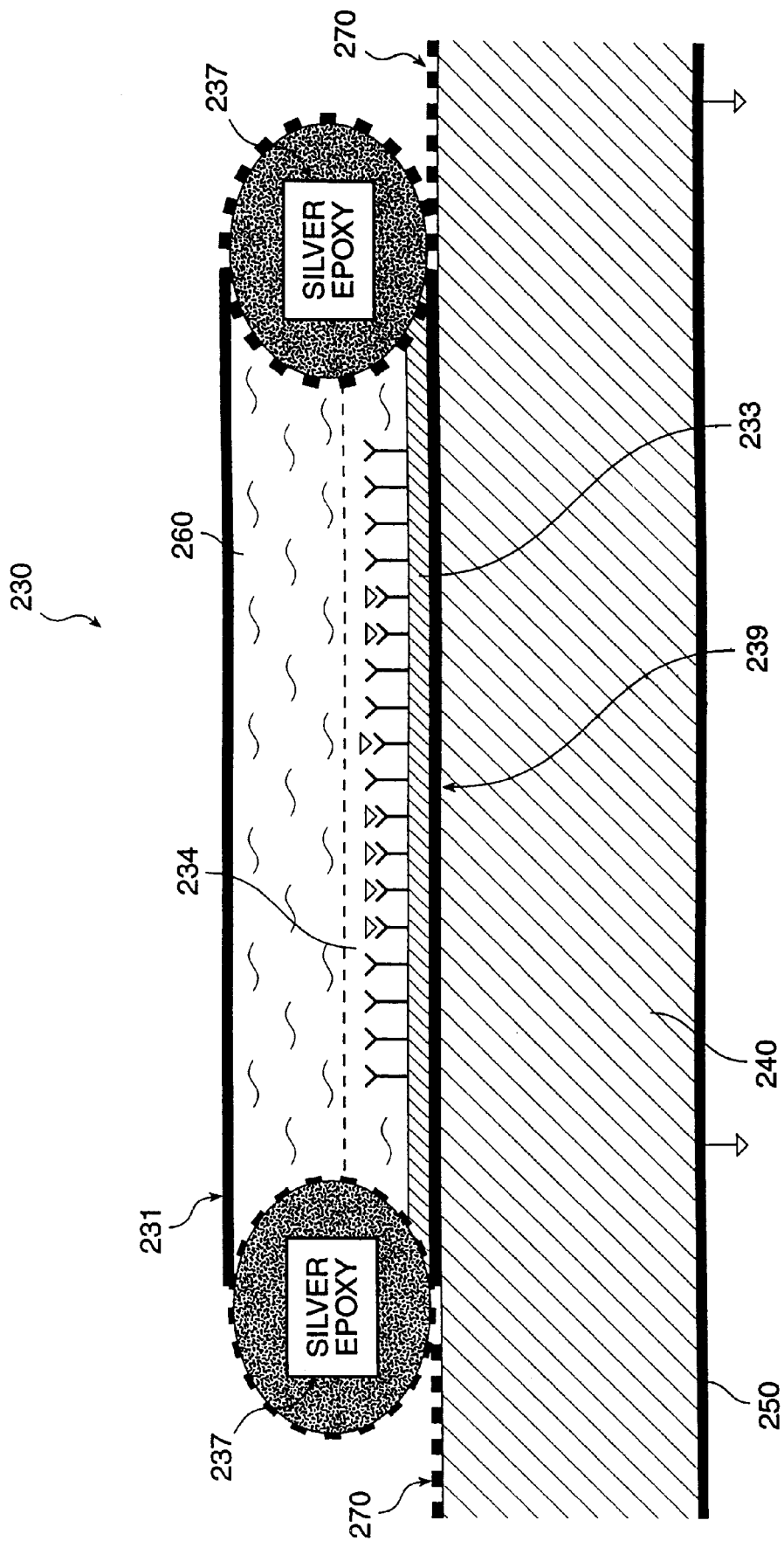
FIG. 2B illustrates a second embodiment of the bio-assay device in accordance with the present invention.

FIG. 2B illustrates a second embodiment of the bio-assay device. In this embodiment, the solution occupies a space above the interface transmission line 233 which is formed on the top surface of bottom plate 239. The top side of the interface transmission line 233 forms the binding surface to which the MBL 234 adheres. Dielectric layer 240 is positioned between interface transmission line 233 and the ground plane 250. Contact terminals 237 provide a signal path to the external transmission lines 270. The interface transmission line, top plate, bottom plate, contact terminals, and dielectric layer may be formed from the materials and the processes as described above. The MBL may also be configured as described above in FIG. 1D, or variations thereof. Further, the MBL 234 and solution medium 260 may be located proximate to the ground plane 250 alternatively, or in addition to these layer's location proximate to the interface transmission line 233.

Additional structural embodiments include bio-assay devices having multi-element transmission lines, waveguides, and resonant cavities, in which the MBL may be attached to one or more of the line or cavity elements in such a way as to enhance detection specificity and sensitivity. Examples of such structures include parallel arranged signal combiners, resonant cavities, or waveguides along which the bound MBL on one element alters the signal propagation properties as compared to another parallel element without the bound structure, and thus serve to change the mode properties of the combined signal, resulting in readily detectable output signal properties. These latter effects make use of well-known techniques to measure frequency, frequency stability, and very small changes in the frequency with ultra-high precision.

B. Binding Surface Chemistry

Figure 3:
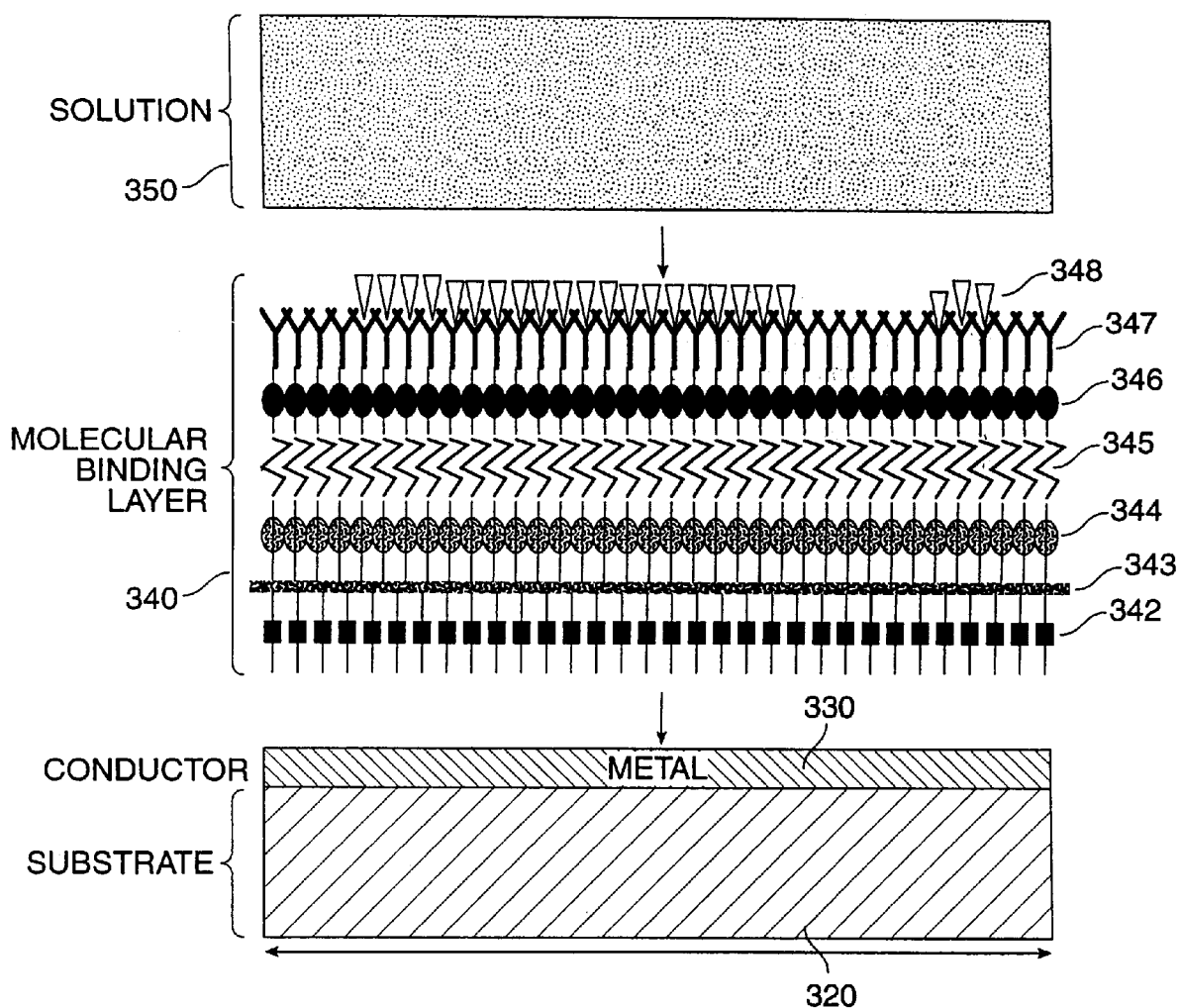
FIG. 3 illustrates one embodiment of the binding surface chemistry which occurs along the conductive layer of the bio-electrical interface.

FIG. 3 illustrates one embodiment of the binding surface chemistry which occurs along the conductive layer of the bio-electrical interface. The bio-electrical interface includes a substrate 320, a conductive layer 330, a MBL 340, and solution 350. The substrate 320 may be any of the dielectric layer or substrate materials described herein including alumina, diamond, sapphire, plastic, glass and the like and may provide structural support to the conductive layer 320. In an alternative embodiment, substrate 320 is removed and structural support is provided via insulating layer 342.

The conductive layer 330 consists of a material and morphology which will promote signal propagation over the desired frequencies and which will promote binding of the MBL 340, as described above. In a two-conductor circuit topology, conductive layer 330 may comprise the signal plane or the ground plane. In either case however, a second conductive layer (either the signal plane or the ground plane, not shown) is located either below the substrate 320 (the arrangement of FIG. 2B) or at least one substrate layer removed from the solution 350 (an inverted arrangement of FIG. 2A). Alternatively, conductive layers may be positioned at both of these levels.

Solution 350 is coupled to the MBL 340 for permitting the flow of ligands to the MBL 340. Ligand flow from solution 350 to MBL 340 may be directionally or non-directional. Solution consists of any transporting medium such as gases, ligius, or solid phase materials, some examples being aqueous d-PBS, Tris buffer, phosphate buffers, and the like.

Along the bio-electrical interface, the MBL is positioned between at least a portion of the solution and the signal path, such that the MBL is more proximate to the signal path than the solution along that portion. In the embodiment of FIG. 3, the MBL 340 is positioned between the solution 350 and the conductive layer 330, closer in proximity to the latter. In one embodiment (shown in FIG. 2A), the solution is positioned between the signal and ground planes. In a second embodiment (shown in FIG. 2B), the solution is positioned outside of the signal-ground plane region.

The typical chemistry involved in binding the MBL to the conductive surface will in general depend on the nature and content of the MBL and its function in the assay. The MBL may consist of a ligand, ligand/antiligand complex, or other molecular structures as described herein. Typically, the ligand will be functionally intact, as close to the surface as possible, and the surface density of the antiligand will be high enough to provide the greatest dielectric effect, but not so high as to impair the function of binding, such as by steric hindrance or physically blocking the active binding site of the immobilized antiligand by neighboring molecules.

Ligands may bind specifically or non-specifically either directly to the conductive layer 320 or intermediate structures as shown in FIG. 3. If specifically bound ligands are desired, a linker is optionally used to facilitate the binding, for example to bind all proteins such that conductive layer 320 is exposed to solution. To ensure a densely pack binding layer, thiol groups, Fab, or proteins such as protein A may be used to facilitate the binding of antibodies or other antiligands along the conductive layer 320. These and similar substances may be applied to the conductive layer 320 in a number of ways, including photolithography, semiconductor processing, or any other conventional application techniques.

In addition, some ligands and antiligands may be able to bind in multiple ways. These ligands typically have a statistically predominant mode of binding or may be engineered to bind in a site-specific way. Some antiligands optionally bind the surface in a site-specific manner. For example, an oligonucleotide might be bound at one terminus. Genrally, the antiligand will be attached in a manner which will not impair the function of the antiligand, e.g., preferably at concentrations that minimize surface denaturation.

The concentration of the antiligand on the binding surface will vary, depending upon the specific analyte. For example, typical concentrations for proteins are $10^7/cm^2$, $10^8/cm^2$, $10^9/cm^2$, $10^{10}/cm^2$, $10^{11}/cm^2$, $10^{12}/cm^2$, $10^{13}/cm^2$, $10^{14}/cm^2$, $10^{15}/cm^2$, or concentrations ranging therebetween. Typical concentrations for nucleic acids are $10^7/cm^2$, $10^8/cm^2$, $10^9/cm^2$, $10^{10}/cm^2$, $10^{11}/cm^2$, $10^{12}/cm^2$, $10^{13}/cm^2$, $10^{14}/cm^2$, $10^{15}/cm^2$, $10^{16}/cm^2$, $10^{17}/cm^2$, $10^{18}/cm^2$, $10^{19}/cm^2$, $10^{20}/cm^2$, or concentrations ranging therebetween Typical concentrations for analytes in whole blood range from 55 M, 25 M, 10 M, 1 M, 0.5 M, $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, $10^{-16}$ M, $10^{-17}$ M, $10^{-18}$ M, or concentrations ranging therebetween.

Enough ligand should adhere within the MBL to alter the transmission of a signal through the bio-electrical interface. The quantity of ligands adhering to the binding surface may consist of 1, 10, $10^2$, $10^3$, $10^4$, $10^5$, $10^6$, $10^7$, $10^8$, $10^9$, $10^{10}$, $10^{11}$, $10^{12}$, $10^{13}$ or more ligands, as well as any number therebetween depending upon the surface area of the conductive layer. The ligands need not be applied in predefined regions along the conductive layer since the signal responses are determined by inherent dielectric properties of the MBL as opposed to placement on the bio-assay device or chip. The MBL will generally have a surface density for smaller molecules ranging from $10^{10}$ cm$^2$ to $10^{24}$ cm$^2$, typically $10^{15}$ cm$^2$ to $10^{20}$ cm$^2$. The ligand layer may be as thin as 1 layer, but 2, 3, 4, 5 or 10 or more layers are optionally used.

Once a ligand is bound to the conductive layer, the chemistry and/or structural biology of the system comes into play. The ligand's dielectric properties yield a signal response which is characteristic of the bound structure(s), thereby permitting binding event detection, as well as detection of other properties of interest in the structure. The unique response provided by the binding event will depend on the immobilized antiligand, its target ligand, and the rearrangement of the nearby solution molecules (such as water and free ions). The range of molecules that can bind to the surface include but are not limited to proteins, nucleic acids, small molecules, saccharides, lipids, and any other molecule of interest.

Typically, the molecules of the MBL are disposed within a solution which may consist of an aqueous solution of water, d-PBS, Tris, blood, physiological buffer, cerebrospinal fluid, urine, sweat, saliva, other bodily secretions, organic solvents, and he like. Other solutions may include gases, emulsions, gels, and organic and inorganic compounds The secondary binding reaction occurs at the MBL of the bio-assay device. A ligand in a solution is transported across the bio-assay device such that it contacts the antiligand of the binding layer. The concentration of the ligand in the solution varies and may consist of $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, $10^{-16}$ M, $10^{-18}$ M, $10^{-19}$ M, $10^{-20}$ M. When an interaction, such as binding, occurs between the ligand and the antiligand, the ligand, then optionally becomes part of the binding layer, as dictated by the chemical equilibrium characteristics of the binding event.

The MBL includes the bound ligands and may also include solution molecules. The bound ligands can be any molecule, including proteins, carbohydrates, lipids, nucleic acids, and all other molecules discussed herein. The MBL may further include a linker to aid in the binding of the antiligand to the binding surface layer.

Additionally, the interaction of the antiligand with the ligand changes the characteristic dielectric response of the binding layer with only the antiligand attached. For example, if antiligand A is the antiligand that forms the binding layer, the dielectric response of a test signal propagating along the transmission line will reflect the characteristic properties of the structure of antiligand A. When ligand B binds to antiligand A, the structure and/or dielectric properties of the binding layer will change due to the binding of A to B. The structure of A may change as B binds to it, thus providing a different signal response. The change in signal due to the binding interaction will be characteristic of the binding of A to B. Therefore, the presence of a binding interaction can be determined from the change in the signal.

Moreover, information about the type of bond or the structural and/or conformational changes upon binding is obtained by noting which parts of the signal response have changed due to the interaction. Ligand B is optionally detected and identified by the signal change upon its binding to antiligand A. The binding of ligand B to antiligand A induces a conformational change, or other change in the molecular structure or surrounding solution, in antiligand A and its environs. These changes alter the dielectric properties of the MBL, thereby altering the signal response of the test signal propagating along the signal path. The change in the test signal can be used to detect the ligand B binding event and the particulars of the change can be used to identify the ligand B. In as much as the relationship between structure and function of the molecule is known, for example in the case of enzymes, antibodies, receptors and the like, the function of the bound ligand can be deduced from its spectral identification.

In one embodiment, one type of antiligand is applied to the binding surface to form a MBL, and a ligand is applied across the MBL to detect a binding event between the two molecules. In another embodiment, the antiligand may be a mixture and the ligand that is applied across the binding layer is a known analyte or antibody. By detecting specific changes in the signal response, the particular ligand with which the antiligand interacted can be determined due to conformational and other changes induced in the ligand or antiligand, and the spectral response resulting therefrom. Such an embodiment does not require the spatial isolation of each of the specific antiligands, but rather derives the desired level of specificity from the spectral response, so that a given binding interaction is determined by looking at the electromagnetic response rather that noting on which part of the assay the binding event took place.

In another embodiment, the antiligand may be a known molecule on the binding layer and the ligand applied across the bio-assay device as a mixture of unknowns, such as a whole blood sample. In this case, the presence of a particular ligand such as an antibody in the blood is detected by the presence or absence of a particular peak or signal in the spectrum that results from passing a signal through the bio-assay device. Alternatively it can be detected due to the changes in the spectrum of the antiligand or ligand upon binding of the ligand. Such an embodiment increases the specificity of the detection over that of the binding chemistry alone, since the signal contains information about the nature of the binding event. Thus, specific binding may be distinguished over non-specific binding, and the overall specificity of detection may be greatly improved over the specificity of the chemistry alone.

The system of detection formed through use of the bioassay device provides a high throughput detection system because detection optionally occurs in real time and many samples can be rapidly analyzed. The response period is optionally monitored on a nanosecond time scale. As soon as the molecules are bound to each other, detection occurs. More time is optionally required to measure low concentrations or binding events between molecules with a low binding affinity. The actual time is optionally limited by diffusion rates. Other than these potential limitations, thousands of compounds are optionally run through the system very quickly, for example, in an hour. For example, using chip fab technologies, a 10,000 channel device (using some of the emerging microfluidics technologies) is possible, and with small volumes and thus short diffusion times, and kinetic measurements measuring only the beginning of the reaction, 10 million samples per hour are optionally measured. With known concentrations, the binding affinity is optionally calculated from the kinetics alone and thus the device can be probed at a very fast time scale and the affinity calculated and/or estimated from the slope of the kinetic curve. References for kinetics and affinities can be found in any standard biochemistry or chemistry text such as Mathews and van Holde, *Biochemistry*, Benjamin Cummings, New York, 1990.

C. Bio-Electrical Interface

The bio-electrical interface is the structure along which the MBL and the signal path are formed. As described above, the signal path may consist of a conductive or dielectric waveguide structure, a two conductor structure such as a conventional signal/ground plane structure, or three or more conductor structures known in the art. Generally, the thickness of the conductive region of the signal path is designed to provide minimal signal loss. For example, a typical thickness of gold transmission line is in the order of 0.1 to 1000 $\mu$m, preferably about 1–10 $\mu$m.

The signal path is formed along a direction which is non-orthogonal to the MBL. In one embodiment, the test signal propagates in parallel to a tangent on the surface on which the MBL is formed. In other embodiments, the test signal may propagate at an angle of $\pm 1°$, $\pm 2°$, $\pm 3°$, $\pm 4°$, $\pm 5°$, $\pm 10°$, $\pm 15°$, $\pm 20°$, $\pm 30°$, $\pm 40°$, $\pm 45°$, $\pm 50°$, $\pm 60°$, $\pm 70°$, $\pm 80°$, or $\pm 85°$ relative to the MBL binding surface, or any ranges therebetween. In a first embodiment, the signal path consists of a transmission line in a two conductor structure and the direction of the signal path is defined by the Poynting vector as known in the art of electromagnetics. In a second embodiment, the transmission line may consist of a conductive region or layer which extends continuously along the bio-electrical interface region. In a third embodiment, the signal path maybe defined as the path having the least amount of signal loss along the bio-electrical interface over the desired frequency range of operation. In a fourth embodiment, the signal path maybe defined as having an a.c. conductivity of greater than 3 mhos/m, i.e., having a conductivity greater than that a saline solution, typically greater than 5 mhos/m, but ideally in the range of 100 to 1000 mhos/m and greater.

The operation of the bio-electrical interface will be better understood by developing an equivalent circuit model for the interface. The equivalent circuit models presented are shown in a two-conductor circuit topology, although those of skill in the art of circuit design will readily appreciate that each may be implemented in single conductor waveguide topologies, resonant circuit topologies, as well as circuit topologies with three or more conductors.

Figure 4A:
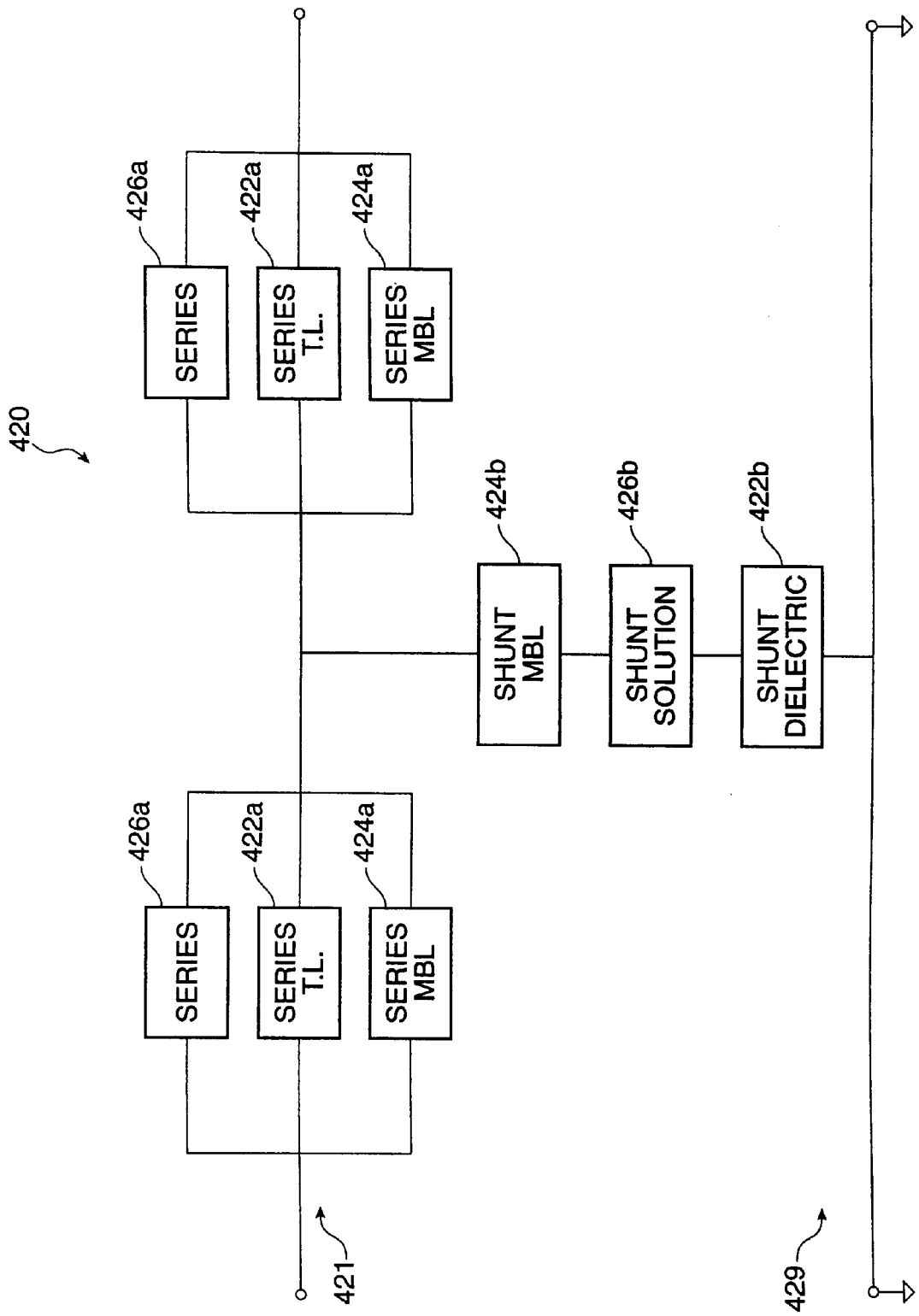
FIG. 4A illustrates one embodiment of an equivalent circuit model for the bio-electrical interface structure shown in FIG. 2A.

FIG. 4A illustrates one embodiment of an equivalent circuit model 420 for the bio-electrical interface structure shown in FIG. 2A. Those of skill in the art of circuit design will appreciate that the illustrated circuit model is not exhaustive and that other equivalent circuit models may be derived from the bio-electrical interface of FIG. 2A.

The illustrated equivalent circuit model includes series blocks 422a, 424a, and 426a which models the series electrical effects of the interface transmission line 232, the MBL 234, and the solution 260, respectively, all as shown in FIG. 2A. The interface transmission line, MBL, and solution circuit blocks 422a, 424a, and 426a are coupled in parallel since the interface transmission line, the MBL, and the solution, each provides a possible longitudinal signal path along the interface. In an alternative embodiment where the MBL and solution are located proximate to the ground plane, the interface transmission line and the ground planes of the equivalent circuit model 420 are switched. In the embodiments where the MBL and solution are located proximate to both the interface transmission line and the ground plane, FIG. 2A represents the top half of the equivalent circuit, the bottom half (ground plane) of which is identical if the same solution and MBL is used.

The equivalent circuit model 420 further includes shunt circuit blocks 422b, 424b, and 426b which models, respectively, the shunt electrical effects of the dielectric layer 240, the MBL 234, and the solution 260, shown in FIG. 2A. The series orientation of shunt blocks 422b, 424b, and 426b results from the physical arrangement of each of these elements, occurring serially from interface transmission line through the MBL, solution, and the dielectric layer, to the ground plane, the arrangement of which is shown in FIG. 2A.

Figure 4B:
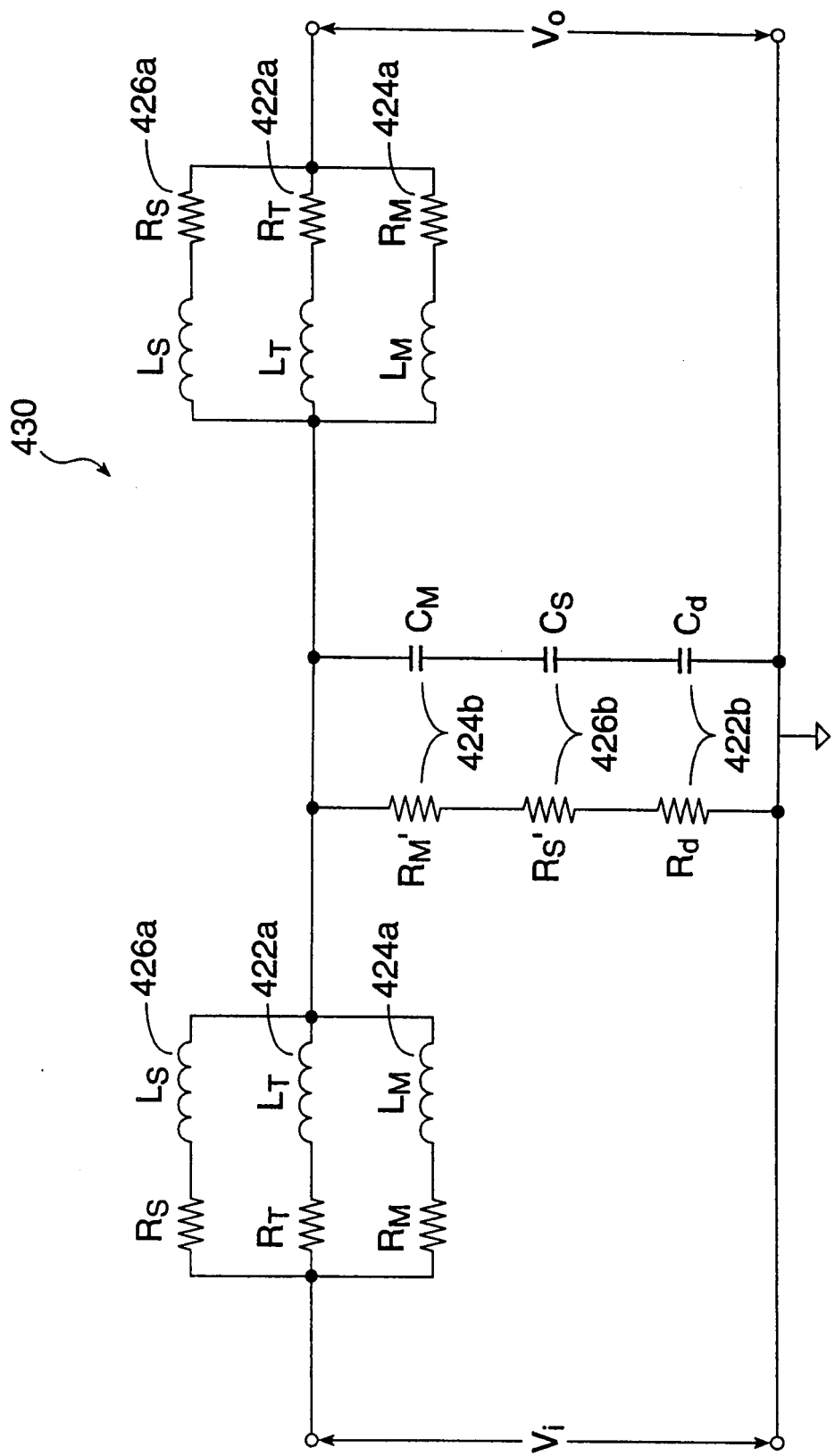
FIG. 4B illustrates one embodiment of a circuit corresponding to the equivalent circuit model shown in FIG. 4A.

FIG. 4B illustrates one embodiment of a circuit 430 corresponding to the equivalent circuit model shown in FIG. 4A. Those of skill in the art of circuit design will readily appreciate that other circuits configurations are possible. The series circuit blocks 422a, 424a, and 426a each consists of a series-coupled resistor and inductor. The shunt circuit blocks 422b, 424b, and 426b each consists of a parallel-coupled resistor and capacitor. Series resistors $R_t$, $R_m$, $R_s$ model respectively the resistivity of the interface transmission line, the MBL, and the solution. Shunt resistors $R_m'$, $R_s'$, $R_d$ model respectively the resistivity of the MBL, the solution, and the dielectric layer. Series inductors $L_t$, $L_m$, $L_s$, model respectively the inductance of the interface transmission line, the MBL, and the solution. Shunt capacitors $C_m$, $C_s$, $C_d$ model respectively the capacitances of the MBL 234, the solution 260, and the dielectric layer 240. Collectively, the aforementioned resistors, inductors, and capacitors define the circuit 430 which transforms the input signal $V_i$ into the output signal $V_o$.

The dielectric properties of the MBL largely determine the values of the circuit elements corresponding to each of those layers. For instance, in the illustrated embodiment of FIG. 4B, the susceptibility of the MBL largely defines the value of the shunt capacitance $C_m$. Further, the dispersive properties of the MBL largely determine the value of the shunt resistance $R_m'$. The values of $C_m$ and $R_m'$ define to a significant degree the signal response of the bio-electrical interface. Thus, the signal response of the bio-electrical interface is strongly characteristic of the dielectric properties of the MBL and can be used to detect and identify molecular binding events, as will be further described below.

In embodiments where the solution 260 is an aqueous solution, the dielectric properties associated therewith are disadvantageous to signal propagation along the interface transmission line. Specifically, water and other highly aqueous solutions such as whole blood, exhibit a relatively high resistance $R_s$ and a relatively low resistance $R_s'$, as well as absorptive properties with respect to electromagnetic radiation in certain areas of the spectrum. The magnitude of these parameters results in very high signal loss along the interface transmission line. The location of the MBL between the interface transmission line and the solution in the present invention serves to insulate from, or otherwise modulate the coupling with, the signal and the solution, thereby modulating the signal loss and changing other parameters of signal propagation.

FIG. 4C illustrates one embodiment of an equivalent circuit model 450 for the bio-electrical interface structure shown in FIG. 2B. Those of skill in the art of circuit design will appreciate that the illustrated circuit model is not exhaustive and that other equivalent circuit models may be derived from the bio-electrical interface of FIG. 2B.

The illustrated equivalent circuit model 450 includes series and shunt circuit blocks 452a and 452b which electrically model the interface transmission line. The equivalent circuit model 450 also includes a MBL circuit block 454 coupled in series with a solution circuit block 456 which electrically models the MBL and solution. As explained above, the orientation of the series and shunt blocks 452a and 452b define a conventional transmission line structure. Additionally, the series orientation of the MBL and solution circuit blocks 454 and 456 results from signal field lines extending from interface transmission line, through the MBL, and into the solution, the arrangement of which is shown in FIG. 2B. Alternative circuit models may be derived as above for bio-assay devices implementing a MBL and solution proximate to the ground plane alternatively, or in addition to their location near the interface transmission line.

Figure 4D:
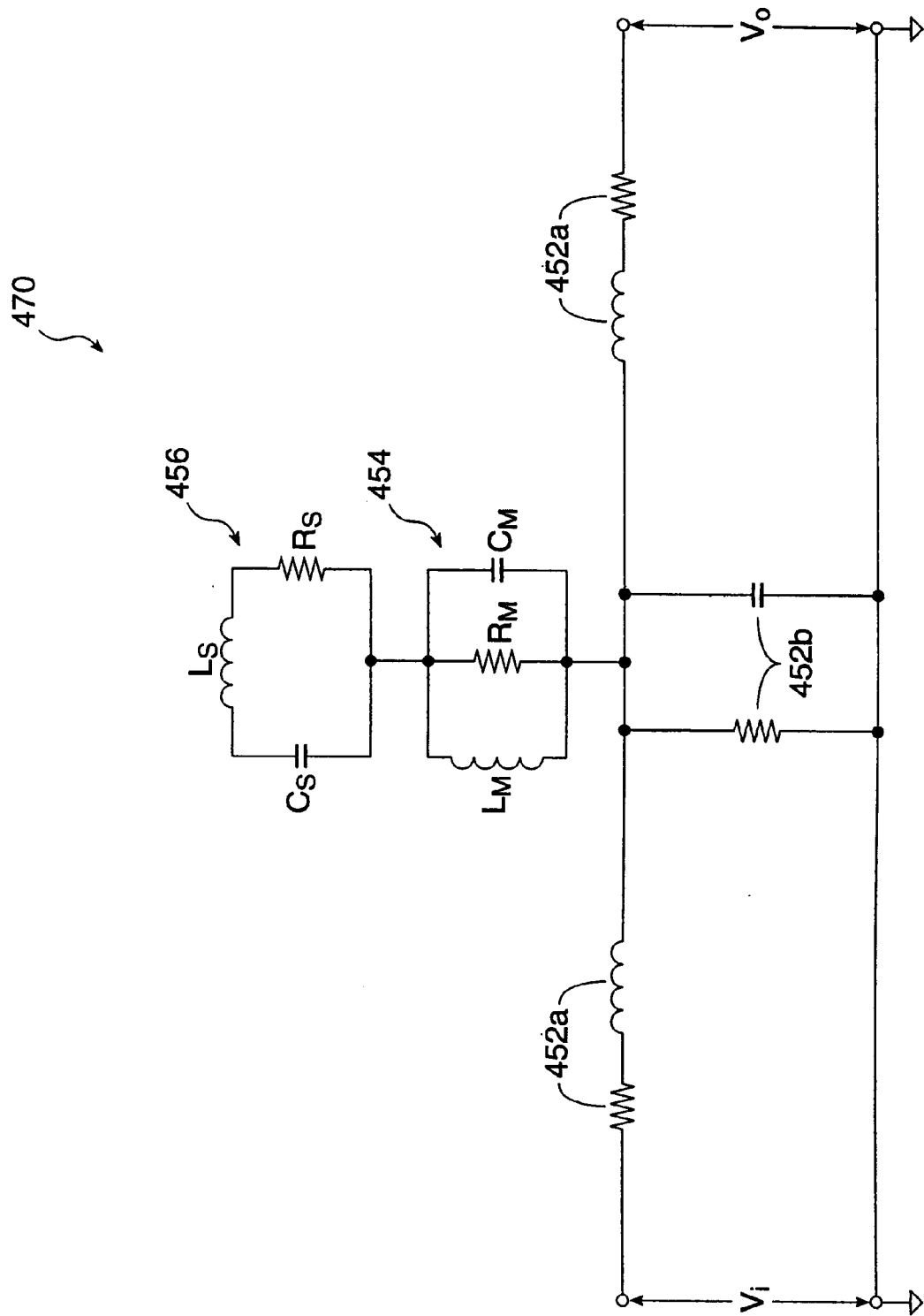
FIG. 4D illustrates one embodiment of a circuit corresponding to the equivalent circuit model shown in FIG. 4C.

FIG. 4D illustrates one embodiment of a circuit 470 corresponding to the equivalent circuit model shown in FIG. 4C. Those of skill in the art of circuit design will readily appreciate that other circuits configurations are possible. The series and shunt circuit block 452a and 452b collectively represent the conventional model for the interface transmission line. The MBL circuit block 454 is coupled between the interface transmission line and the solution circuit block and in one embodiment, consists of a parallel coupled capacitor $C_m$, resistor $R_m$ and inductor $L_m$. Collectively, the aforementioned resistors, inductors, and capacitors define the circuit 470 which transforms the input signal $V_i$ into the output signal $V_o$.

As explained above, the dielectric properties of the MBL and solution will affect the values of each of the electrical elements. In particular, the susceptibility and other dielectric properties of the MBL will largely determine the value of $C_m$; the penniftivity, other dielectric properties, and surface morphology of the MBL will strongly define the value of $L_m$; and the dispersive properties as well as conductive and other dielectric properties of the MBL will significantly determine the value of $R_m$. Thus, the signal response of the bio-electrical interface is strongly characteristic of the dielectric properties of the MBL and can be used to detect and identify molecular binding events, as will be further described below.

D. Specific Embodiments

FIGS. 5A–5G illustrate specific embodiments of the bio-electrical interface implemented in a two conductor circuit topology. Those of skill in the art of circuit design will readily appreciate that each may be implemented in a single conductor waveguide topology, as well as three or more conductor circuit topologies.

Each of the embodiments consists of a signal plane 520, dielectric layer 530, and a ground plane 550. Coupled to signal plane 520, ground plane 550 or both are a MBL 515 and a solution 510. In each of the embodiments, the MBL 515 may either be in direct contact with the interface transmission line 520, or coupled thereto. When the signal plane 520 contacts the MBL 515 directly, it is formed from a material which is capable of both supporting signal propagation and adhering ligands, such as proteins, nucleic acids, carbohydrates, enzymes and the like. Such materials include, but are not limited to gold, ITO, copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof. Other materials which can be used will be readily apparent to those of skill in the art.

The dielectric layer 530 may consist of air, polyimide, teflon, woven insulating materials such as Duriod™, alumina, diamond, sapphire, or semiconductor insulating material such as silicon dioxide or gallium arsenide, or other insulating materials. The thickness and dielectric constant of the dielectric layer 530 are selected to provide the desired transmission line impedance as known in the art. The solution 510 may consist of any transporting medium, such as Dulbecco's phosphate-buffered saline (d-PBS), which provides the subject molecular structure. The protein, nucleic acid, or other ligand of interest can be added to the bio-electrical interface using a variety of techniques such as wicking, pipeting or through capillary action.

Figure 5A:
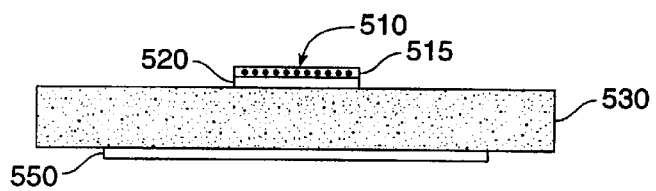
FIGS. 5A–5G illustrate specific embodiments of the bio-electrical interface implemented in a two conductor circuit topology in accordance with the present invention.
Figure 5B:
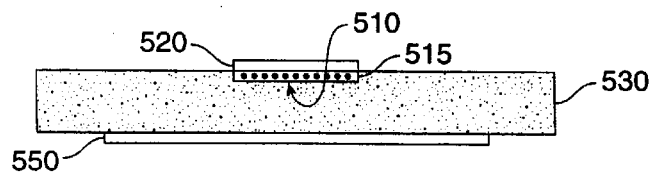
Figure 5C:
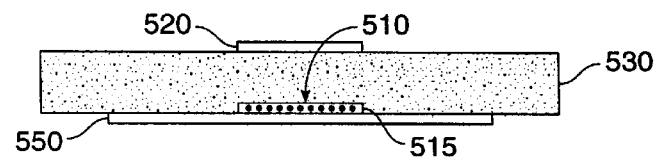
Figure 5D:
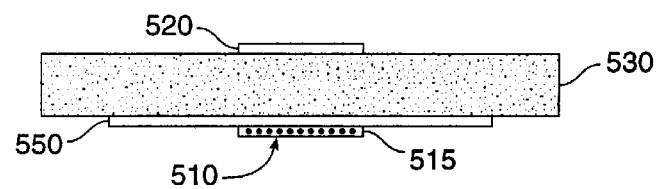

FIGS. 5A and 5B illustrate cross-sectional views of the interface realized in a microstrip circuit topology and in which the solution 510, and MBL 515 are positioned above and below the interface transmission line 530, respectively. FIGS. 5C and 5D illustrate cross-sectional views of the interface in which the solution 510 and MBL 515 are positioned above and below the ground plane 550, respectively.

Figure 5E:
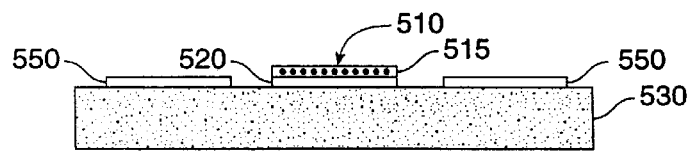
Figure 5F:
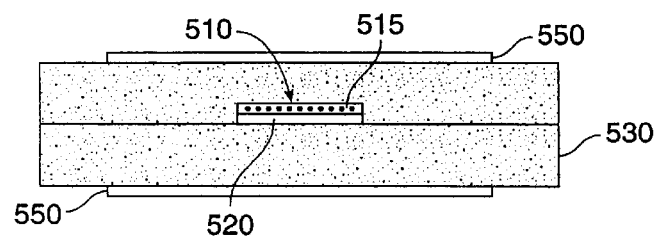

FIG. 5E illustrates a cross-sectional view of the interface realized in coplanar waveguide topology. In this embodiment, the solution 510 and MBL 515 are positioned above the interface transmission line 520. Alternatively, the solution 510 and MBL 515 may be positioned below the interface transmission line 520, or above or below one or both of the coplanar ground planes 550. FIG. 5F illustrates a cross-sectional view of the interface realized in a stripline circuit topology. In this configuration, the solution 510 and MBL 515 are positioned above the interface transmission line 520. In other embodiments, these layers may alternatively or in addition be place below the interface transmission line 520, or above or below one or both ground planes 550.

Figure 5G:
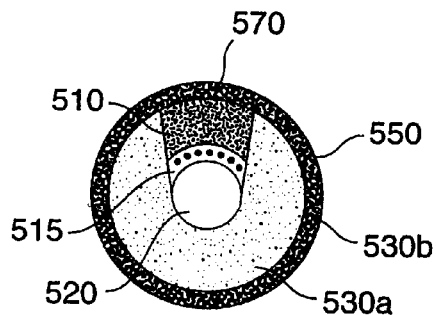

FIG. 5G illustrates one embodiment of the bio-electrical interface implemented in a coaxial circuit topology. A first insulator 530a having a cavity 570 partially circumscribes an interface center conductor 530. The MBL 515 is positioned in proximity to the uncovered portion of the interface center conductor 530. A second insulator 530b is provided between the outer conductor 550 and the first insulator 530a and circumscribes the outer conductor 550, forming the cavity 570 in which the solution 510 resides. The radii and dielectric constants of the first and second insulators 530a and 530b may be of the same or differing values and each is selected to provide the desired line impedance and the requisite measurement sensitivity over the test signal frequency range. In an alternative embodiment, the MBL 515 is located proximate to the outer conductor 550. In this embodiment, the second insulator 530b includes a cavity for allowing the MBL to form proximate to the outer conductor and the first insulator completely circumscribes the center conductor 320. Further alternatively, the MBL 515 and solution may be located outside of the outer conductor 550.

The bio-electrical interface may be fabricated in a variety of shapes depending upon the application, for example, squares, ellipsoids, rectangles, triangles, circles or portions thereof, or irregular geometric shapes, such as one that would fit into the bore of a hypodermic needle. The size of the bio-electrical interface will vary depending upon the application and have sizes on the order of $10 \text{ m}^2$, $1 \text{ m}^2$, $10^{-1} \text{ m}^2$, $10^{-2} \text{ m}^2$, $10^{-3} \text{ m}^2$, $10^{-4} \text{ m}^2$, $10^{-5} \text{ m}^2$, $10^{-6} \text{ m}^2$, $10^{-7} \text{ m}^2$, $10^{-8} \text{ m}^2$, $10^{-9} \text{ m}^2$, $10^{-10} \text{ m}^2$, $10^{-11} \text{ m}^2$, $10^{-12} \text{ m}^2$, anywhere therebetween, The bio-electrical interface may be fabricated to fit into something as small as a needle bore. The interface may alternatively be modified to accommodate other diagnostic applications, such as proteomics chips. The size or shape of the bio-electrical interface need only be such that signal propagation and molecular binding therealong is possible.

V. Measurement Methodology

A. General Overview

The measurement methodology of the present invention makes use of the observation that a vast number of molecules are distinguishable from one another based upon their unique dielectric properties which include dispersion effects, resonance effects, and effects on the solution surrounding said molecules. In the present invention, when a test signal couples to the MBL, the MBL interacts with the energy of the test signal, resulting in a unique signal response. The unique signal response can then be used to detect and identify the molecules which make up the MBL.

Those of skill in the art will appreciate that most molecules exhibit variation in dielectric properties over different frequencies. For instance, a molecule may exhibit a dramatic change in its dielectric properties as a function of frequency in one or more regions of the electromagnetic spectrum. The frequency band over which the molecule exhibits a dramatic dielectric change is often referred to as the molecule's dispersion regime. Over these regimes, the molecule's dielectric constant, permittivity, dipole and/or multipole moments, and susceptibility will change dramatically as a function of frequency. These quantities are often complex, having both real and imaginary parts to account for both the magnitude and phase changes that occur in the signal response. The dispersion regimes range over various frequencies, including the RF, microwave, millimeter wave, far-infrared, and infrared frequencies.

The molecule's dielectric properties can be observed by coupling a test signal to the molecule and observing the resulting signal. When the test signal excites the molecule at a frequency within the molecule's dispersion regime, especially at a resonant frequency, the molecule will interact strongly with the signal, and the resulting signal will exhibit dramatic variations in its measured amplitude and phase, thereby generating a unique signal response. This response can be used to detect and identify the bound molecular structure. In addition, because most molecules will exhibit different dispersion properties over the same or different frequency bands, each generates a unique signal response which can be used to identify the molecular structure.

Detection and identification of molecular binding events can be accomplished by detecting and measuring the dielectric properties at the molecular level. The dielectric properties at the molecular level can be defined by the molecule's multipole moments, the potential energy of which can be represented as an infinite series as is known in the art:

$$\Phi(x) = \frac{q}{r} + \frac{p \cdot x}{r^3} + \frac{1}{2}\sum_{i,j} Q_{ij}\frac{x_i x_j}{r^5} + \cdots$$

The infinite series consists of multiple terms, each of which describes in varying degrees the molecule's dielectric properties in the presence of an electric, magnetic or an electromagnetic field. The first term is referred to as the monopole moment and represents the scalar quantity of the electrostatic potential energy arising from the total charge on the molecule. The second term or "dipole moment" is a vector quantity and consists of three degrees of freedom. The third term or "quadrapole moment" is a rank-2 tensor and describes the molecule's response over 9 degrees of freedom. In general, the $N^{th}$ term is a tensor of rank N−1, with $3^{N-1}$ degrees of freedom, though symmetries may reduce the total number of degrees of freedom. As one can appreciate, the higher-order moments provide greater detail about the molecule's dielectric properties and thus reveals more of the molecule's unique dielectric signature. Since the gradient of the potential results in the electric field:

$$E=-\nabla\Phi(x),$$

The field strength of the higher-order moments falls off rapidly as a function of distance and thus their contribution is difficult to measure. For instance, the field due to dipole moment falls off as $r^{-3}$ and the field due to the quadrupole moment falls off as $r^{-4}$. Thus, this approach requires close proximity between the binding molecules and test signal path and low signal loss therebetween. Since it is often the case that molecular binding event detection occurs in strongly signal-absorbing solutions, such as whole blood samples or ionic solutions, signal loss between the binding events and signal path becomes quite high and detection of the higher order moments is very difficult.

In addition, each multipole term couples to the electric field in a different way. This is demonstrated by first looking at the energy of a given electrostatic system:

$$W=\int \rho(x)\Phi(x)d^3x$$

Expanding the electrostatic potential in a Taylor Series gives $$\Phi(x) = \Phi(0) + x \cdot \nabla\Phi(0) + \frac{1}{2}\sum_i\sum_j x_i x_j \frac{\partial^3\Phi(0)}{\partial x_i \partial x_j}$$

Since $E=-\nabla\Phi(x)$, $$\Phi(x) = \Phi(0) + x \cdot E(0) - \frac{1}{2}\sum_i\sum_j x_i x_j \frac{\partial E_j}{\partial x_i}$$

Further, for the external field, $\nabla \cdot E=0$, so that we get $$\Phi(x) = \Phi(0) - x \cdot E(0) - \frac{1}{6}\sum_i\sum_j (3x_i x_j - r^2\delta_{ij})\frac{\partial E_j}{\partial x_i}$$

Inserting this back into the equation for the energy given above yields $$W = q\Phi(0) - p \cdot E(0) - \frac{1}{6}\sum_i\sum_j Q_{ij}\frac{\partial E_j}{\partial x_i}$$

This shows the manner in which each multipole term interacts with the interrogating field: The total charge q with the potential, the dipole p with the electric field, the quadrupole $Q_{ij}$ with the gradient of the electric field, etc. This illustrates the second difficulty with the detection of the higher order multipole moments: It is difficult in a bulk sample to achieve sufficient field gradients to couple to the higher order moments.

The present invention overcomes the aforementioned obstacles by implementing the described bio-electrical interface. The interface includes a MBL which is coupled along the signal path. The MBL consists of a very thin and highly inhomogeneous layer (from a dielectric standpoint), thus providing the required proximity to the electromagnetically probing structure as well as the sufficient field gradients to couple to the higher order multipole moments. These qualities enable detection of higher order moments which provide a greatly enhanced view of the molecule's dielectric properties. The positioning of the MBL proximate to the signal and/or ground planes serves to isolate the signal propagating thereon from becoming absorbed into solution, thereby reducing the signal loss and enabling the usage of higher test frequencies to more accurately detect and identify the binding events. In this manner, the present invention enables to a greater degree the recovery or the signal response including the contributions from the molecule's dipole and other higher-order multipole moments.

Figure 6A:
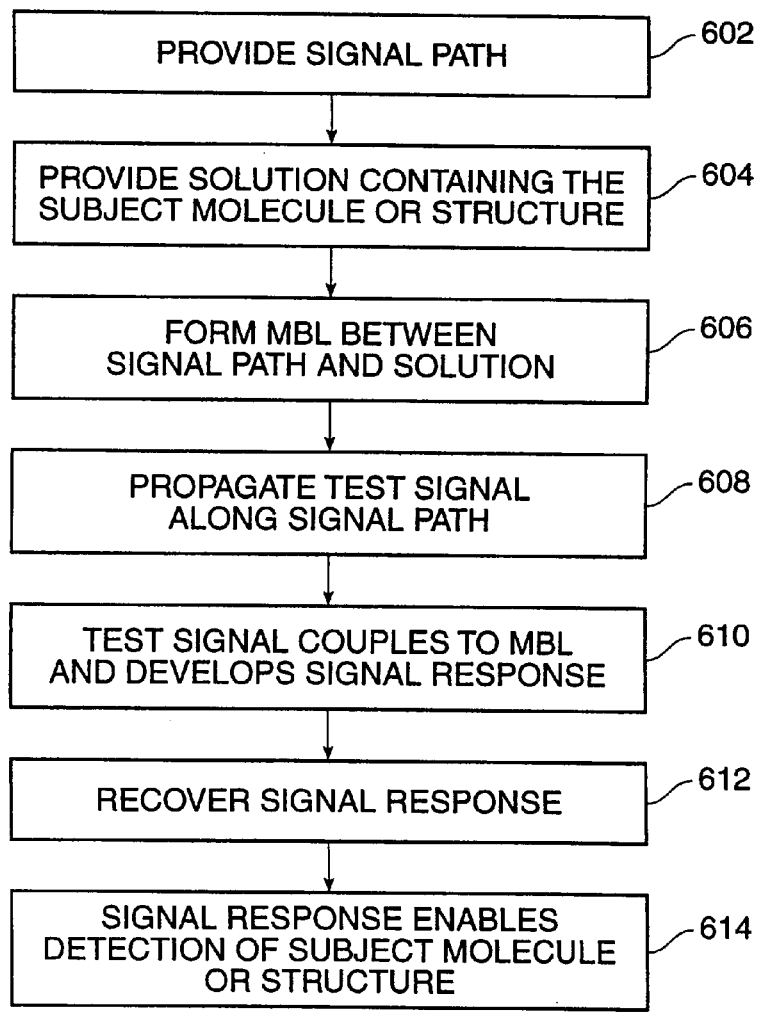
FIG. 6A illustrates one embodiment of a method for detecting molecular binding events in accordance with the present invention.

Using the described bio-assay device of the present invention, numerous properties associated with the MBL may be detected. FIG. 6A illustrates one embodiment of this method. Initially at step 602 a MBL is formed and coupled along a portion of a signal path. As described, the MBL may consist of a ligand, antiligand/ligand complex, etc and be in direct or indirect physical contact with, or electromangentically coupled to the signal path. The signal path may consist of the signal plane or ground plane in a two-conductor transmission topology.

Next at step 604, a test signal is propagated along the signal path. The test signal may be any time-varying signal of any frequency, for instance, a signal frequency of 10 MHz, or a frequency range from 45 MHz to 20 GHz. Next at step 606, the test signal couples to the MBL and in response develops a signal response to the coupling. The signal response is then recovered and provides information as to one or more properties of the molecular binding layer.

The bio-assay device may used to provide information about numerous properties of the MBL, such as the detection and identification of molecular binding events, ligand concentrations, changes in dielectric properties of the MBL, classification of detected binding events, and the like. In addition, the bio-assay device includes a self-calibration capability which is useful in point-of-use quality control and assurance. Each of these methods and capabilities are further described below. Based upon the described methods and structures, modifications and additional uses will be apparent to those skilled in the art.

The ability to detect and measure molecular dipole, quadrupole, and higher order multipole moments in solution represents a significant advance in the art for a number of reasons. First, many molecules of biomedical interest such as proteins have very distinct structures, and therefore distinct multipole moments. Thus identifying the multipole moments for a given molecule reveals properties of said molecule which are unique, and thus allows identification of said molecule. Second, structure and function are intimately related in many molecules of biomedical relevance, such as proteins. Thus, the ability to detect properties of a given molecule which relate directly to the function of said molecule means that functionality may be monitored for whole ranges of activities. Third, the local physiologic environment often plays an important role in the structure and function of a given molecule, so that an ability to detect the physical properties described above means that molecules may be used a monitors and probes for the purpose of measuring changes in a given system. Thus, with the ability to translate complex and informative properties about molecular and cellular systems into a detectable electronic data format, whole new possibilities emerge in the areas discussed herein.

B. Detecting Bound Molecular Structures

The bio-assay device described herein enables the detection of molecular binding events occurring along the signal path. Detectable binding events include primary, secondary, and higher-order binding events. For instance, in a two-conductor bio-electrical interface having no pre-existing MBL, the molecules of the conductive layer will form the antiligands for binding to the ligands, the ligands forming the MBL. In another embodiment, the antiligand and ligand are both included in the MBL. In this embodiment, the MBL is attached to the signal path surface via linkers, matrix molecules, insulating layers or a combination of each as show in FIG. 1D.

FIG. 6A illustrates one embodiment of this process. Initially at step 602, a signal path is formed from a material which can support the propagation of a signal over the desired frequency of operation. The signal path may consist of a single port path, a two port path, or a multiple port path within one of the bio-assay devices described herein. In addition, the signal path may be realized as a transmission line, resonant cavity, or as a waveguide structure.

Next at step 604, a solution is provided which contains the subject molecule or molecular structure. At step 606, a MBL consisting of the ligand is formed from the solution and is coupled between at least a portion of the signal path and the solution. Next at step 608, a test signal is propagated along the signal path. Alternatively, the test signal may be launched during the application of the solution in order to observed in real time the signal response occurring as a result of the binding events. At step 610, the test signal propagates over the signal path, couples to the MBL and develops a signal response which indicates the presence of the ligand. Next at steps 612 and 614, the test signal is recovered, the response of which indicates detection of the ligand.

The dielectric properties of the MBL may contribute to induce any number of signal responses, each of which may be indicative of molecular binding. For instance, the dispersive properties of the MBL may vary dramatically over frequency. In this instance, the test signal response will exhibit large changes in the amplitude and/or phase response over frequency when molecular binding events occur along the binding surface, thereby providing a means for detecting molecular binding events along the binding surface.

In another embodiment, the dielectric relaxation properties of the MBL will vary as a function of pulse period of the input signal. In this instance, the test signal response will indicate a change in the amount of power absorbed, or change in some other parameter of the test signal like phase or amplitude, at or near a particular pulse period. By observing a change in the absorbed power or other parameters, binding events along the binding surface may be detected. Other quantities such characteristic impedances, propagation speed, amplitude, phase, dispersion, loss, permittivity, susceptibility, frequency, and dielectric constant are also possible indicators of molecular binding events.

The above-described method may be used to detect the primary binding of an antiligand or ligand directly or indirectly along the signal path. Similarly, the process of FIG. 6A may also be used to detect secondary binding of a ligand to an antiligand. The method of FIG. 6A is not limited to detection of primary or secondary binding events occurring along the signal path. Indeed, tertiary, and higher-order binding events occurring either along the signal path or suspended in solution can also be detected using this method.

Figure 6B:
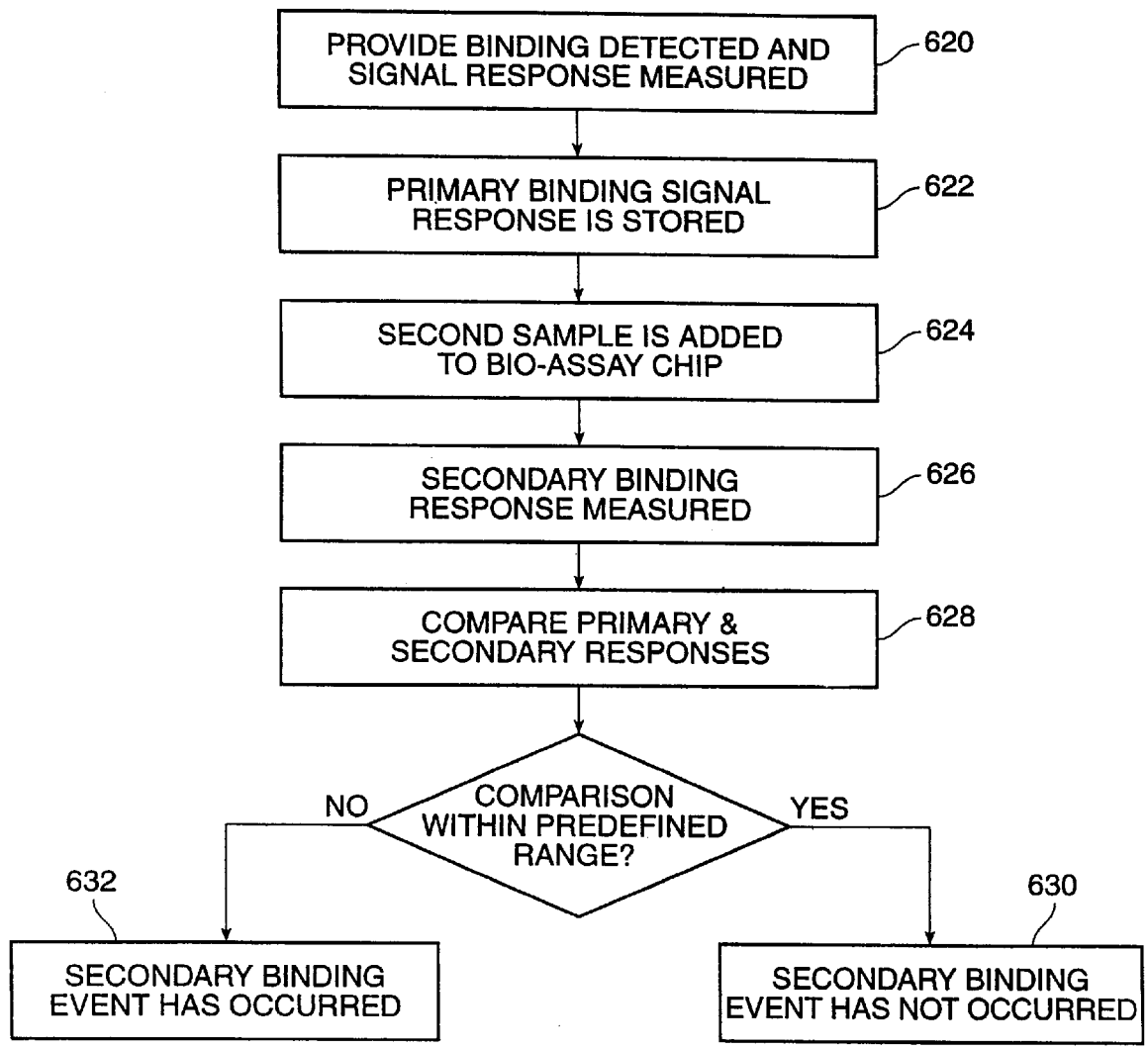
FIG. 6B illustrates one embodiment of a method for detecting secondary and higher-order binding events in accordance with the present invention.

FIG. 6B illustrates a second process for detecting secondary and higher-order binding events occurring either along the signal path. Initially at step 620, the primary binding event is detected and the signal response measured, one embodiment of which is shown in steps 602–612. Subsequently at step 622, the primary binding event signal response is stored and used as a baseline response. Next at step 624, a second molecular solution is added to the bio-assay device and allowed to circulate over the binding surface. Next at step 626, steps 608 through 612 of FIG. 6A are repeated to obtain a second signal response. Next at step 628, the second signal response and the baseline response are compared. Little or no change indicates that the two signal responses are very close, indicating that the structural and dielectric properties of the MBL have not been altered by the addition of the molecules within the new solution. In this case, secondary binding has not occurred to a significant degree (step 630). If the comparison results in a change outside of a predetermined range, the structure and/or dielectric properties of the MBL have been altered, thereby indicating secondary binding events (step 632). Quantities which can be used to indicate secondary binding events will parallel the aforementioned quantities, e.g., amplitude, phase, frequency, dispersion, loss, permittivity, susceptibility, impedance, propagation speed, dielectric constant as well as other factors. Tertiary or high-order binding events may be detected using this approach.

An alternative method of detecting secondary or higher order binding events does not required prior knowledge of the specific primary binding event. In this embodiment, the bio-assay device is designed in the assay development stage to operate with known parameters, so that whenever a pre-defined change in one of these parameters is detected, for example at the point-of-use, the binding event or events are then known to have occurred. In this embodiment, the pre-measurement of a primary binding event is not necessary, as the initial characterization has already been done either at the time of fabrication or at the time of design.

Secondary binding events can also be achieved by detecting changes in the structure of the primary bound molecule. When a molecule becomes bound, it undergoes conformational and other changes in its molecular structure relative to its unbound state. These changes affect the primary binding molecule's dielectric properties as well as inducing changes in the surrounding solution, the variation of which can be detected using steps 620–628 of FIG. 6B, described above. Quantities which can be monitored to indicate a change in the dielectric properties of the primary bound molecule include the aforementioned quantities, e.g., amplitude, phase, frequency, dispersion, loss, permittivity, susceptibility, impedance, propagation speed, dielectric constant as well as other factors.

C. Detecting Changes in the Dielectric Properties of the Molecular Binding Layer The bio-assay device described herein may also be used to measure the dielectric changes of the MBL as a result of changes in temperature, pH, ionic strength and the like.

Figure 6C:
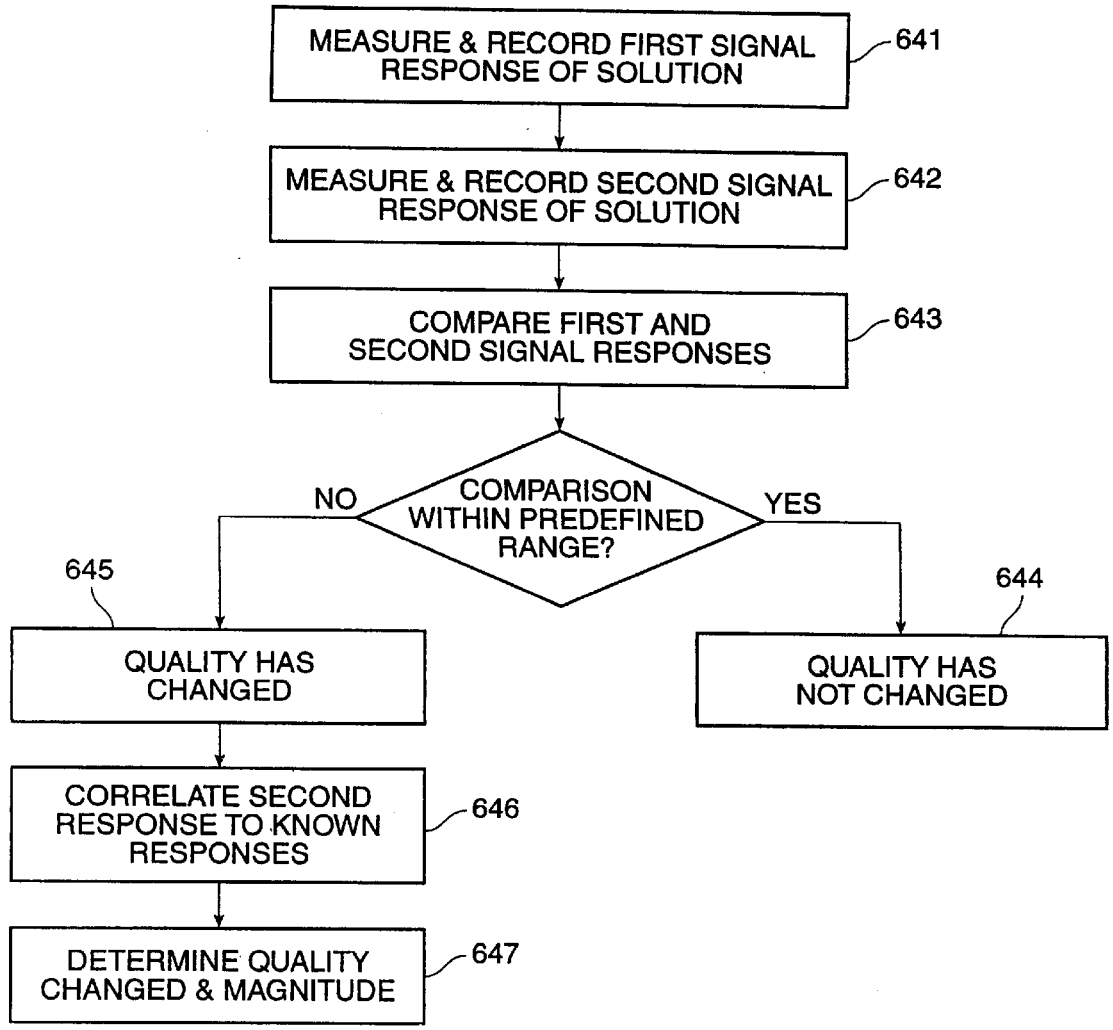
FIG. 6C illustrates one embodiment of a method for measuring dielectric changes of the molecular binding layer in accordance with the present invention.

FIG. 6C illustrates an exemplary embodiment of the process. The process closely parallels the disclosed method for identifying binding events, the exception being that the method allows for the detection and quantitation of changes in dielectric properties of the MBL.

The process begins at step 641, when a solution having an initial dielectric property is added to the bio-assay device, the signal response is measured and recorded. In one embodiment, this step is performed according to steps 602–612. After a predetermined time or operation, a second measurement is made and a second signal response is recorded (step 642), again in one embodiment according to steps 602–612. At step 643, a comparison is then made between the first and second signals to determine whether the two signals correlate within a predefined range. If so, the properties of the solution are deemed to not have undergone any dielectric changes (step 644).

If the signal responses do not correlate within a predefined range, one or more dielectric properties of the solution is deemed as having undergone a change (step 645). Optionally the change in dielectric properties may be quantitated in the following manner. At step 646, the second signal is stored and correlated to a known signal response. The closest correlated response will identify the dielectric property of the solution and the first signal response can be correlated to the initial value of the dielectric property, the difference of which can be used to determine the amount by which the identified dielectric property has been altered (step 647).

D. Identifying Bound Molecular Structures

Figure 6D:
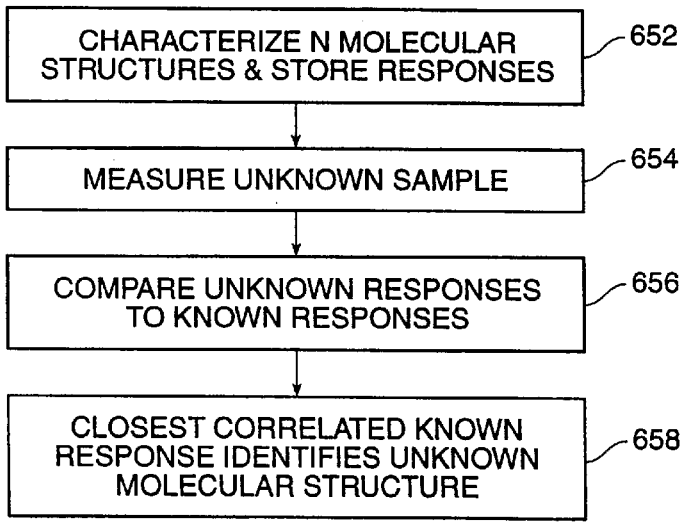
FIG. 6D illustrates one embodiment of a method for identifying a ligand in an unknown solution in accordance with the present invention.

Using the described bio-assay devices, it is possible to characterize a known ligand and subsequently identify it in a solution having an unknown ligand make-up. FIG. 6D illustrates one embodiment of this process. Initially at step 652, a large number of molecular structures are measured and their responses stored using one or more of the measurement systems, described below. In one embodiment, this step is performed according to steps 602–612. Each stored response may correspond to a single ligand occurring within the solution or multiple ligands occurring within the same solution. Subsequently at step 654, a measurement is made of an unknown solution. In one embodiment, this step is performed according to steps 602–612. Next at step 656, the signal response of the solution is compared to the stored signal responses to determine the degree of correlation therewith. At step 658, the unknown molecular structure is identified by selecting the stored response which exhibits the closest correlation to the unknown response. The comparison may be performed using one or more data points to determine the correlation between one or more stored responses, and may involve the use of pattern recognition software or similar means to determine the correlation. The process may be used to identify primary, secondary or higher-order bound molecular structures.

E. Identifying Classes of Bound Molecular Structures

It is also possible to characterize known molecular substructures such as domains or other structural homologies that are common to similar classes of proteins or sequence homologies in nucleic acids. In one embodiment, the process proceeds as shown in FIG. 6D, except that in step 652, N number of molecular sub-structures are measured and their responses stored. Each stored signal response may correspond to one or more sub-structures. The process continues as described in steps 654, 656 and 658 until a sufficient number or structures have been detected and characterized to identify the unknown compound. Once a sufficient number of correlations occur, it is then possible to classify the unknown molecular structure.

Figure 6E:
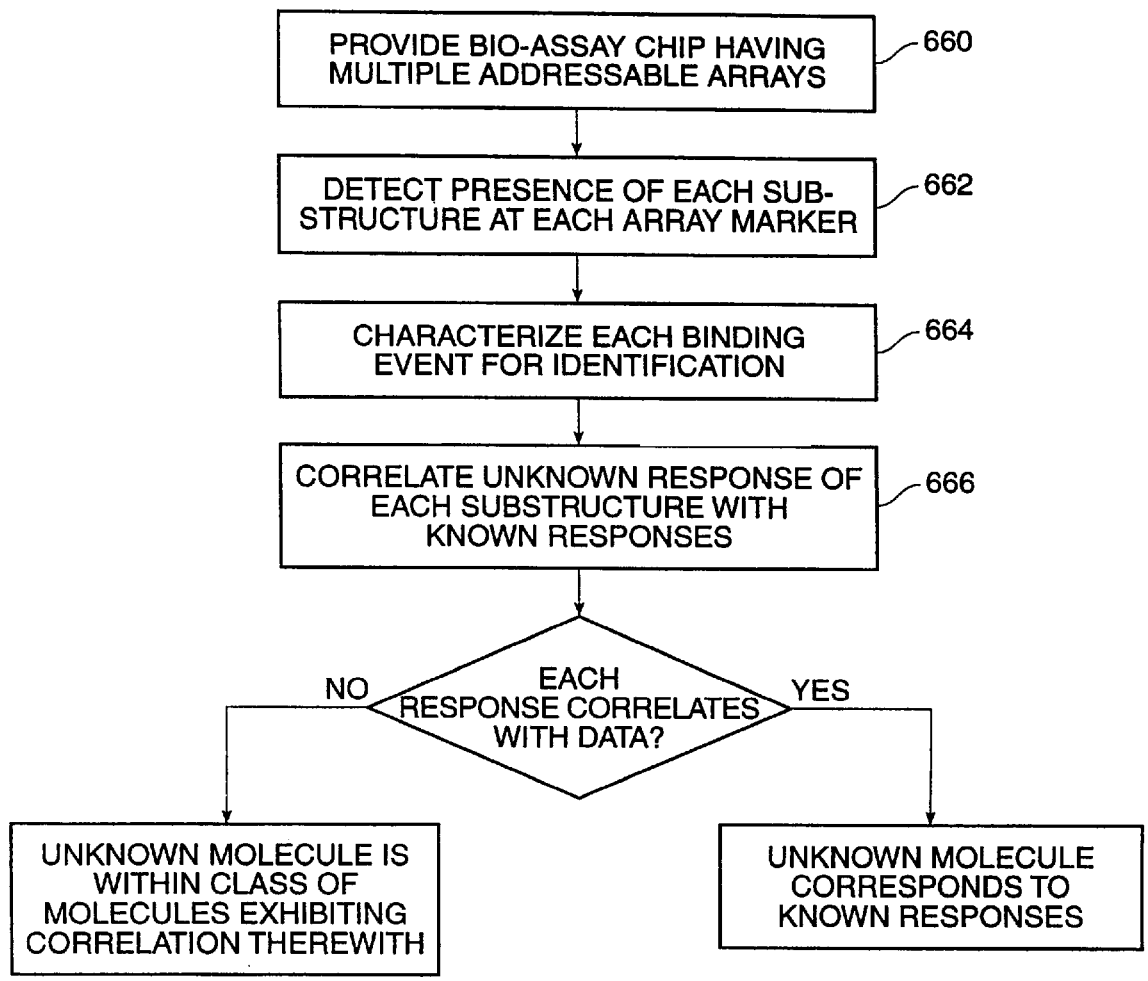
FIG. 6E illustrates one embodiment of a method for identifying the class of a ligand in accordance with the present invention.

FIG. 6E illustrates another process by which unknown ligands may be classified. The process identifies the unknown ligand by detecting binding to structural motifs on the unknown compound. Initially, at step 660 a bio-assay device is provided which has multiple addressable arrays, each of which has a antiligand for a specific ligand substructure. Next at step 662, the presence of particular sub-structures is detected by the binding of each to its respective antiligand, and subsequent characterization. In one embodiment, this step is performed according to steps 602–612. Subsequently at step 664, each of the binding events is then characterized by identification of qualities such as affinity, kinetics, and spectral response. At step 666, a correlation is then made between the known and unknown responses. If each of the unknown responses correlates to known responses, the ligand is identified as the ligand corresponding to the known response. If the sub-structures exhibit both correlated and uncorrelated responses, the correlated responses may be used to construct a more general classification of the unknown ligand. This process may be used to identify any molecular structure, for example proteins, which occur within the same class or have re-occurring structural homologies.

It is also possible that an intensive spectral analysis of a given unknown compound could lead to insights on structure and function, as comparisons can be made to known structures, and extrapolation will lead to some level of classification.

A. Specific v.s. Non-Specific Binding:

Specific ligand binding is distinguished form non-specific binding by the spectral fingerprint of the binding event. A given binding event of interest, for example antibody binding to antigen, may be first characterized in a purified solution containing just the ligand of interest and the antiligand specific to said ligand on the MBL. A broad spectral study is then carried out to see when in the spectrum the strongest responses are found. The assay is then repeated in the solutions typically found in the dedicated applications, for example whole blood, to determine what effects non-specific binding has on the response. Then various points are found which are determinate of specific binding, and a separate set of points are found which are determinate of non-specific binding, an a subset of these frequency points are chosen for the actual assay application. By comparing the response due to specific binding with those due to the non-specific binding, the extent of specific binding can be determined.

B. Characterization of a Given Ligand:

Often it is desirable to determine certain qualities of a given molecule. Examples in include determining the class to which a protein belongs, or which type of polymorphism a given gene or other nucleic acid sequence is. This may be done in a number of ways. Proteins are often classified by number and types of structural homologies, or particular substructures which are found in the same or similar classes of proteins. For example, G-Proteins commonly found in cell membranes and which mediate signal transduction pathways between the extra-cellular environment and the intra-cellular environment, always have a structure which traverses the cell membrane seven times. Such a structure is virtually definitive of a G-Protein. Other classes of proteins have similar structural homologies, and as such, any method which can distinguish one class of proteins from another on the bases of these homologies is of enormous use in many of the biomedical research fields. Given that the dielectric properties of a given molecule is determined entirely by the geometry of the charge distribution of said molecule, and further given that most proteins have a unique structure or geometry, then each protein may be uniquely determined by measuring the dielectric properties of the protein. Thus a simple dielectric signature, such as the ones generated by the present invention, may serve to uniquely identify a given protein, and further, may allow classification of the protein into some previously known class of proteins. A further refinement may be added to the classification methodology by using a group of antiligands on the bio-assay device which are specific for particular sub-structures of a given protein. For example, a group of antibodies which are specific for particular sub-structures such as domains may be utilized for the determination of the existence or absence of said sub-structures. Thus, any given protein may be characterized by determining both the presence and absence of certain sub-structures as well as the dielectric properties of the protein itself. Further refinements to this classification strategy may include looking at temperature, pH, ionic strength, as well as other environmental effects on the above-mentioned properties.

Nucleic acids may also be characterized by following a similar paradigm. For example, a given gene may be known to have a certain base pair sequence. Often times in nature there will be small variations in this sequence. For example, in the gene which codes for a chloride ion transport channel in many cell membranes there are common single base-pair mutations, or changes. Such changes lead to a disease called cystic fibrosis in humans. Thus characterizing a given nucleic acid sequence with respect to small variations is of enormous importance. Such variations are often called polymorphism's, and such polymorphism's are currently detected by forming complementary strands for each of the known polymorphism's. Since any given gene may take the form of any one of hundreds or even thousands of polymorphism's, it is often an arduous task to generate complementary strands for each polymorphism. Using the invention described herein, non-complementary binding or hybridization may be detected and distinguished by measuring many of the same physical properties as were described in the previous paragraph: The dielectric properties of the hybridization event can be characterized and correlated to known data, thereby determining the type of hybridization which has occurred—either complete or incomplete. Thus with an antiligand comprised of a given nucleic acid sequence, hundreds of different polymorphisms (as ligands) may be detected by the characterization of the binding event. One of skill in the art will appreciate that further refinements are possible, such as modifying the stringency conditions to alter the hybridization process, or varying the temperature and determining the melting point, which serves as another indicator of the nature of the hybridization process.

In a similar manner, drug-receptor interactions may be characterized to determine is a given binding event results in the receptor being turned on or off, or some other form of allosteric effect. For example, a given receptor may be used as an antiligand, and a known agonist may be used as the first ligand. The interaction is then characterized according to the dielectric response, and this response is saved. Subsequently, compounds which are being screened for drug candidates are then observed with respect to their binding properties with said receptor. A molecule which binds and yields a similar dielectric response is then known to have a similar effect on the receptor as the known agonist, and therefore will have a much higher probability of being an agonist. This paradigm may be used to characterize virtually any type of target-receptor binding event of interest, and represents a significant improvement over current detection strategies which determine only if a binding event has occurred or not. Those of skill in the art will readily appreciate that there are many other classes of binding events in which the present invention can be applied.

Examples of sub-structures which may be used in the above method include: Protein secondary and tertiary structures, such as alpha-helices, beta-sheets, triple helices, domains, barrel structures, beta-turns, and various symmetry groups found in quaternary structures such as $C_2$ symmetry, $C_3$ symmetry, $C_4$ symmetry, $D_2$ symmetry, cubic symmetry, and icosahedral symmetry. [G. Rose (1979), Heirarchic Organization of Domains in Globular Proteins, *J. Mol. Biol.* 134: 447–470] Sub-structures of nucleic acids which may be analyzed include: sequence homologies and sequence polymorphisms, A, B and Z forms of DNA, single and double strand forms, supercoiling forms, anticodon loops, D loops, and TψC loops in tRNA, as well as different classes of tRNA molecules. [W. Saenger (1984) *Principles of Nucleic Acid Structure*. Springer-Verlag, New York; and P. Schimmel, D. Soll, and J. Abelson (eds.) (1979) *Transfer RNA*. Cold Spring Harbor Laboratory Press, Cold Spring Harbor, N.Y.]

F. Quantitating Concentrations

Figure 6F:
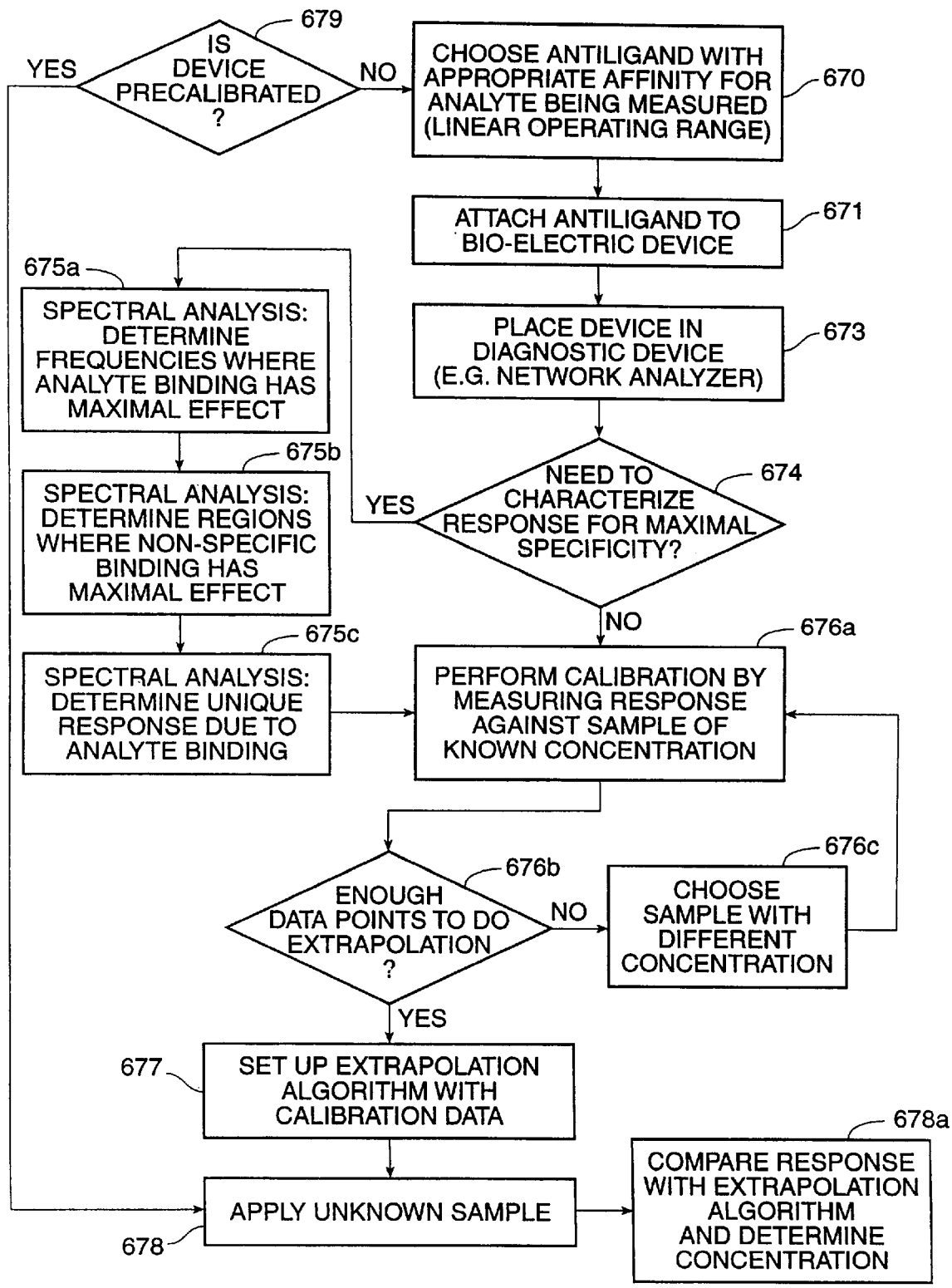
FIG. 6F illustrates one embodiment of a method for quantitating the ligand concentration of a solution in accordance with the present invention.

The bio-assay devices described herein may also be used to quantitate the concentrations of ligands. FIG. 6F illustrates one embodiment of this process. In the event the device is not precailbrated (step 679), initially at step 670, antiligands are chosen having the appropriate binding properties, such as binding affinity or kinetics, for the measured analyte. These properties are selected such that the antiligand's equilibrium constant is near the center of its linear operating region. For applications where the range of concentration is too wide for the use of a single antiligand, several antiligands may be used with differing affinities and/or linear operating ranges, thereby yielding a value for the concentration over a much wider range.

Next at steps 672 and 674, the antiligands are attached to the bio-assay device or chip and the device is connected to the measurement system. At step 674, a decision is made as to whether the response requires characterization for maximum specificity. If so, a spectral analysis is performed in which the frequencies where analyte binding has maximal binding is determined (step 675*a*), the regions where the non-specific binding has maximal effect is determined (step 675*b*), and the unique response due to analyte binding is determined (step 675*c*). If characterization is not required, or if so, after its completion, the device is calibrated. This step is performed in one embodiment by supplying a known concentration of ligands to the bio-assay device and measuring the resulting response (step 676*a*). Alternatively, if more data points are needed for the calibration (step 676*b*), then a sample may be chosen with a different concentration (step 676*c*), and the response against this concentration may be measured (step 676*a*). In one embodiment, the measurement is made in accordance with steps 602–612. Subsequently at step 677, an extrapolation algorithm is generated by recording the calibration points from the foregoing response. Next at step 678, a sample of unknown ligand concentration is measured. This step is accomplished in one embodiment by supplying the unknown sample to the bio-assay device, correlating the response to the titration algorithm, and determining therefrom the ligand concentration.

In the event that a given bio-assay device is either pre-calibrated, or calibrated by design, the only step required is to apply the ligand or analyte to the surface, and measure the response. Such a bio-assay device may be realized in many different ways. For example, some circuit parameter like impedance or characteristic frequency of a resonant circuit may be designed to change in a pre-determined way when the binding event occurs, and the amount by which the parameter changes may further be designed to have a dose-response. Thus, a measurement of said circuit parameter will, when analyzed via a suitable algorithm, immediately yield a quantitative value for the concentration of a given analyte or ligand.

G. Bio-assay Device Self-Calibration

The described bio-assay devices possess a self-diagnostic capability and thus a point-of-use quality control and assurance. For a given dedication application, a particular antiligand (primary binding species) will act as an antiligand for some ligand (the secondarily binding species) of interest in the solution. The primary binding species may be attached at the point of fabrication, and the secondary binding species may be attached at the point-of-use. Thus, variations in fabrication—especially the attachment of the primary species—will cause variations in the ability of the device to bind its specific ligand. However, the amount of ligand bound will be in direct proportion to the amount of antiligand bound, thus a ratiometric measurement of the two is possible.

Figure 6G:
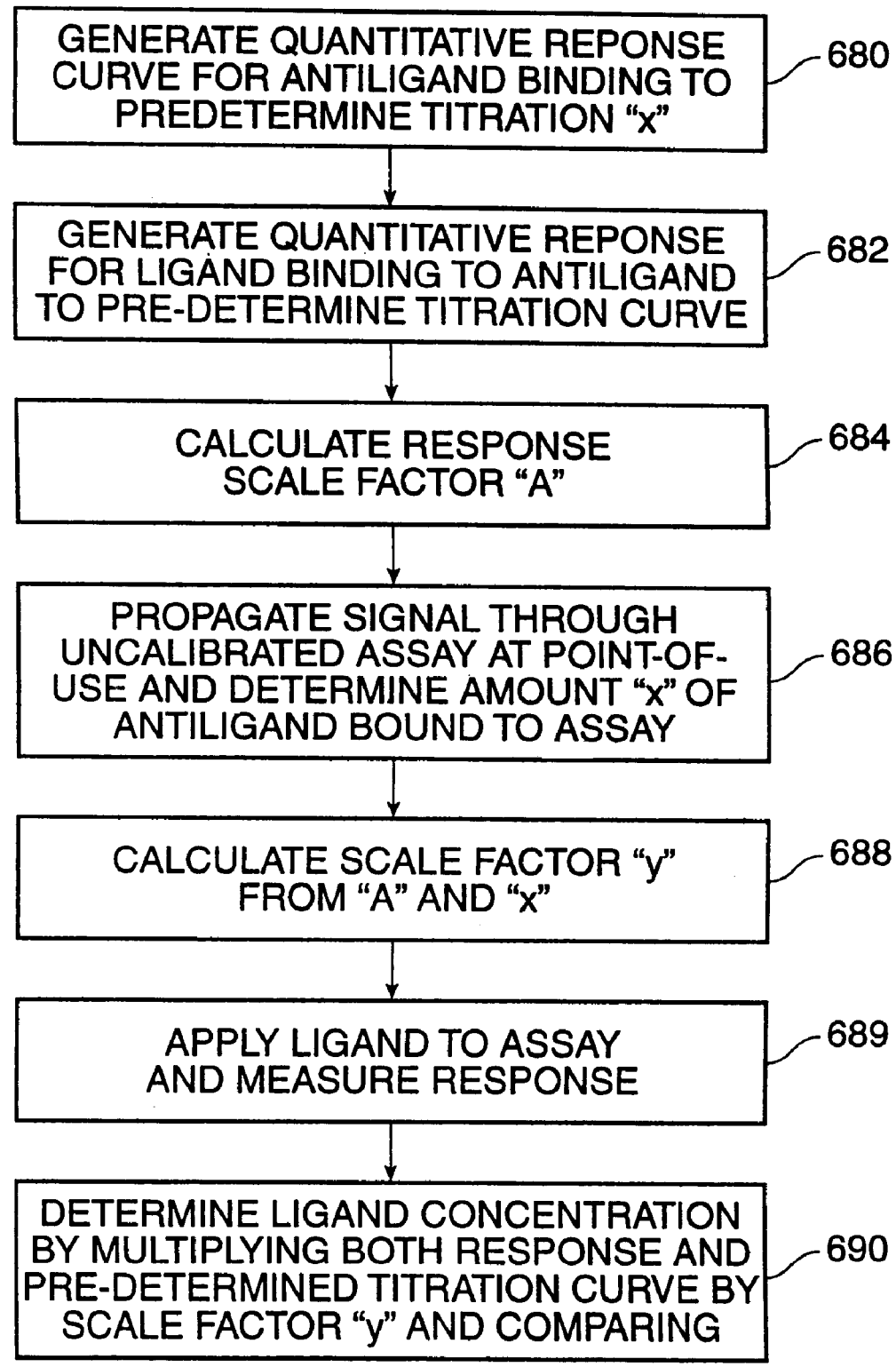
FIG. 6G illustrates one embodiment of a method for providing a self-diagnostic capability of the bio-assay device in accordance with the present invention.

FIG. 6G illustrates one embodiment of the process. Initially at step 680, a molecular binding surface is formed along the signal path by binding the appropriate antibody at various concentrations and characterising the resulting response for each of these concentration, yielding some value "x" for each concentration. Next, at step 682, a similar titration curve is generated for the ligand by measuring the antibody/ligand binding response for several different concentrations of ligand, and a ligand titration curve is predetermined. Next, at step 684 a scale factor A is generated by taking the ratio of responses of antibody binding to ligand binding. At the point-of-use, the uncalibrated assay is then first probed (step 686) to determine the amount of bound antibody "x" and the scale factor "y" resulting therefrom. The ligand is then applied to the assay and the response is measured (step 689), and the response and predetermined titration curve are scaled by the scale factor "y" (step 690) to determine unknown concentration.

The process of FIG. 6F may also be modified to allow quantitating the amount of ligand in the solution. In the modification, the binding surface of the bio-assay device includes antiligands having a predefined affinity and ligand specificity. The solution is subsequently applied to the device, and a response is measured. The signal response will be proportional to the amount of the ligand that has bound. Thus, a titration of any given ligand may be carried out by choosing an antiligand with an appropriate linear operating range—the range in which the equilibrium constant is within a couple of log units of the desired range of concentrations to be detected. The same ratiometric analysis as described above can be applied to yield a robust and precise quantitative assay with internal controls and calibration necessary to insure reliability.

Each of the described methods may be practiced in a multitude of different ways (i.e., software, hardware, or a combination of both) and in a variety of systems. In one embodiment, the described method can be implemented as a software program.

Figure 7A:
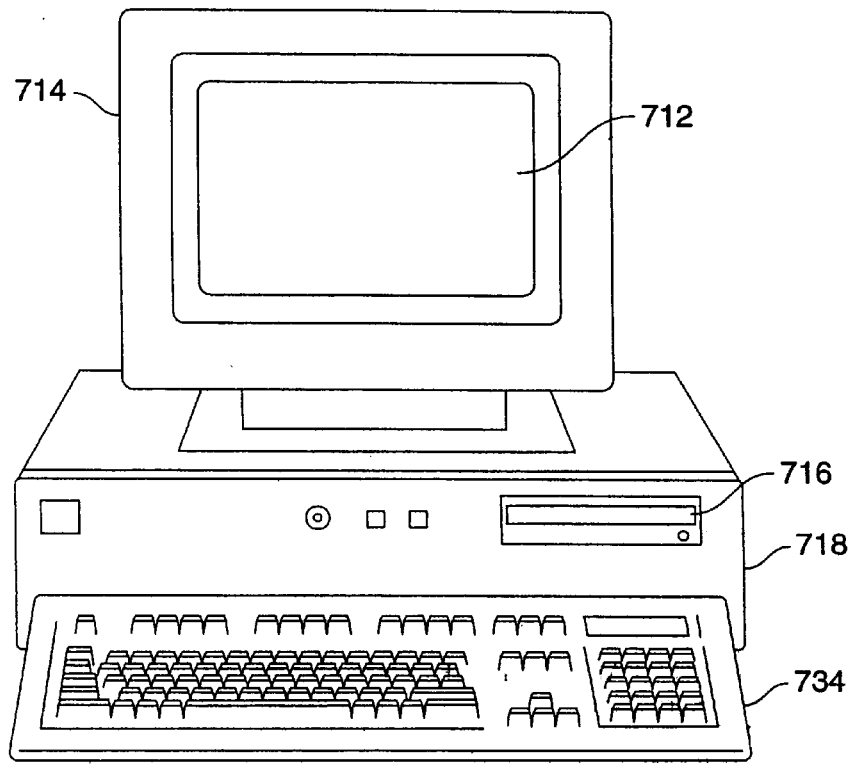
FIG. 7A illustrates one embodiment of a computer system for executing a software program designed to perform each of the methods shown in FIGS. 6A–G.

FIG. 7A illustrates an example of a computer system 710 for executing a software program designed to perform each of the described methods. Computer system 710 includes a monitor 714, screen 712, cabinet 718, and keyboard 734. A mouse (not shown), light pen, or other I/O interfaces, such as virtual reality interfaces may also be included for providing I/O commands. Cabinet 718 houses a CD-ROM drive 716, a hard drive (not shown) or other storage data mediums which may be utilized to store and retrieve digital data and software programs incorporating the present method, and the like. Although CD-ROM 716 is shown as the removable media, other removable tangible media including floppy disks, tape, and flash memory may be utilized. Cabinet 718 also houses familiar computer components (not shown) such as a processor, memory, and the like.

Figure 7B:
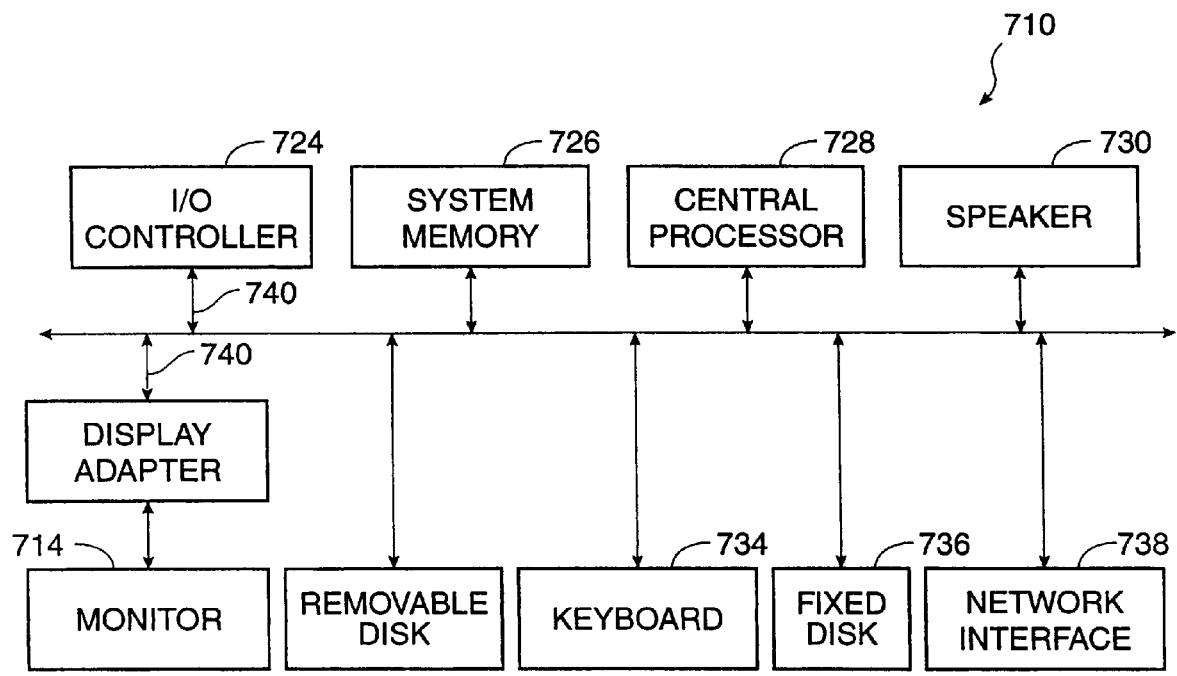
FIG. 7B illustrates a simplified system block diagram of a typical computer system used to execute a software program incorporating the described method.

FIG. 7B illustrates a simplified system block diagram of a typical computer system 710 used to execute a software program incorporating the described method. As shown in FIG. 7A, computer system 710 includes monitor 714 which optionally is interactive with the I/O controller 724. Computer system 710 further includes subsystems such as system memory 726, central processor 728, speaker 730, removable disk 732, keyboard 734, fixed disk 736, and network interface 738. Other computer systems suitable for use with the described method may include additional or fewer subsystems. For example, another computer system could include more than one processor 728 (i.e., a multi-processor system) for processing the digital data. Arrows such as 740 represent the system bus architecture of computer system 710. However, these arrows 740 are illustrative of any interconnection scheme serving to link the subsystems. For example, a local bus could be utilized to connect the central processor 728 to the system memory 726. Computer system 710 shown in FIG. 7B is but an example of a computer system suitable for use with the present invention. Other configurations of subsystems suitable for use with the present invention will be readily apparent to one of ordinary skill in the art.

V. Measurement Systems

Figure 9:
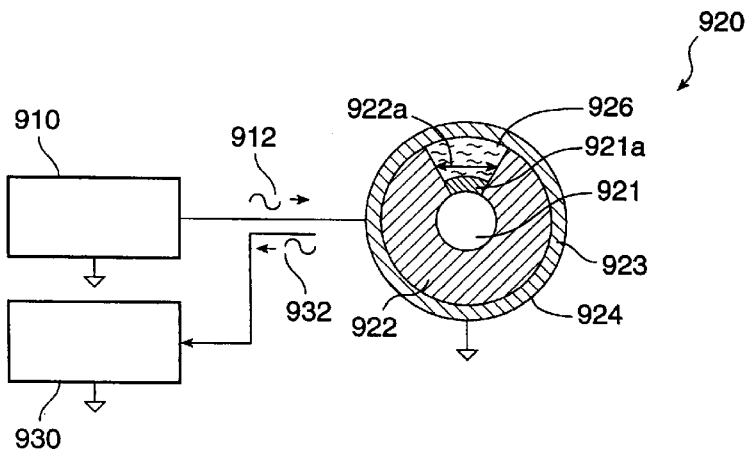
FIG. 9 illustrates a second embodiment of a frequency measurement system in accordance with the present invention.
Figure 10:
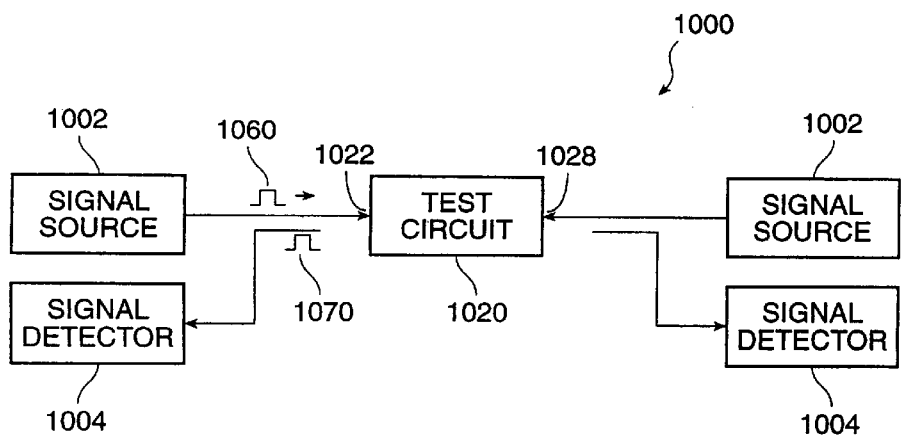
FIG. 10 illustrates one embodiment of a time domain measurement system in accordance with the present invention.

Various measurement systems may be used to perform the above-described methods. FIGS. 8–10 illustrate three examples of possible measurement systems: a frequency domain test system, a time domain test system and a dielectric relaxation measurement system.

A. Frequency Measurement System

Figure 8A:
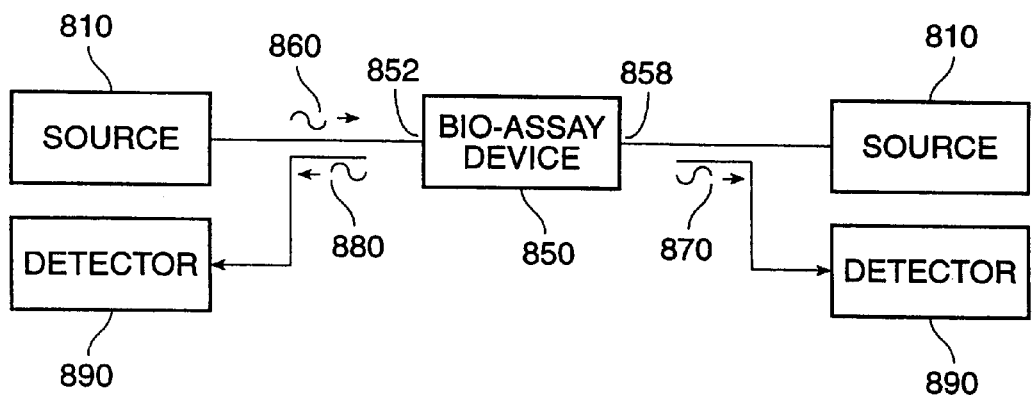
FIG. 8A illustrates one embodiment of a frequency measurement system in accordance with the present invention.

FIG. 8A illustrates one embodiment of a frequency measurement system in accordance with the present invention. The system 800 includes a signal source 810 coupled to the bio-assay device input 852 and a signal detector 890 coupled to the bio-assay device output 858. Optionally, an additional signal source may be coupled to the bio-assay device output 858 and an additional signal detector coupled to the test circuit input 852 for providing complete two-port measurement capability. The system may be modified to a one-port test system in which a signal detector is coupled to the signal path for receiving a reflected signal. In a specific embodiment, the aforementioned frequency measurement system consists of a network analyzer such as model number 8510C from the Hewlett-Packard Company. Other high frequency measurement systems, such as scalar network analyzers, which provide signal information based upon transmitted and reflected signals may alternatively be used.

Figure 8B:
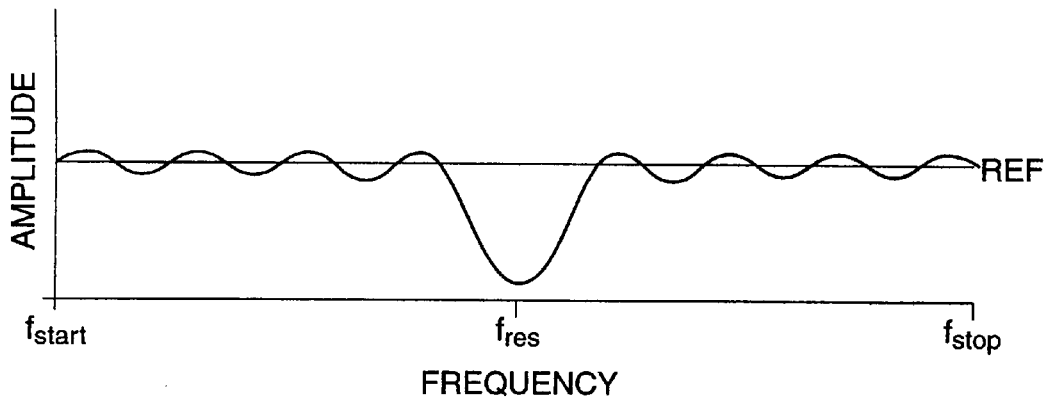
FIG. 8B illustrates a first frequency response measured which can be used to detect or identify a molecular structure in accordance with the present invention.
Figure 8C:
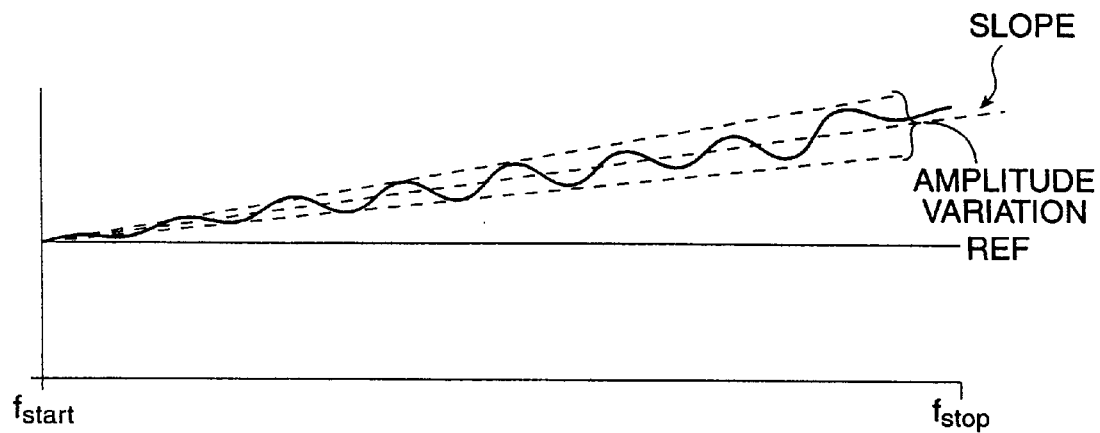
FIG. 8C illustrates a second frequency response which can be used to detect or identify a molecular structure in accordance with the present invention.

Measurements are made according to the aforementioned methodologies. Initially, an incident signal 860 is launched toward the test circuit and the transmitted and/or reflected signals 870 and 890, respectively, are subsequently recovered. The resulting signal responses will take the form of unique frequency responses or "spectral fingerprints," two examples of which are shown in FIGS. 8B and 8C. FIG. 8B illustrates one type of frequency response in which a resonance occurs at frequency $f_{res}$. Here, response 870 undergoes a steep fall and rise, indicating little or no signal energy reaches the output port at this frequency. The resonance is caused by the dielectric property and impedance of the MBL changing over frequency $f_{start}$ to $f_{stop}$. Different ligands will resonate at different frequency points. In addition, some ligands may exhibit multiple resonant frequency points over the measured band $f_{start}$ to $f_{stop}$. Once a ligand has been characterized as having one or more uniquely occurring resonance points, this data can be used to identify the presence of the ligand in an unknown solution. This characterization can be ascertained from empirical data or from theoretical calculations of multipole moments and resonant frequencies. Furthermore, when detecting the presence of secondary binding events, this data can indicate when an analyte is bound to a ligand by a change in the one or more unique resonance points.

FIG. 8C illustrates another type of frequency response which can be used to detect or identify a molecular structure. In this case, the frequency response exhibits a generally monotonically increasing or decreasing trend with some degree of amplitude variation. The response's slope and/or the amplitude variation may be used to detect and/or uniquely characterize the bound molecule. Thus in the described manner, the resonant frequency points, slope, trend, and variation of the test signal's phase may be used to uniquely identify the molecular binding event. The frequency response may be measured at the input port 852, at the output port 858 or at both ports to uniquely identify the bound molecular structure.

FIG. 9 illustrates a second exemplary embodiment of a frequency measurement system in accordance with the present invention. The bio-assay device under test 920 consists of coaxial topology (shown in FIG. 5G) having a center conductor 921, a first insulator 922 having a cavity 922a, a second insulator 923, and an outer conductor 924. Solution 926 occupies cavity 922a. Of course, devices of other circuit topologies may be tested as well.

Once the solution 926 is added to the cavity 922a, the molecules within the solution 926 form a MBL 921a proximate to the center conductor 921. During the measurement, a signal source 910 launches an incident test signal 912 to center conductor 921. The MBL 922a modulates the incident test signal 912, and the reflected test signal 932 provides a unique signal response which can be used to identify the ligand. The one-port coaxial configuration may be realized, for instance, as a sub-cutaneous needle structure.

B. Time Domain Measurement System

FIG. 10 illustrates one embodiment of a time domain measurement system 1000 in accordance with the present invention. The system includes a pulse source 1002 and a detector 1004 coupled to the test circuit input 1022. In an alternative embodiment, an additional pulse source and detector may be coupled to the output port 1028 to provide complete two-port measurement capability. Further alternatively, the system may comprise a one-port test system in which a signal detector is coupled to the signal path for receiving a reflected signal. In a specific embodiment, the time domain measurement system consists of a time domain reflectometer such as model number 11801 manufactured by the Tektronix Corporation. Other high frequency measurement systems, such as network analyzers having a time domain measurement mode which provide signal information based upon transmitted and reflected signal pulses may alternatively be used.

In the time domain measurement system, the input test signal 1060 consists of a time domain pulse, the reflected portions of which can be displayed over time. In the present embodiment, an incident pulse 1060 is launched toward the portion of the transmission line which is tightly coupled to the assay surface. Due to the dielectric property of the MBL, a portion of the incident pulse 1060 is reflected toward the detector 1004. The reflected pulse 1070 will exhibit a unique shape and/or time delay which is characteristic of the MBL's dielectric properties, which are in turn largely defined by the dielectric properties of the ligand, antiligand, and the surrounding solution. Thus, the pulse shape and delay of the reflected pulse 1070 can be used to characterize and identify the ligand. The time domain test system may be used separately or in conjunction with the high frequency test system to identify one or more unknown ligands.

C. Dielectric Relaxation Measurement System

As known in the art, the dielectric relaxation frequency of a ligand is the rate at which the dielectric properties of the molecular level changes when an electric field is applied to the molecule. As with the dielectric properties of the ligand, the dielectric relaxation frequency is primarily defined by the structure and binding geometries unique to each molecule. Thus once measured, the dielectric relaxation frequency of a ligand can be used to identify it.

Figure 11:
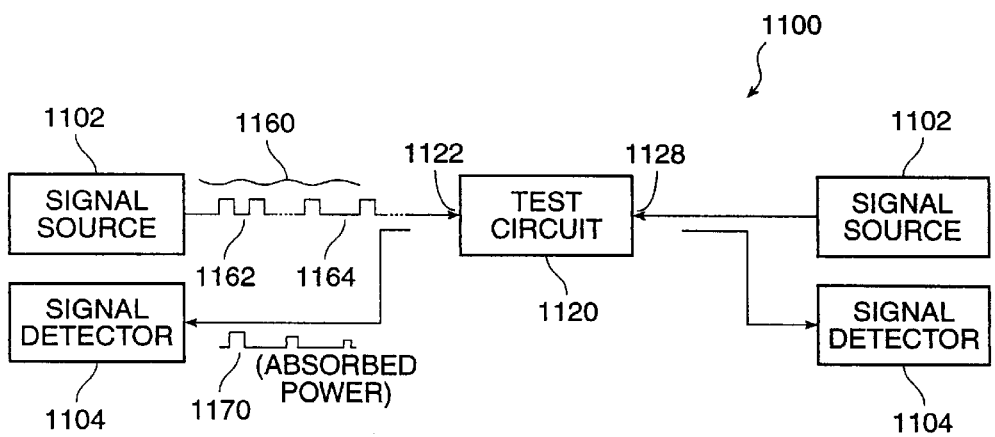
FIG. 11 illustrates one embodiment of a dielectric relaxation measurement system in accordance with the present invention.

The dielectric relaxation frequency can be quantified by measuring the rate at which the ligand absorbs power over frequency. FIG. 11 illustrates one embodiment of a system 1100 for making this measurement. The measurement system 1100 is similar to the time domain measurement system 1000 illustrated in FIG. 10 and includes a pulse source 1102 and a detector 1104 coupled to the test fixture input 1122. An additional pulse source and detector may be coupled to the output port 1128 to provide complete two-port measurement capability. In a specific embodiment, the time domain measurement system consists of a time domain reflectometer such model number 11801 manufactured by the Tektronix Corporation. Other high frequency measurement systems, such as network analyzers having a time domain measurement mode which provide signal information based upon transmitted and reflected signal pulses may alternatively be used.

The input test signal 1160 consists of separate pulse groups, each group having two or more incident pulses and a different pulse interval. The pulse groups 1162 and 1164 are launched toward the portion of the transmission line which is tightly coupled to the binding surface. If a pulse group 1162 has an interval substantially equivalent to the dielectric relaxation period (the reciprocal of the relaxation frequency), the MBL will absorb successively less energy in succeeding pulses. The decrease in signal absorption can be measured in the reflected response 1170 at the input port 1122 or at the output port 1128. As an alternative measurement quantity, the remaining signal power may be measured either at the input port 1122 or the output port 1128.

The rate of change of signal absorption and the pulse interval at which the change occurs can then be plotted and used to characterize and identify the unknown bound molecule(s). This system characterization may be used independently or in conjunction with the above-described time and/or frequency domain test systems.

In all of the above systems, one of skill in the art will readily appreciate that such systems can be scaled down to the chip level using such technologies as Microwave Monolithic Integrated Circuits (MMIC) and the like. Such miniaturized systems can be readily extended to highly parallel systems capable of detecting and measuring hundreds, thousands, or tens of thousands of compounds simultaneously. These systems can be configured to yield "logic gates" which are switched by the binding event itself, such as by changing a characteristic impedance and thus the transmission and/or reflection coefficients, or by changing the band pass properties of such a circuit, and using this as the on/off gate.

VI. Examples

A. Example 1
Detection of a Ligand Binding to the Surface.

Primary binding of urease to an ITO surface was demonstrated in the bio-assay device as shown in FIG. 2A. The binding surface of the bio-assay device comprised a cover glass treated with ITO deposited via chemical vapor deposition (CVD). The ITO transmission line was carefully examined to ensure that it contained no microfractures or breaks in it. The transmission line was measured with a Tektronix 11801 signal analyzer with a TDR module, and found to have a broadband reference impedance of 32 Ω. The line length was about 2.6 nsec in length, the binding surface was found to have an impedance of 34 Ω, and a length of about 200 psec. Separation between the top and bottom plates were 10 mils, and the chamber was ½" long. No side walls were used; instead, the capillary action of the top and bottom plates retained the solution in place.

Next, the bio-assay device filed with a solution of d-PBS. With the bio-assay device filled, baseline transmission loss ($S_{21}$) and return loss ($S_{11}$) S-parameter measurements were made over a test frequency range from 45 MHz to 1 GHz. The measurements were made and stored using a network analyzer model number HP 8510B from the Hewlett-Packard Company. Next, urease was added in a volume excess of 10:1. Transmission loss and return loss S-parameter measurements was repeated and compared to the baseline measurement.

Figure 12A:
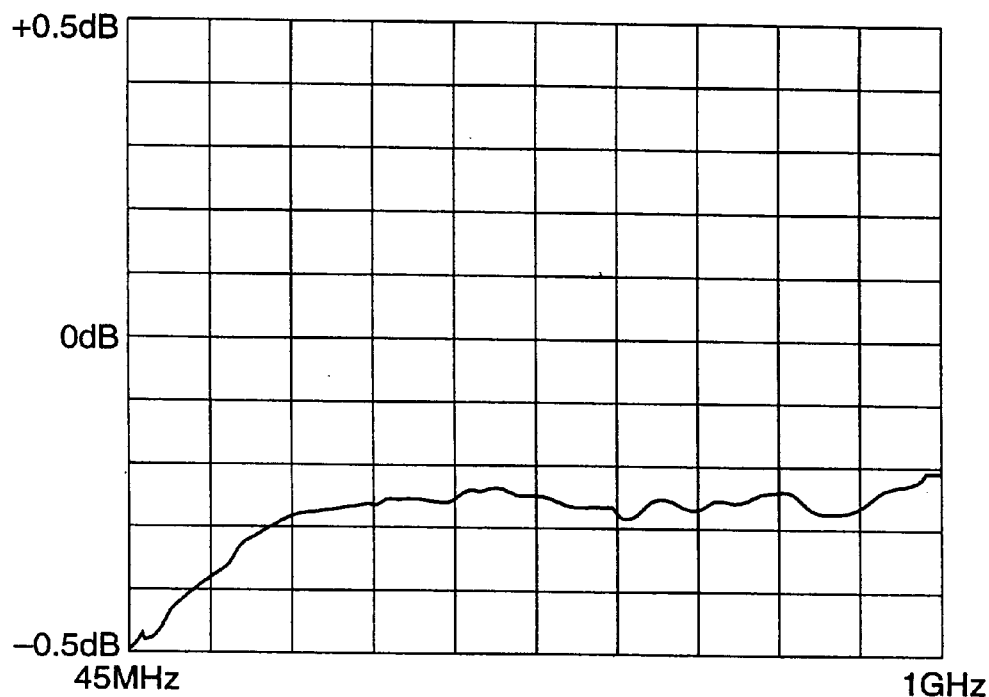
FIGS. 12A–B illustrate the return loss and transmission loss measurements, respectively, of the primary binding of urease to an ITO surface.
Figure 12B:
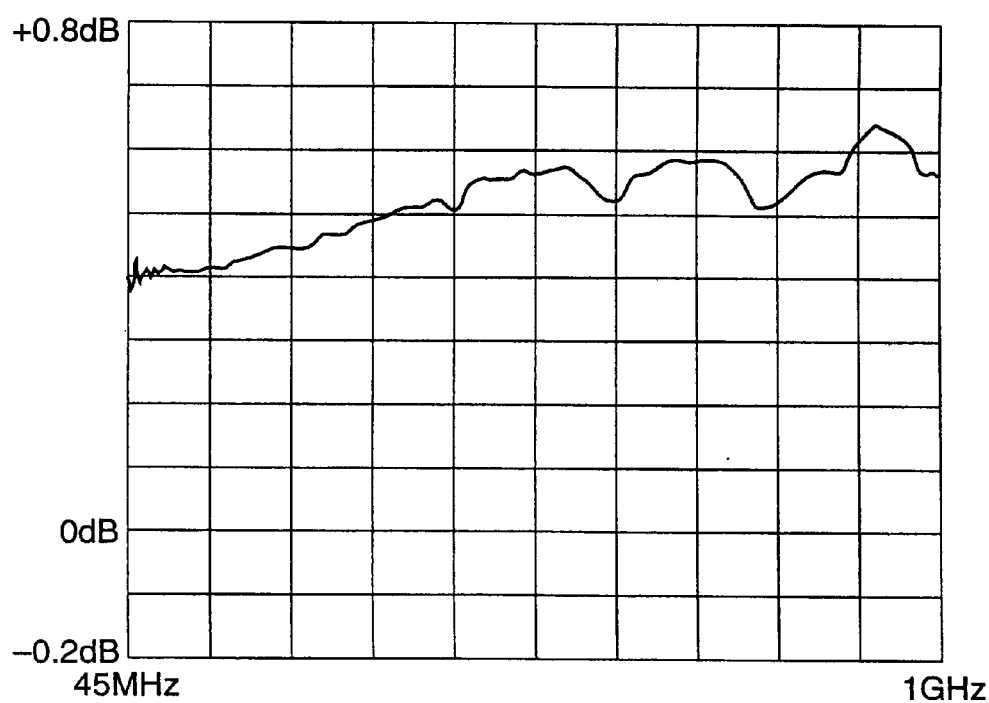

Table 1 below shows these values for 100 MHz and 1 GHz and the return loss and transmission loss measurement responses are shown in FIGS. 12A and 12B. The data indicates that the bio-assay test fixture exhibited a return loss ($S_{11}$) change of −0.5 dB and −0.42 dB, respectively at 100 MHz and 1 GHz between the d-PBS filled chip and the d-PBS+protein filled device. The fixture exhibited a transmission loss change ($S_{21}$) of +0.325 dB and +0.450 dB at 100 MHz and 1 GHz, respectively.

To determine if the signal responses were due to a bulk effect (proteins in solution), or to proteins binding to the binding surface, each response was recorded and the protein solution was flushed with d-PBS in a volume excess of 25:1 (2 mL of d-PBS to 0.075 mL chamber size). The bio-assay device was then re-measured from 45 MHz to 1 GHz as described above.

As can be seen from comparing the last two columns of Table 1, the effect of flushing the protein from the bio-assay device had minimal effect on the return loss and transmission loss measurements. This indicates that the measured effect was indeed due to the urease binding the binding surface within the bio-assay device. In general, it was noted that the replacement of the solution containing the ligand with an identical solution without the ligand caused very little or no change in the response.

TABLE 1

The Effect of Primary Binding of Urease

|  | Frequency | Protein in Solution | After d-PBS Flush |
|---|---|---|---|
| $S_{11}$ | 100 MHz | −500 milli-dB | −475 milli-dB |
|  | 1 GHz | −420 milli-dB | −200 milli-dB |
| $S_{21}$ | 100 MHz | +325 milli-dB | +300 milli-dB |
|  | 1 GHz | +450 milli-dB | +400 milli-dB |

Figure 12C:
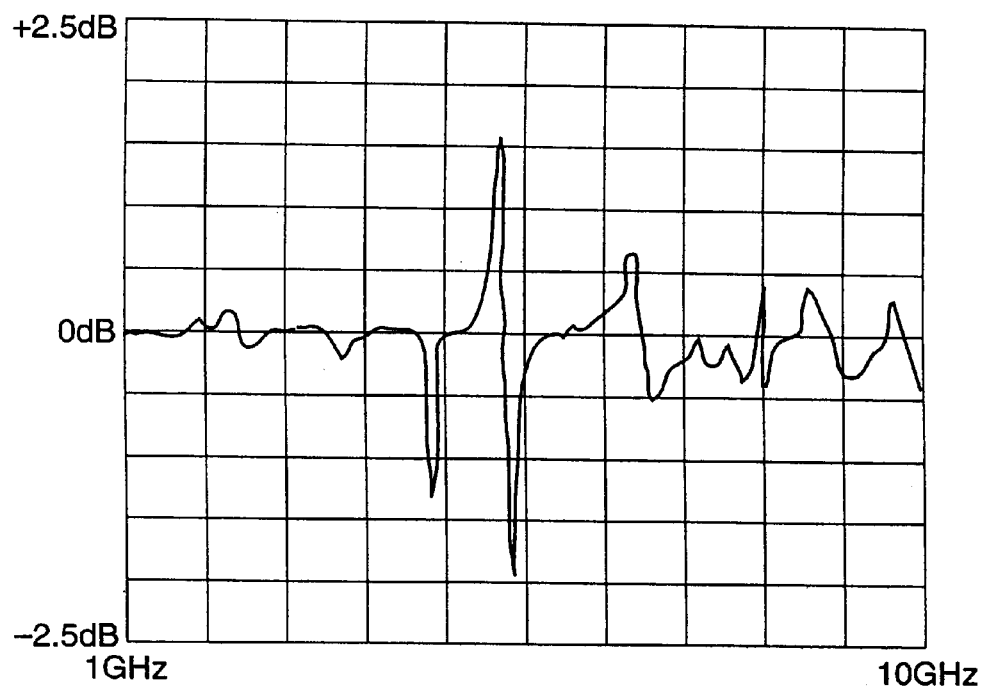
FIGS. 12C and 12D illustrate the transmission loss measurements of the primary binding effects of collagenase and lysozyme.
Figure 12D:
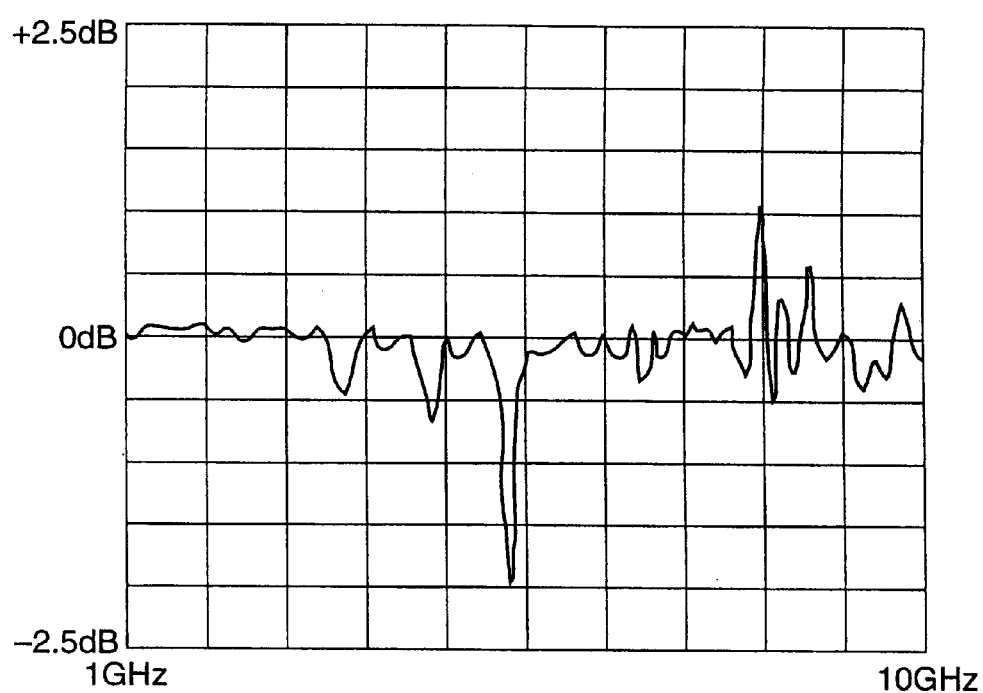

B. Example 2
Identification of Collagenase and Lysozyme through Primary Binding Using a bio-assay device similar to the one cited in example 1 above, and prepared and characterized in a similar manner, we carried out a series of experiments to examine the differing responses of different proteins over the frequency range of 1–10 GHz. The same device was used for each experiment (to eliminate small differences in fabrication from one device to another), but was thoroughly washed with SDS between the application of each of the proteins. FIGS. 12C and 12D illustrate the transmission loss measurements of the primary binding effects of collagenase and lysozyme samples, respectively, over the test frequency range from 1 GHz to 10 GHz. In both instances, the signal response exhibited a pattern of peaks and valleys which can be used to detect and identify the ligand uniquely. In particular, the frequency response of the collagnase sample exhibited a strong positive peak near 5 GHz. The response of the lysozyme sample indicated a relative flat response near 5 GHz and a strong positive peak near 8 GHz. For each of the other numerous proteins examined, the response was unique to each protein, and readily allowed identification of an unknown protein within the group. Of course, additional spectral points may also be compared and analyzed to distinguish these and other molecular substances. The responses may be stored and later recalled to identify unknown samples. In addition the less-pronounced peaks may be examined collectively to determine patterns for particular ligands.

C. Example 3
Detection of Secondary Binding: Concanavalin A to Dextran

This application provides an example of secondary binding detection, using a bio-assay device similar to the one cited in example 1 above, and prepared and characterized in a similar manner. Concanavalin A (con-A) is a glucose binding protein that can be found in jack beans, and was used as the primary binding antiligand The con-A used here was obtained from Sigma Chemical Company. Dextran, a glucose polysaccharide, was then used as a ligand to bind con-A, with glucose as a competitive means of reversing the dextran binding to demonstrate specificity. (Dextran and glucose were also obtained from Sigma Chemical Company.)

Figure 12E:
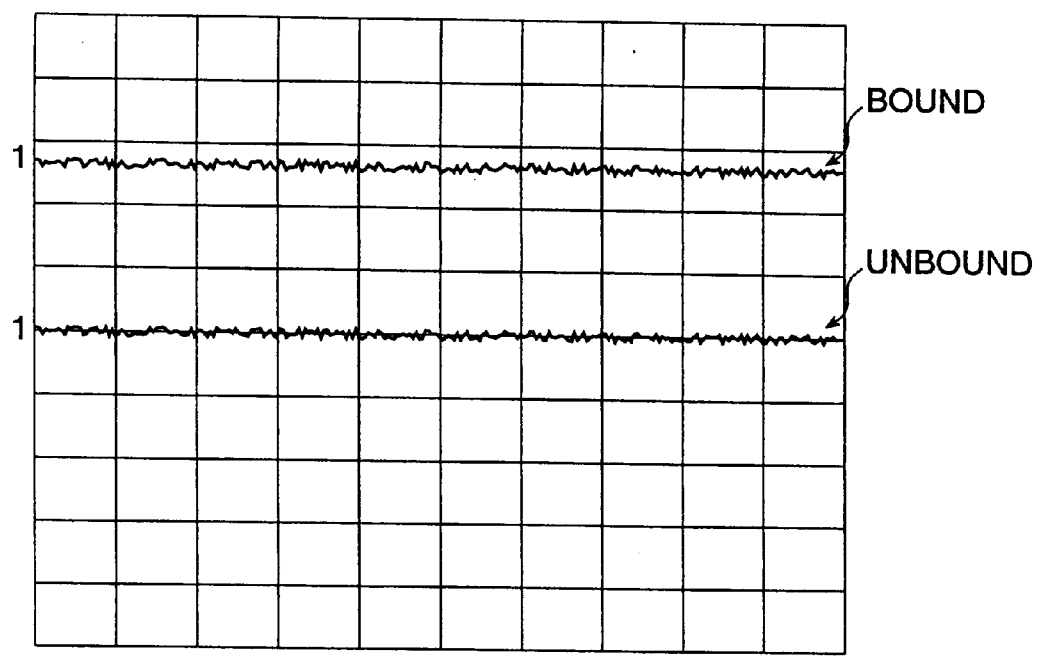
FIG. 12E illustrates the transmission loss response of bound and unbound dextran.

The transmission line was the same as that discussed in Example 1, with a nominal 32 Ω reference impedance, and an ITO cover glass with a DC resistance of 80 Ω and a nominal TDR impedance of 34 Ω. A concentration of approximately 15 μM solution of con-A was placed directly into the bio-assay device, and allowed to reached equilibrium. Evaporative losses did not dry out the chamber as established by visual inspection. After the system was flushed and stabilized, dextran was added to bind the con-A. After a change in the signal was detected, the chamber was flushed with 10 mg/ml d-PBS and the signal response was measured a second time. This effect is shown in FIG. 12E at 1 GHz. The unbound response being used as the baseline response. As shown, the bounded response appears to be 0.25 dB less lossy than the unbound response. Binding specificity was confirmed by competing off the bound dextran with glucose, followed by a d-PBS flush to free the glucose. The latter step returned the signal to the baseline obtained before the dextran had been added to the device, thus demonstrating specificity of the binding event.

D. Example 4
Detection of Small Molecule Binding.

Using a bio-assay device similar to the one cited in example 1 above, and prepared and characterized in a similar manner, the bio-assay test fixture and network analyzer set-up was used to demonstrate that small molecules binding to large molecules may also be detected with the present invention. In order to probe the bio-assay device at higher frequencies, the device was reproducibly and carefully placed in a Faraday box to shield it from external influences. This allowed the device to be probed at frequencies up to 20 GHz. Initially, con-A was added into the bio-assay device and allowed to bind to the bio-electric interface. A transmission loss measurement was made, stored, and used as the baseline response 1252 as shown in FIG. 12F.

Next, a glucose concentration of 10 mg/ml was added to the bio-assay device and used to bind the con-A antiligand. A transmission loss measurement was made and plotted relative to the baseline response 1252 to determine the change in signal response due to small molecule binding.

Figure 12F:
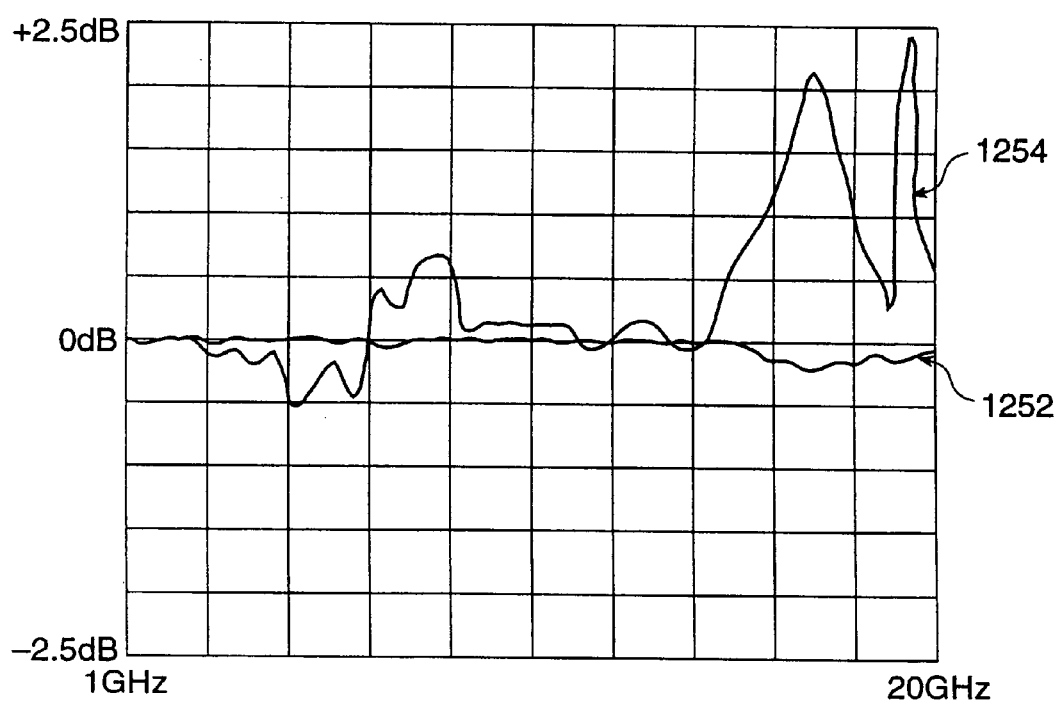
FIG. 12F illustrates the response of con-A unbound and bound to glucose.

As can be seen from FIG. 12F, the binding response 1254, which corresponds to the binding of glucose to con-A, is distinguishable from the baseline measurement 1252. In particular, the binding response 1254 exhibits 2 large peaks between 16–20 GHz which is not observed in the baseline response 1252. The difference in the measured signal responses 1252 and 1254 provides the basis for detecting when glucose has bound to the con-A antiligand. This was followed by a flush with the d-PBS buffer only, and the response was reversed as the bound glucose dissociated from the con-A. A separate experiment looking at the effect of glucose on the bare chip (i.e. no con-A as an antiligand) showed that glucose alone has little if any effect on the response to electromagnetic interrogation in the above mentioned frequency spectrum, thus showing that the result shown is due entirely to the effect of glucose binding to con-A.

Figure 12G:
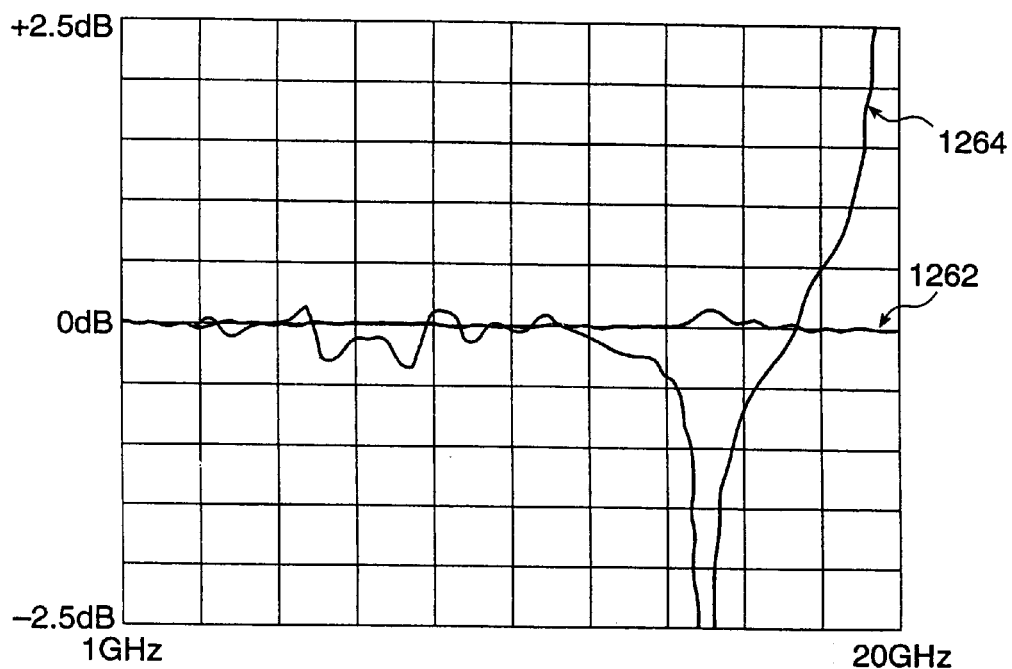
FIG. 12G illustrates the transmission loss of biotin/Avidin relative to the Avidin response.

The experiment was repeated for biotin binding to avidin. Avidin was added to the bio-assay device as the antiligand, and a transmission loss measurement was made, stored and used as a baseline response 1262. Next, a 1 μM concentration of biotin was added, and a transmission loss measurement was made relative to the baseline measurement. The results are shown in FIG. 12G.

The binding response 1264 corresponding to the biotin bound to Avidin indicates a deep null between 14–16 GHz and a large peak near 20 GHz. The differences between the baseline response (indicating unbound Avidin) and the binding response 1264 (indicating bound Avidin) is dramatic and can be used to detect the bound Avidin molecule.

E. Example 5
Quantitation Titrations

These experiments demonstrate that the magnitude of the signal change upon a ligand binding to an antiligand is a function of the number of sites that are occupied. The test system using a bio-assay device similar to the one cited in example 1 above, and prepared and characterized in a similar manner, was used with dextran binding to con-A, with glucose used as a competitive inhibitor. A series of dilutions was created that centered around the binding constant of con-A. Dextran as an antiligand was bound to con-A such that 100% binding occurred. A series of competing glucose concentrations was used to compete off the dextran, so that the concentration of dextran on the molecular binding surface was commensurably decreased.

Figure 12H:
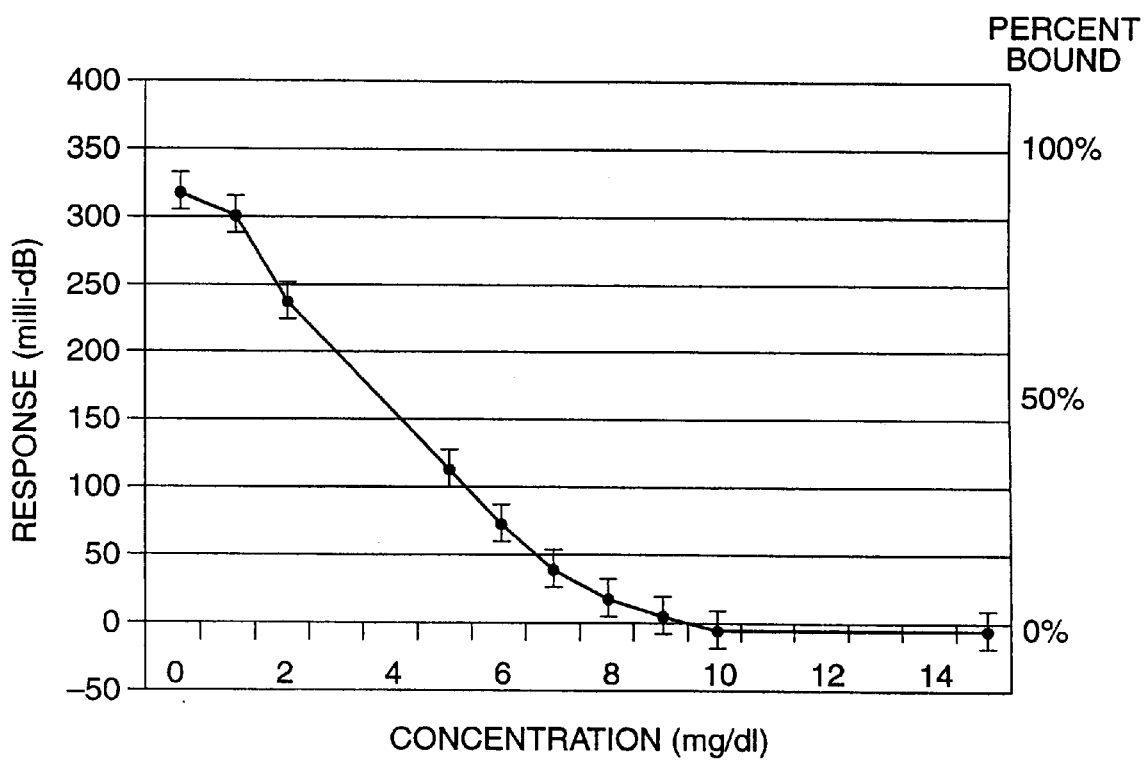
FIG. 12H illustrates the results of a competition titration between dextran and glucose.

The standard transmission line configuration as discussed above was used. Con-A was bound to the molecular binding layer and the system was stabilized. The bio-assay device was then flushed with d-PBS and data obtained at 1 GHz. The results of this competition titration are shown in FIG. 12H. The results show how the signal changes as the concentration of glucose is increased from 0 to 15 mg/dl. The signal of the Con-A changes as the dextran is released and the glucose is bound (which actually measures the avidity of the dextran). Specificity was also demonstrated by reversal by glucose of the dextran binding effect.

Table 2 shows the magnitude of the change in transmission loss as a function of the glucose concentration for some selected concentrations.

TABLE 2

| | |
|---|---|
| Dextran fully bound | +320 milli-dB |
| 1 mg/ml glucose | +280 milli-dB |
| 1.33 mg/ml glucose | +275 milli-dB |
| 2 mg/ml glucose | +240 milli-dB |
| 5 mg/ml glucose | +115 milli-dB |
| 10 mg/ml glucose | −5 milli-dB |

Figure 12I:
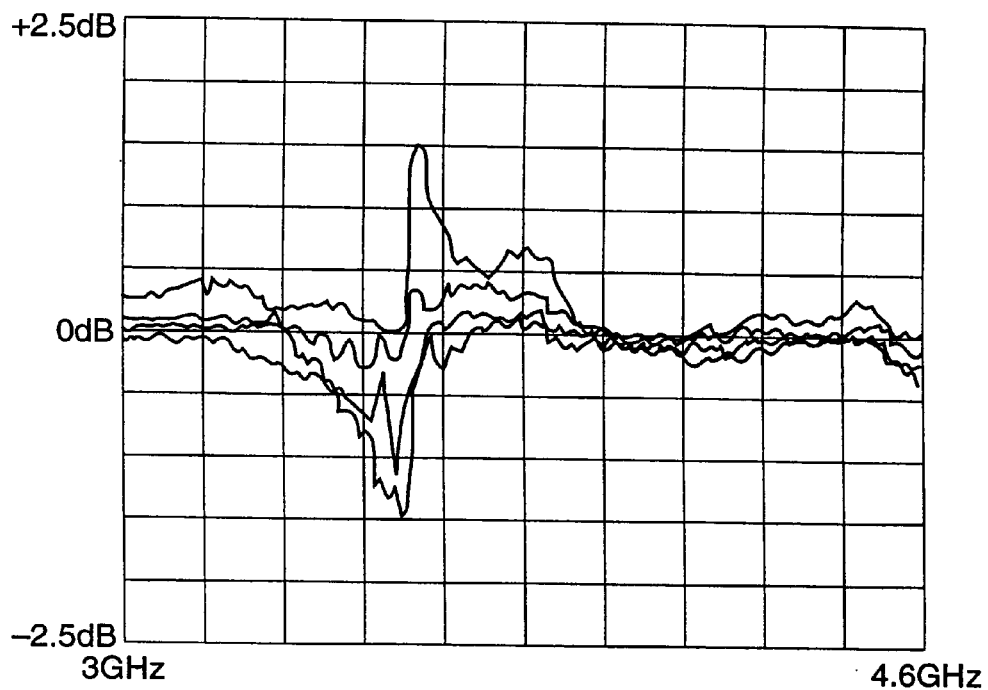
FIG. 12I illustrates the return loss of con-A as a function of glucose concentration at resonance.

A simple glucose titration was also carried out at a resonant point in the spectrum of con-A. FIG. 12I shows the change in the return loss as a function of glucose concentration at this resonance point, demonstrating two effects: First, glucose has a dose-response effect as a ligand which is based on the effect it has on the antiligand (which in this case is con-A). Second, there are regions in the spectra which show a much more sensitive response to the ligand/antiligand binding event than other regions.

A succession of serial dilutions of the dextran solution which took the concentration down below one picomolar ($10_{-15}$ Molar) showed that even at these low concentrations, a significant signal response indicating binding occurred. The time required for the accumulation of the signal ranged from several minutes to ten minutes, but the response was characteristic of the detection of dextran at higher concentrations.

F. Example 6
Detection of Nucleic Acids

In order to demonstrate the ability to detect nucleic acids, a bio-assay device with polylysine as the antiligand attached to a gold surface was fabricated. Using a bio-assay device similar to the one cited in example 1 above except for the gold surface, and prepared and characterized in a similar manner, a high concentration solution (about 20 uM) of calf-thymus DNA was prepared in a d-PBS buffer. The polylysine was placed on the bio-assay device, and the transmission loss response was measured. The response was checked for stability over time and saved. The chamber was then flushed with the buffer, the response again checked for changes with the flush and stability thereafter, and the response stored as the baseline response.

Figure 12J:
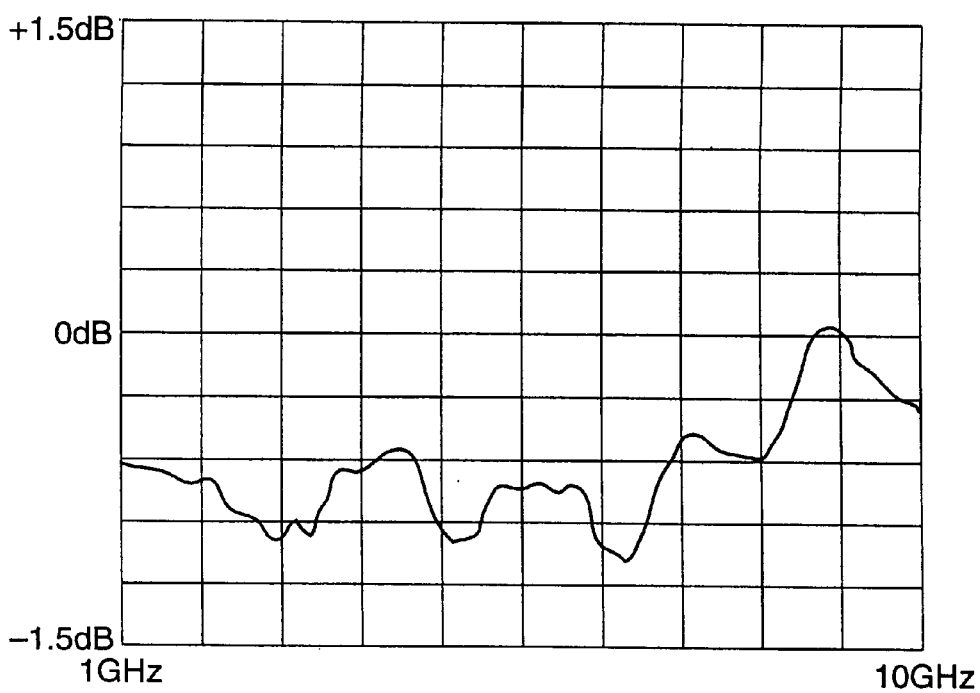
FIG. 12J illustrates the transmission loss of DNA/Polylysine complexes relative to the Polylysine response.

A solution containing the DNA was then placed in the bio-assay device, and the change in the response was measured by subtracting the resulting response from the baseline response, and observed for stability. The bio-assay device was flushed with buffer to remove the DNA in the bulk, leaving only the DNA/Polylysine complexes on the bio-assay device surface. The resulting change is shown in FIG. 12J.

G. Example 7
The Effects of pH and Salinity

Figure 12K:
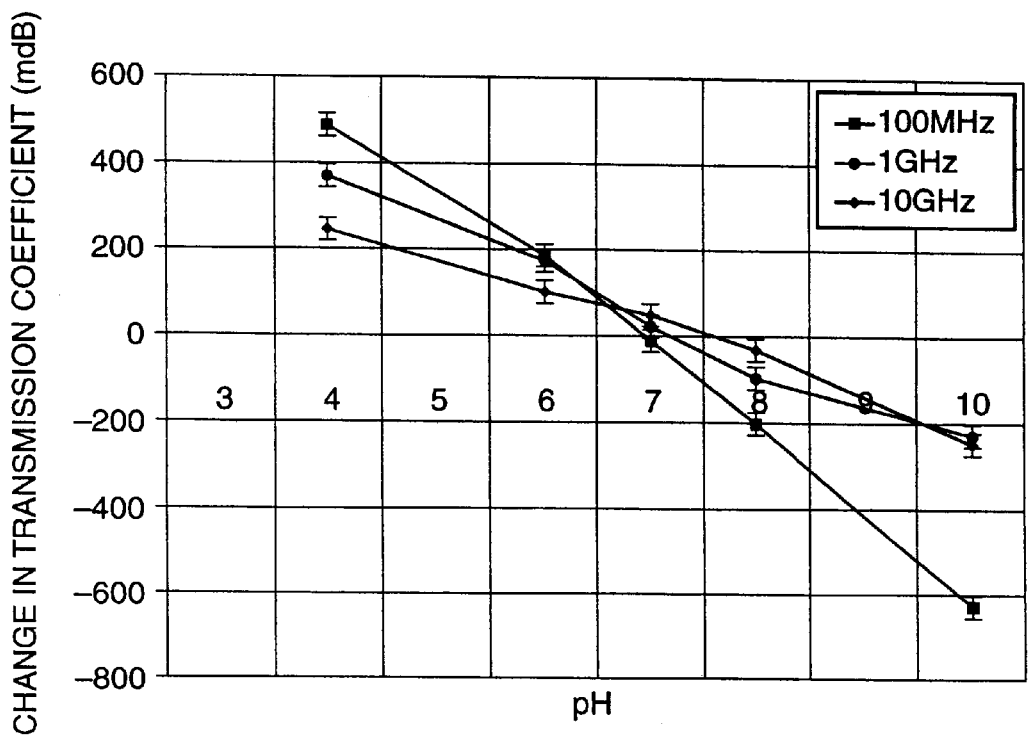
FIG. 12K illustrates the change in the transmission loss response as a function of pH for a series of buffers at 100 MHz, 1 GHz, and 10 GHz.

The effects of pH and salinity in the signal were measured in two different experiments. To investigate the effects of the pH, a series of buffers or pH ranging from 3.94 to 9.80 were measured. The 60 Hz conductivity for each buffer was measured to correct for the change in free ions. Subsequently, transmission loss responses at 100 MHz, 1 GHz, and 10 GHz was measured. The results are shown in FIG. 12K.

Figure 12L:
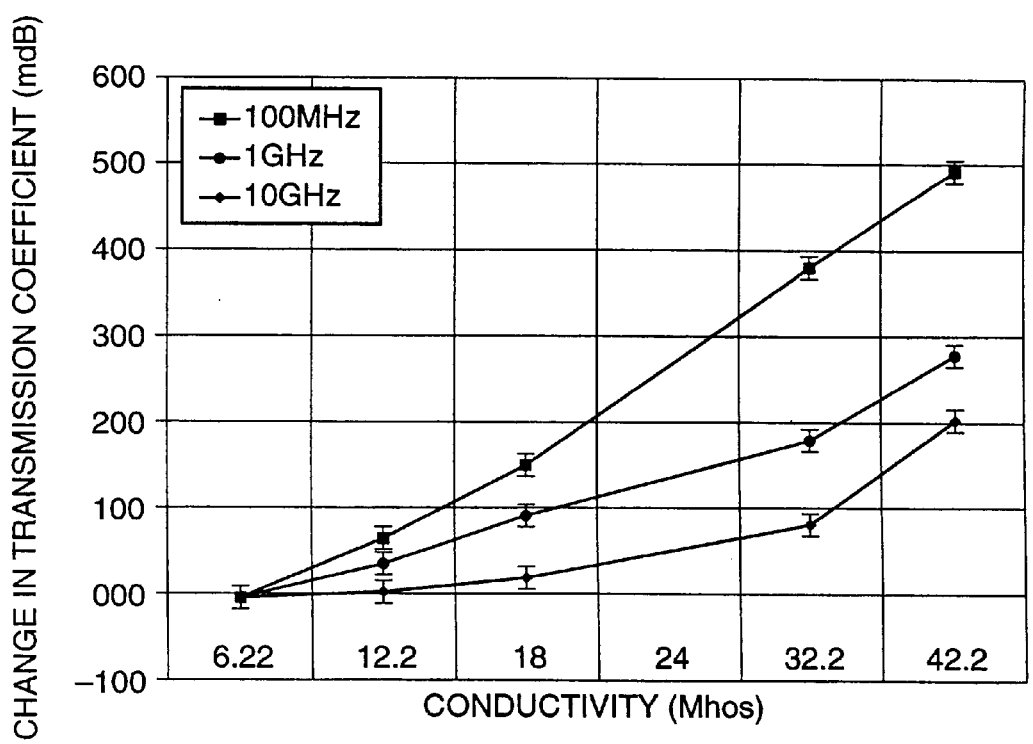
FIG. 12L illustrates the change in the transmission loss response as a function of ionic concentration for a series of buffers at 100 MHz, 1 GHz, and 10 GHz.

A similar experiment was carried out to determine the effects of changing the ionic concentration of a solution. Several solutions were made, starting with a simple d-PBS, and adding various amounts of sodium chloride. The 60 Hz conductivity was then measured and noted, and the samples were serially placed in the bio-assay device and the transmission response was measured at 100 MHz, 1 GHz, and 10 GHz. These results are plotted in FIG. 12L.

As both of these plots show, certain environmental changes result in changes in the measured parameters.

H. Example 8
Detection in Whole Blood:

The detection of troponin-I (TN-I) was made in whole, unprocessed human blood was made to verify detection capability in messy environments. The unprocessed human blood was treated with sodium citrate to anticoagulate. An anti-TN-I antibody corresponding to the epitope of TN-I was used for calibration purposes. The interface transmission line of the bio-assay device was coated with anti-TN-I Ab (antiligand). A sample of blood was spiked to a 10 ng/ml concentration of TN-I and a second identical sample of blood was left unspiked as a control.

The experiment consisted of attaching the anti-TN-I Ab antiligand to the device; then first running the unspiked sample across the device; flushing the sample chamber several times to see what the noise of exchange was; followed by the spiked sample, which was also replaced several times to establish a noise floor. In each case, the change in the transmission loss was measured. As a check, the anti-TN-I Ab antiligand was removed from the device. The experiment was subsequently repeated as a control to determine if any other properties of the two blood samples (assumed identical except for the TN-I spike) were responsible for the change. The following table shows the result of this experiment for aprobe signal at 1 GHz.

|  | Unspiked sample | Spiked Sample |
| --- | --- | --- |
| Control | <20 milli-dB | <20 milli-dB |
| Anti-TN-I | <20 milli-dB | +275 milli-dB |

Figure 12M:
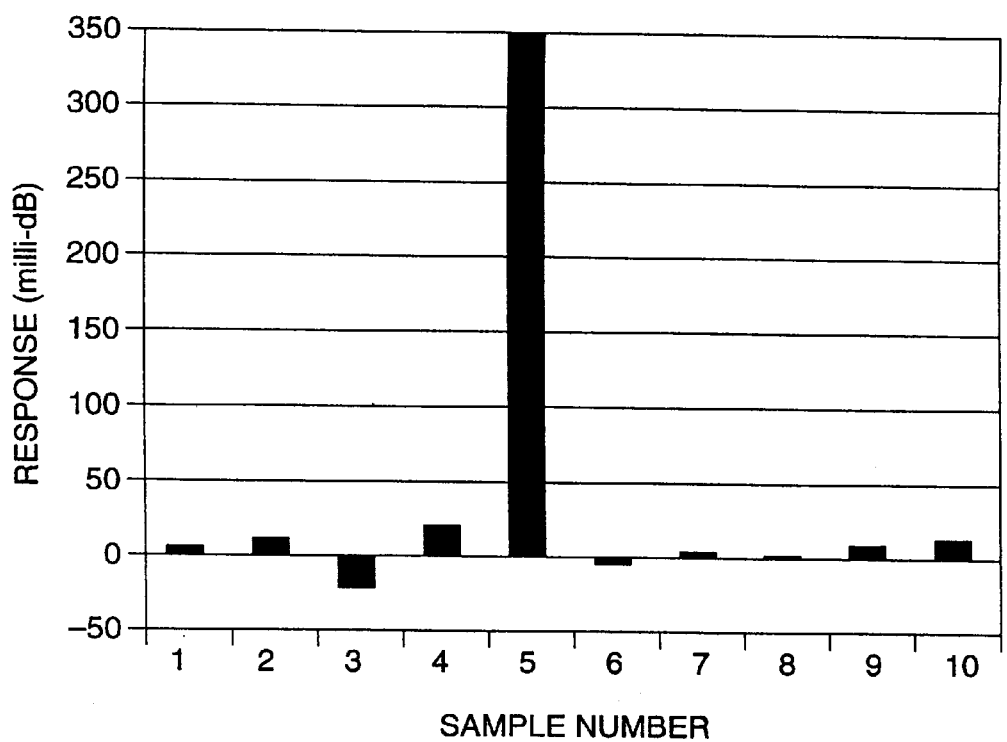
FIG. 12M illustrates the transmission loss response for 10 samples of whole blood probed at 1 GHz indicating detection capability in a complex environment.
Figure 12N:
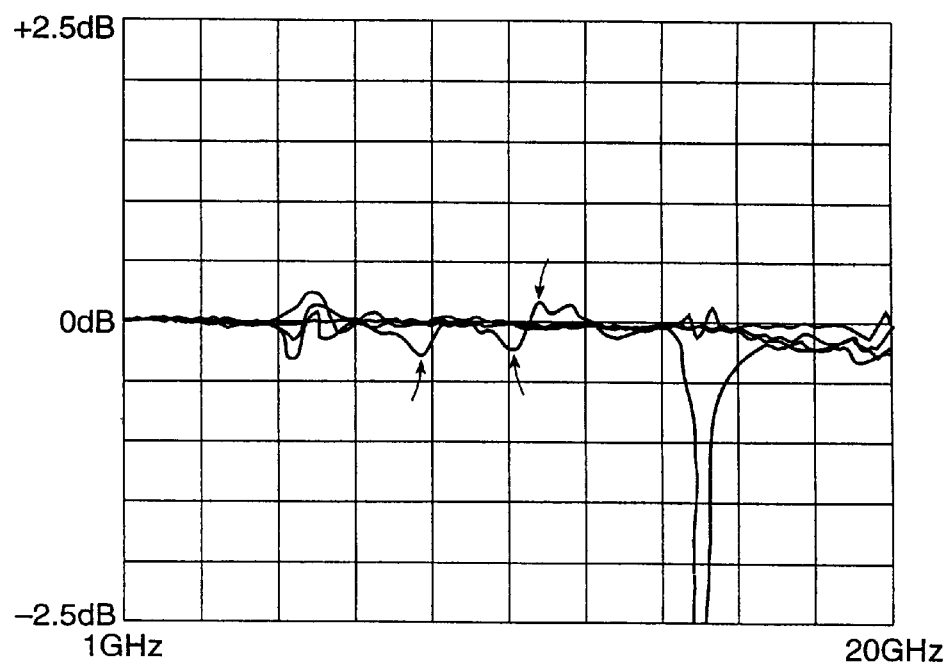
FIG. 12N illustrates the result of avidin binding indicating quadrapole moment detection.

In a second series of experiments, ten different samples of blood were obtained from a clinical laboratory, untreated except for being anticoagulated with heparin. One of the samples was divided into two parts, and one of the parts was spiked with the TN-I antigen as described in the previous paragraph. The bio-assay device was then prepared with the anti-TN-I antibody on the surface. Each sample was then serially passed through the bio-assay device, saving the spiked sample for last. The responses for each of these samples, probed at 1 GHz as in the previous experiment, and shown in FIG. 12M. The spiked sample was clearly distinguishable form the rest of the (unspiked) samples.

I. Example 9
Detection of the Quadrupole Moment of a Molecule

The effect of binding avidin to a gold surface was investigated to determine the detectablity of a molecule's quadupole moment. Avidin is a tetramer which has a very small dipole moment in the unbound state owing to the symmetry of the molecule in the unbound state. Figure N shows the result of avidin binding with characteristic peaks as shown in the plot. Note that these peaks are markedly smaller than the peaks which arise due to the binding of biotin, as shown in FIG. 12G.

VII. Applications

The methods and systems of the present invention may be used in a variety of applications, examples of which are described herein.

The present invention could be used to quantitate the level of binding between a ligand and an antiligand and thus be used to determine the effect of other molecules on the activity of an enzyme. For instance, other molecules in the solution could decrease or increase the level of the binding and thus the identity of enzyme inhibitors or inducers could be determined.

The presence of infectious pathogens (viruses, bacteria, fungi, or the like) or cancerous tumors can be tested by monitoring binding of an antiligand to the pathogen, tumor cell, or a component of the pathogen or tumor, such as a protein, cell membrane, cell extract, tumor markers like CEA or PSA, other antigenic epitopes or the like. For example, the invention is capable of detecting the pathogen or tumor by detecting the binding of pathogenic or tumor markers in the patient's blood with an antibody on the bio-assay device. In addition for example, the binding of an antibody from a patient's blood to a viral protein, such as an HIV protein is a common test for monitoring patient exposure to the virus. Another common example is the quantitation of Prostate Specific Antigen (PSA) in patient blood as a marker for the progression of prostate cancer.

Additionally, drug receptor interactions, including both membrane and non-membrane receptors and receptor conformational changes as a result of drug binding can be determined with the present invention. In another aspect, the invention can be used to provide information on lipid interactions, such as lipo-proteins binding to lipids, and liposomal interactions with lipids.

In additional embodiments, the technology of the invention can be used to provide gene chips for screening nucleic acid samples and proteomics chips for cataloging and describing proteins. Such chips can make use of the unique ability of the invention to measure simultaneously the affinity, kinetics, and unique dielectric signatures of each binding event; and to make these measurements at a multiplicity of addressable test sites on the chip. The exact nature of the addressing will depend on the applications, but the general strategy is as follows: Define a vector space by the variables $K_{eq}$, $k_A$, and $\omega=(\omega 1,\omega 2,\omega 3, \ldots)$ where these variables represent the equilibrium constant, the kinetic constant, and a basis set of N frequencies at which the dielectric properties are probed. An N+2 dimensional space is thus defined into which every binding event can be mapped. A group of reference molecules is subsequently chosen which represents a spectrum of binding events of interest, such as a group of oligonucleotides with different nucleic acid sequences or a selection of antibodies which are specific for protein domains or other sub-structures of proteins, and attach them to addressable points on the chip. A particular species of molecules or group of species is introduced to the chip, and each address is then probed for the value of each of the points in the vector space defined above (or a suitable subset thereof). Each species can then be represented by an address in the vector space. The complexity of the system will depend on the size of the vector space and the total number of different immobilized ligands on the surface.

As an example of the above, consider a simple system comprised of two different nucleic acid probes which are analyzed at four different frequencies; and further, each of these frequencies can be parsed into ten different amplitudes. Such a system would have 100 million possible addresses ($10^4$ for the first polymorphism and $10^4$ for the second polymorphism). An unknown placed in the system will be represented by a unique address of the form [(1,5,3,7)(4,8, 6,7)], where the first four numbers represent the spectral response of the first probe at the four selected frequencies, and the latter four numbers represent the spectral response of the second probe at the four selected frequencies. Thus with just two probes and four frequencies, 100 million unique addresses can be generated.

"Smart Needle" IV assays, which provide a miniature bioassay device in the bore of a needle, can also be made to use the technology of the present invention. This embodiment can be used to provide cost-effective and safe medical diagnostics devices for use in emergency rooms and other points-of-care settings and the like. Examples of uses include: diagnosing acute conditions such as heart attacks, infectious diseases like bacterial meningitis or Group B Step infections in the neonatal/perinatal setting, coagulopathies, fetal and neonatal oxygenation in the intensive care setting; diagnosing chronic conditions in point-of-care settings such as health care provider offices and remote locations.

A bio-assay device bearing a plurality biological binding partners permits the simultaneous assay of a multiplicity of analytes in a sample. In addition, the measurement of binding of a single analyte to a number of different species of biological binding partners provides a control for non-specific binding. A comparison of the degree of binding of different analytes in a test sample permits evaluation of the relative increase or decrease of the different analytes.

The bio-assay device of this invention can be used to detect virtually any analyte in vivo or ex vivo. While in a preferred embodiment the analyte may be a biological molecule, it need not be so limited so long as a specific binding partner is available or some other property of the analyte can be measured in some embodiment of the invention described herein. Suitable analytes include virtually any analyte found in biological materials or in materials processed therefrom. Virtually any analyte that can be suspended or dissolved preferably in an aqueous solution can be detected using the methods of this invention. Examples of analytes of interest include 1) antibodies, such as antibodies to HIV 2), *Helicobacter pylori*, hepatitis (e.g., hepatitis A, B and C), measles, mumps, and rubella; 2) drugs of abuse and their metabolic byproducts such as cotinine, cocaine, benzoylecgonine, benzodizazpine, tetrahydrocannabinol, nicotine, ethanol; 3) therapeutic drugs including theophylline, phenytoin, acetaminophen, lithium, diazepam, nortryptyline, secobarbital, phenobarbitol, and the like; 4) hormones and growth factors such as testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factor I and II, growth hormone release inhibiting factor, and sex hormone binding globulin; and 5) other analytes including glucose, cholesterol, caffeine, corticosteroid binding globulin, DHEA binding glycoprotein, and the like.

As indicated above suitable analytes include, but are not limited to proteins, glycoproteins, antigen, antibodies, nucleic acids, sugars, carbohydrates, lectins, and the like. However, larger, multimolecular, entities, such as cells, cell membranes and other cellular constituents can also be detected and/or quantified by the methods of this invention. Thus, for example, microorganisms (e.g. bacteria, fungi, algae, etc.) having characteristic surface markers (e.g. receptors, lectins, etc.) can be detected and/or quantified (e.g. in a biological sample from an animal, or plant). Similarly, cell types (e.g. cells characteristic of a particular tissue) having characteristic markers (e.g. tumor cells overexpressing IL-13 receptor (see, e.g., U.S. Pat. No. 5,614, 191)). Thus, cells indicative of particular pathologies, particular states of differentiation (or lack thereof) or particular tissue types can be detected and/or quantified.

Conjugation of the Biological Binding Partner (ligand or antiligand) Effector Molecule "Chip" Surface.

In one embodiment, the biological binding partner (ligand or antiligand) is chemically conjugated to the underlying surface (e.g. the bio-electric interface.) Means of chemically conjugating molecules are well known to those of skill (see, e.g., Chapter 4 in *Monoclonal Antibodies: Principles and Applications*, Birch and Lennox, eds. John Wiley & Sons, Inc. N.Y. (1995) which describes conjugation of antibodies to anticancer drugs, labels including radio labels, enzymes, and the like).

The procedure for attaching a binding partner (e.g. a protein, antibody, glycoprotein, nucleic acid, lectin, sugar, carbohydrate, etc.) to a surface will vary according to the chemical structure of the binding partner. Polypeptides typically contain variety of functional groups; e.g., carboxylic acid (COOH) or free amine ($-NH_2$) groups, which are available for reaction with a suitable functional on the surface or linker to which they are to be bound. Similarly, other biological molecules, e.g. nucleic acids, sugars, carbohydrates, all contain a variety of functional groups (e.g. OH, $NH_2$, COOH, $-S$, etc.) that are suitable points for linkage.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that may be used to join the biological binding partner (e.g. ligand or antiligand) to the underlying (e.g. apparatus or device) surface. The linker is capable of forming covalent bonds to both the biological binding partner and to the underlying surface. Suitable linkers are well known to those of skill in the art and include, but are not limited to, straight or branched-chain carbon linkers, heterocyclic carbon linkers, or peptide linkers.

A bifunctional linker having one functional group reactive with a group on the surface, and another group reactive with the binding partner may be used to form the desired conjugate. Alternatively, derivatization may involve chemical treatment of the binding partner and/or the substrate. For example, a silica or glass substrate can be silanized to create functional group. Similarly, a protein or glycoprotein, can be derivatized, e.g., by glycol cleavage of a sugar moiety attached to the protein antibody with periodate to generate free aldehyde groups. The free aldehyde groups on the antibody or protein or glycoprotein may be reacted with free amine or hydrazine groups on athe surface to bind the binding partner thereto (see U.S. Pat. No. 4,671,958). Procedures for generation of free sulfhydryl groups on polypeptide, such as antibodies or antibody fragments, are also known (see U.S. Pat. No. 4,659,839).

Many procedures and linker molecules for attachment of various biological molecules to various metal, glass, plastic etc., substrates are well known to those of skill in the art. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071–4075. Methods of conjugating antibodies, proteins, and glycoproteins abound in the immunotoxin literature and can be found, for example in "Monoclonal Antibody-Toxin Conjugates: Aiming the Magic Bullet," Thorpe et al., Monoclonal Antibodies in Clinical Medicine, Academic Press, pp. 168–190 (1982), Waldmann, Science, 252: 1657 (1991), U.S. Pat. Nos. 4,545,985 and 4,894,443.

Use of Nucleic Acid Binding Partners

Where the binding partner is a nucleic acid (e.g. DNA, RNA, peptide nucleic acid, etc.) specific binding is preferably achieved under "stringent" conditions, the more stringent the conditions, the more specific the hybridization.

The selection of stringent conditions for any probe/target combination is routinely accomplished by those of ordinary skill in the art. Moreover stringency can be determined empirically by gradually increasing the stringency of the conditions (e.g. increasing salt, raising temperature, etc.) until the desired level of specificity is obtained.

"Starting points" for stringent conditions are well known. For example, desired nucleic acids will hybridize to complementary nucleic acid probes under the hybridization and wash conditions of 50% formamide at 42° C. Other stringent hybridization conditions may also be selected. Generally, stringent conditions are selected to be about 5° C. lower than the thermal melting point ($T_m$) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one. An extensive guide to hybridization of nucleic acids is found in Ausubel et al., *Current Protocols in Molecular Biology current Protocols*, a joint venture between Greene Publishing Associates, Inc and John Wiley and Sons, Inc. (supplemented through 1998).

Oligonucleotides for use as binding partners are chemically synthesized, for example, according to the solid phase phosphoramidite triester method first described by Beaucage, S. L. and Carruthers, M. H., 1981, Tetrahedron Lett., 22(20):1859–1862 using an automated synthesizer, as described in Needham-VanDevanter, D. R., et al., 1984, Nucleic Acids Res., 12:6159–6168. Purification of oligonucleotides is by either native acrylamide gel electrophoresis or by anion-exchange HPLC as described in Pearson, J. D. and Regnier, F. E. (1983) J. Chrom. 255:137–149. The sequence of the synthetic oligonucleotide can be verified using the chemical degradation method of Maxam, A. M. and Gilbert, W. (1980) in Methods Enzymol. 65:499–560.

The bio-assay device will have a variety of uses, including for example, screening large numbers of molecules for biological activity or screening biological samples for the presence or absence concentration of a particular component or components. To screen for biological activity, for example, the binding layer is exposed to one or more receptors, such as antibodies or whole cells. By detecting an interaction between the binding layer antiligand and the ligand, the presence and concentration can be determined. A particular advantage of this technique is that no labels are needed to detect this interaction. The inherent properties of the individual molecules are used to detect their presence and amount, absence, or interaction with other molecules.

Other possible applications for the bio-assay device or chip include diagnostics, in which various antibodies for particular receptors would be used to form the binding layer, and blood would be screened for immune deficiencies for example. The bio-assay device is optionally fabricated such that it fits into a hypodermic needle bore. Only a tiny blood sample would be necessary to detect a binding to a pre-applied antiligand on the binding layer. A diagnostic assay can be made to measure a whole range of clinically relevant analytes, from pathogens such as viruses or bacteria, to metabolic activities like glucose concentration or lipid levels, to the usual sets test for liver enzymes, electrolytes, clotting factors, specific antibodies like ANA (used in rheumatological disorders) and allergic response antibodies, arterial blood oxygenation, drugs of abuse, and the like.

The bio-assay devices used in this capacity could be inexpensive disposable chips, since they are easily fabricated and not limited to semiconductor processing. For example, the chips are optionally fabricated on cheap materials like plastic or glass substrates. The chips are then optionally placed in a device as described below and a signal propagated through the bio-assay device to detect the binding interactions due to ligands in the blood. In fact, many different shapes and sizes of the bio-assay devices could be fabricated containing various binding layers for the countless biological and chemical applications for which detection without a label would be useful.

Unknown and uncharacterized proteins may be classified and/or identified by detecting binding to structural motifs on the unknown protein. For example, proteins in the same or similar class have structural homologies; that is to say, substructures such as domains that recur within a given class of proteins. By fabricating a chip with multiple addressable arrays, each of which has a antiligand for a specific substructure, an unknown molecular species could be classified and/or identified as follows: The presence of particular substructures is detected by the binding of each to its respective antiligand. Each of these sub-structure binding events is then characterized by such qualities as affinity, kinetics, and spectral response. Correlation is then made between the responses of the unknown molecular species and data obtained from known proteins. In the case that no exact fit is found, much of the structural details of the unknown compound can be pieced together in much the same manner as NMR Spectroscopy does for organic molecules.

In another embodiment, this technique may be used to develop gene chips for the detection of nucleic acids. Gene chips are arrays of nucleic acids that are used for the detection of complementary nucleic acids in a sample. The existence of the complementary DNA, as measured by binding to distinct DNA molecules on the gene chip, is the desired output. In the event that complementary binding does not occur, partial hybridization can be detected and characterized by measuring such physical quantities as affinity, melting point or other stringency conditions, and the direct spectral response of the signal and correlation with previously measured data. In this manner, a single antiligand in the form of a nucleic acid sequence can detect a whole range of polymorphisms without the need for a separate sequence for each of the polymorphisms. For example, a chip with just a few hundred different nucleic acid sequences could detect tens of thousands of different polymorphisms.

Gene chips can be designed for the identification of drug targets, bacterial identification, genotyping, and other diagnostics needs. The technique requires the attachment of the requisite nucleic acids, typically as probes, onto a substrate and a method to measure binding of complementary nucleic acids to that substrate. Ordinarily, the nucleic acids of the sample need to be labeled, most commonly with a fluorescent probe. This technology eliminates the need for labeling the sample DNA and the associated problems. Gene chips can be developed for specific needs in drug target identification, molecular diagnostics, and detection and identification of biological warfare agents. Other types of devices that could be fabricated and utilized are immunoassay devices, drug discovery devices, and toxicity testing devices, analytical devices, and the like.

The invention described herein can also be used for many aspects of new drug development, from the initial screening process all the way though patient typing and therapeutic monitoring. In the initial stages of drug discovery, the invention can be used to facilitate target identification, validation, and high throughput screening (HTS). Target receptors can be the antiligand on the bio-assay device, and by characterizing the actions of known agonists, antagonists, or allosteric effectors, initial targets for the high throughput screening procedure can be rapidly identified and validated. In the HTS process, hundreds of thousands of compounds are tested to determine which of them can bind to the target. The invention described herein can be miniaturized, so that highly parallel screening platforms can be realized; platforms which are capable of screening hundreds or thousands of compounds simultaneously, and at the same time determining the effect of binding (e.g. agonist or antagonist), affinity, kinetics, etc. Additionally, such miniature systems require very small amounts of compound, thus greatly saving costs in purchasing said compounds from combinatorial libraries. The system of detection formed through use of the bio-assay device provides a high throughput detection system because detection optionally occurs in real time and many samples can be rapidly analyzed. The response period is optionally monitored on a nanosecond time scale. As soon as the molecules are bound to each other, detection occurs. More time is optionally required to measure low concentrations or binding events between molecules with a low binding affinity. The actual time is optionally limited by diffusion rates. Other than these potential limitations, thousands of compounds are optionally run through the system very quickly, for example, in an hour. For example, using chip fabrication technologies, a 10,000 channel device (using some of the emerging microfluidics technologies) is possible, and with small volumes and thus short diffusion times, and kinetic measurements measuring only the beginning of the reaction, 10 million samples per hour are optionally measured. With known concentrations, the binding affinity is optionally calculated from the kinetics alone and thus the device can be probed at a very fast time scale and the affinity calculated and/or estimated from the slope of the kinetic curve. References for kinetics and affinities can be found in any standard biochemistry or chemistry text such as Mathews and van Holde, *Biochemistry*, Benjamin Cummings, New York, 1990.

The invention may be easily extended into cell-based assays, since the detection may not require sample purification and amplification. In these classes of applications, cellular systems may be monitored for various changes either by detecting external expressions or by lysing the cell to release the cytosolic constituents and detect the presence of one or more analytes of interest.

The invention may also be adapted to "Laboratory-on-a-Chip" applications. Because of the ease of miniaturization, very small chips with thousands or tens of thousands of addressable bio-assay devices contained therein may be realized. The detector may be realized as a sort of "logic gate" in which the presence of a particular ligand or analyte has the effect of either turning on the gate or turning off the gate, as is appropriate for a given application. Such a gate may be realized in any number of ways which translate the binding event into an electromagnetic signal which can be assigned to one of two possible states corresponding to off and on, 1 or 0, and the like. The two states could be different frequencies of a resonant cavity or waveguide corresponding to bound and unbound, or amplitude changes in a transmission line or waveguide which correspond to bound and unbound, or changes in the band-pass of a particular circuit, or the like.

While the above is a complete description of possible embodiments of the invention, various alternatives, modifications, and equivalents may be used. For instance a person skilled in the art will appreciate that the signal path of foregoing bio-assay device is not limited to a transmission line. Other transmission mediums, such as conductive or dielectric waveguides may alternatively be used. Further, all publications and patent documents recited in this application are incorporated by reference in their entirety for all purposes to the same extent as if each individual publication and patent document was so individually denoted. The above description should be view as only exemplary embodiments of the invention, the boundaries of which are appropriately defined by the metes and bounds of the following claims.

What is claimed is:

1. A bio-assay device configured to detect a molecular binding event formed between a ligand and an antiligand, the bio-assay device comprising:

(i) a signal path operable to support the propagation of a test signal at one or more frequencies from 10 MHz to 1000 GHz, said signal path comprising:

an electrically conductive transmission line;
a ground element; and
a dielectric layer interposed between said electrically conductive transmission line and said ground element; and (ii) a molecular binding layer electromagnetically coupled to said signal path, said molecular binding layer comprising said antiligand operable to bind said ligand, wherein said molecular binding layer is located between at least a portion of said electrically conductive transmission line and at least a portion of said ground element.

2. The bio-assay device of claim 1, further comprising:
an input port coupled to said signal path, said input port comprising:
a first signal conductor coupled to said transmission line; and
a first ground conductor coupled to said ground element; and
an output port coupled to said signal path, said output port comprising:
a second output signal conductor coupled to said transmission line; and
a second ground conductor coupled to said ground element.

3. The bio-assay device of claim 1, wherein said molecular binding layer is formed along at least a portion of said electrically conductive transmission line.

4. The bio-assay device of claim 1, wherein said molecular binding layer is formed along at least a portion of said ground element.

5. The bio-assay device of claim 1, wherein said transmission line is physically separated from said ligand.

6. The bio-assay device of claim 1, wherein said test signal comprises a signal at one or more frequencies from 45 MHz to 20 GHz.

7. The bio-assay device of claim 1, wherein said electrically conductive transmission line comprises a derivatized surface and said antiligand is attached to said derivatized surface.

8. A bio-assay test system configured to detect the presence or absence of a molecular binding event formed between a ligand and an antiligand, the system comprising:

(i) a signal source operable to provide a test signal at one or more frequencies from 10 MHz to 1000 GHz;

(ii) a bio-assay device, comprising:
(a) a signal path operable to support the propagation of said test signal, said signal path comprising:
an electrically conductive transmission line;
a ground element; and
a dielectric layer interposed between said electrically conductive transmission line and said ground element; and (b) a molecular binding layer electromagnetically coupled to said signal path, said molecular binding layer comprising said antiligand operable to bind to said ligand, wherein said molecular binding layer is located between at least a portion of said electrically conductive transmission line and at least a portion of said ground element; and (iii) a signal detector coupled to said bio-assay device, wherein said test signal couples to said molecular binding layer, thereby producing said modulated signal, said modulated signal being recoverable by said signal detector, wherein said modulated signal exhibits a response indicating the presence or absence of a molecular binding event formed between said ligand and said antiligand.

9. The bio-assay test system of claim 8, wherein said signal response comprises an S-parameter transmission loss $S_{21}$ response.

10. The bio-assay test system of claim 8, wherein said signal response comprises an S-parameter return loss $S_{11}$ response.

11. The bio-assay test system of claim 8, wherein said signal source and said signal detector are included within a vector network analyzer.

12. The bio-assay test system of claim 8, wherein said signal source and said signal detector are included within a scalar network analyzer.

13. The bio-assay test system of claim 8, wherein said signal source and said signal detector are included within a time domain reflectometer.

* * * * *